United States Patent
Xia et al.

(10) Patent No.: US 9,175,211 B2
(45) Date of Patent: *Nov. 3, 2015

(54) PHOSPHORESCENT MATERIALS

(75) Inventors: Chuanjun Xia, Lawrenceville, NJ (US); Bert Alleyne, Ewing, NJ (US); Nasrin Ansari, Monmouth, NJ (US)

(73) Assignee: Universal Display Corporation, Ewing, NJ (US)

( * ) Notice: Subject to any disclaimer, the term of this patent is extended or adjusted under 35 U.S.C. 154(b) by 602 days.

This patent is subject to a terminal disclaimer.

(21) Appl. No.: 12/868,350

(22) Filed: Aug. 25, 2010

(65) Prior Publication Data

US 2011/0215710 A1  Sep. 8, 2011

Related U.S. Application Data

(60) Provisional application No. 61/339,337, filed on Mar. 3, 2010.

(51) Int. Cl.

| | | |
|---|---|---|
| H01L 51/54 | (2006.01) | |
| C09K 11/06 | (2006.01) | |
| H01L 51/00 | (2006.01) | |
| H01L 51/50 | (2006.01) | |
| C07F 15/00 | (2006.01) | |
| H05B 33/14 | (2006.01) | |

(52) U.S. Cl.
CPC ............ C09K 11/06 (2013.01); C07F 15/0033 (2013.01); H01L 51/0085 (2013.01); H01L 51/5016 (2013.01); H05B 33/14 (2013.01); C09K 2211/1022 (2013.01); C09K 2211/1029 (2013.01); C09K 2211/1033 (2013.01); C09K 2211/1037 (2013.01); C09K 2211/1044 (2013.01); C09K 2211/1059 (2013.01); C09K 2211/185 (2013.01)

(58) Field of Classification Search
CPC ............... C07F 15/0006; C07F 15/002; C07F 15/0033; C07F 15/0046; C07F 15/0073; C07F 15/0086; H01L 51/0085–51/0088; H01L 51/50; H01L 51/5016; C09K 11/06; C09K 2211/1029–2211/108; C09K 2211/185
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,884,363 A | 3/1999 | Tofts | |
| 6,013,982 A | 1/2000 | Thompson et al. | |
| 6,087,196 A | 7/2000 | Sturm et al. | |
| 6,091,196 A | 7/2000 | Codama | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0068536 A1 | 4/2003 | Tsuboyama et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |

(Continued)

FOREIGN PATENT DOCUMENTS

| | | | | |
|---|---|---|---|---|
| EP | 0650955 | 5/1995 | | |
| EP | 1239526 | 9/2002 | | |
| EP | 1725079 | 11/2006 | | |
| EP | 2034538 | 3/2009 | | |
| EP | 2062959 | 5/2009 | | |
| JP | 2003-109758 A | * 4/2003 | ............ | H05B 33/14 |
| JP | 200511610 | 1/2005 | | |
| JP | 2006-096697 A | * 4/2006 | ............ | C07F 15/00 |
| JP | 2007123392 | 5/2007 | | |
| JP | 2007254297 | 10/2007 | | |

(Continued)

OTHER PUBLICATIONS

English language machine translation of JP 2003-109758 A, 2003.*
English language machine translation of JP 2006-096697 A, paragraphs 1 to 323, 2009.*
English language machine translation of JP 2006-096697 A, paragraphs 324 to 642, 2009.*

(Continued)

*Primary Examiner* — Michael H Wilson
(74) *Attorney, Agent, or Firm* — Duane Morris LLP

(57) ABSTRACT

Compounds comprising a 2-phenylpyridine ligand further substituted with a heterocyclic group are provided. In particular, the compound comprises a 2-phenylpyridine ligand further substituted with a nitrogen-containing heterocycle. The compounds may be used in organic light emitting devices to provide devices having improved efficiency and lifetime.

27 Claims, 3 Drawing Sheets

(56) References Cited

U.S. PATENT DOCUMENTS

| | | |
|---|---|---|
| 2004/0174116 A1 | 9/2004 | Lu et al. |
| 2005/0025993 A1 | 2/2005 | Thompson et al. |
| 2005/0027123 A1 | 2/2005 | Takiguchi et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0022588 A1* | 2/2006 | Tsuboyama et al. .......... 313/504 |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0184301 A1 | 8/2007 | Oshiyama et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0179555 A1 | 7/2009 | Kim et al. |
| 2010/0148663 A1 | 6/2010 | Tsai et al. |
| 2011/0124808 A1 | 5/2011 | Akino et al. |

FOREIGN PATENT DOCUMENTS

| | | |
|---|---|---|
| JP | 2008 101114 | 5/2008 |
| JP | 2008101114 | 5/2008 |
| JP | 2008 210941 | 9/2008 |
| JP | 2008210941 | 9/2008 |
| JP | 2008074939 | 10/2009 |
| JP | 2009 267244 | 11/2009 |
| JP | 2009267244 | 11/2009 |
| WO | WO 0139234 | 5/2001 |
| WO | WO 0202714 | 1/2002 |
| WO | WO 0215645 | 2/2002 |
| WO | WO 2003040257 | 5/2003 |
| WO | WO 03060956 | 7/2003 |
| WO | WO 2004093207 | 10/2004 |
| WO | WO 2004107822 | 12/2004 |
| WO | WO 2006009024 | 1/2005 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2006098120 | 9/2005 |
| WO | 2005097943 | 10/2005 |
| WO | 2005101912 | 10/2005 |
| WO | WO 2005123873 | 12/2005 |
| WO | WO 2006056418 | 6/2006 |
| WO | WO 2006072002 | 7/2006 |
| WO | WO 2006082742 | 8/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | 2008044723 | 4/2008 |
| WO | WO 2008/078800 A1 * | 7/2008 ............... C07F 15/00 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009050290 | 4/2009 |
| WO | WO 2008056746 | 5/2009 |
| WO | WO 2009021126 | 5/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009/072821 A2 * | 6/2009 ............... C09K 11/06 |
| WO | WO 2009086028 | 7/2009 |
| WO | WO 2009100991 | 8/2009 |
| WO | WO 2009/157424 A1 * | 12/2009 ............... C09K 11/06 |
| WO | 2010/004877 | 1/2010 |
| WO | WO 2010/004877 | 1/2010 |
| WO | WO 2010/028151 | 3/2010 |

OTHER PUBLICATIONS

English language machine translation of JP 2006-096697 A, paragraphs 643 to 651, 2009.*

Kuwabara, Yoshiyuki et al., Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-.

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral Ru[II] PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional iridium Complexes Based on Carbazole Modules as Highly Efficient Electrophosphors," Angew. Chem. Int. Ed., 45:7800-7803 (2006).

Tang, C.W. and VanSlyke, S.A., "Organic Electraluminescent Diodes," App. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Gao, Zhiqiang et al., "Bright-Blue Electroluminescence From a Silyl-Substituted ter-(phenylene-vinyiene) derivative," Appl. Phys. Lett., 74(6):865-867 (1999).

Baldo, M.A. et al., "Very High-Efficiency Green Organic Light-Emitting Devices Based on Electrophosphorescence," Appl. Phys. Lett., 75(1):4-6 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of CHF$_3$," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Wang, Y. et al., "Highly Efficient Electroluminescent Materials Based on Fluorinated Organometallic Iridium Compounds," Appl. Phys. Lett., 79(4):449-451 (2001).

(56) References Cited

OTHER PUBLICATIONS

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing N^C^N-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenyfimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir at al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5''-Bis(dimesitylbory1)-2,2':5',2''-terthiophene as a Novel Family of Electron-Transporting Amorphous Molecular Materials," *J. Am. Chem. Soc.*, 120 (37):9714-9715 (1998).

Sakamoto,Youichi et al., "Synthesis, Characterization, and Electron-Transport Property of Perfluorinated Phenylene Dendrimers," *J. Am. Chem. Soc.*, 122(8)1832-1833 (2000).

Adachi, Chihaya et al., "Nearly 100% internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Baldo, M. A. et al., "Highly Efficient Phosphorescent Emission From Organic Electroluminescent Devices," *Nature*, 395:151-154 (1998).

Guo, Tzung-Fang et al., "Highly Efficient Electraphosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_9$ Hole-Transport Molecules Based on Indolo[3,2- b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

The International Search Report and Written Opinion in PCT/US2010/051076 application.

* cited by examiner

PHOSPHORESCENT MATERIALS

This application claims priority to U.S. Provisional Application Ser. No. 61/339,337, filed on Mar. 3, 2010, the disclosure of which is herein expressly incorporated by reference in its entirety. The disclosure of WO2010/028151 is also herein expressly incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention relates to phosphorescent materials comprising a 2-phenylpyridine ligand further substituted with a heterocyclic group. These materials may provide devices having improved efficiency and lifetime.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entireties.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the structure:

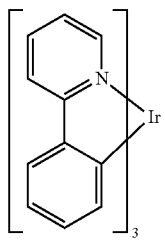

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds having the formula $M(L)_x(L_1)_y(L_2)_z$ are provided.

L is

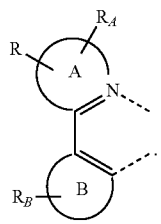

Formula I $L_1$ is

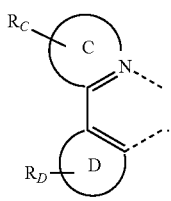

Formula II $L_2$ is

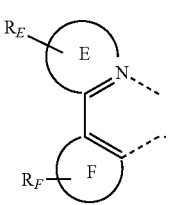

Formula III $L_1$ and $L_2$ can be the same or different. M is a metal having an atomic number greater than 40. Preferably, the metal M is Ir. x is 1, 2 or 3. y is 0, 1 or 2. z is 0, 1 or 2. x+y+z is the oxidation state of the metal M. A is a 6-membered heterocyclic ring. B, C, D, E and F are each independently a 5 or 6-membered carbocyclic or heterocyclic ring. Preferably, B is phenyl. R is a 5 or 6-membered heterocyclic ring. R is attached to A at a position para to the metal M. $R_A$, $R_B$, $R_C$, $R_D$, $R_E$ and $R_F$ may represent mono, di, tri, tetra, or penta substitutions. Each of $R_A$, $R_B$, $R_C$, $R_D$, $R_E$ and $R_F$ is independently selected from the group consisting of hydrogen, alkyl, alkoxy, amino, alkenyl, alkynyl, arylkyl, aryl, and heteroaryl. The ligand L is coordinated bidentately to the metal M. R is a 5 or 6-membered heterocyclic ring that contains at least one nitrogen atom.

In one aspect, the ligand L has the formula:

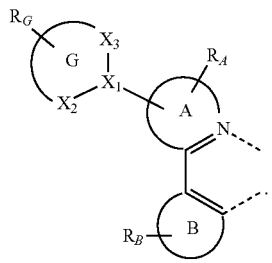

Formula IV

G is a 5 or 6-membered heterocyclic ring. Preferably, G is a 5 or 6-membered heterocyclic ring that contains at least one nitrogen atom. $X_1$, $X_2$, and $X_3$ are independently selected from carbon, oxygen, sulfur and nitrogen. Preferably, $X_1$, $X_2$, and $X_3$ are independently carbon or nitrogen. $R_G$ may represent mono, di, tri, tetra, or penta substitutions. $R_G$ is independently selected from the group consisting of hydrogen, alkyl, alkoxy, amino, alkenyl, alkynyl, arylkyl, aryl, and heteroaryl.

In one aspect, at least one of $X_1$, $X_2$, and $X_3$ is nitrogen. In another aspect, each of $X_1$, $X_2$, and $X_3$ is carbon.

In another aspect, L, $L_1$ and $L_2$ are connected to form a tetradentate ligand and a bidentate ligand or a hexadentate ligand. For example, L and $L_1$ may be connected to form a tetradentate ligand and $L_2$ is a bidentate ligand. Similarly, L and $L_2$ or $L_1$ and $L_2$ may be connected to form a tetradentate ligand while $L_1$ or L is a bidentate ligand. Additionally, L, $L_1$ and $L_2$ may all be connected to form a hexadentate ligand.

In one aspect, the compound is homoleptic. In another aspect, the compound has the formula:

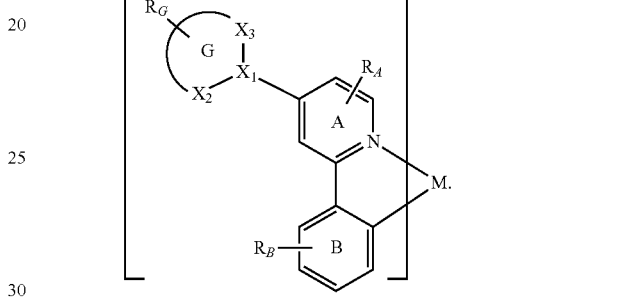

Formula V

In one aspect, the compound is heteroleptic. In another aspect, the compound has the formula:

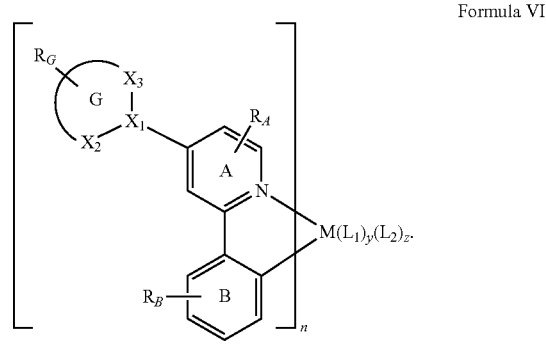

Formula VI n+y+z is the oxidation state of the metal M. n is at least 1. y is 0, 1 or 2. x is 0, 1, or 2.

In one aspect, the ligand L is selected from the group consisting of:

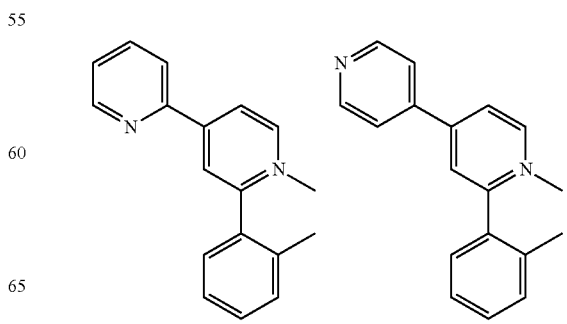

-continued
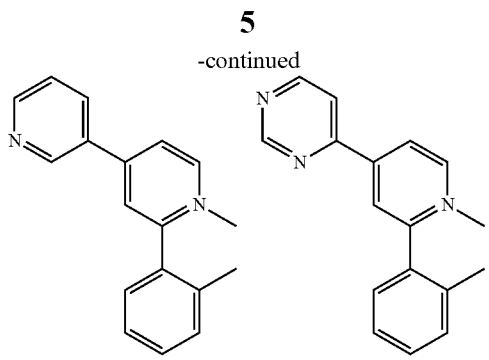
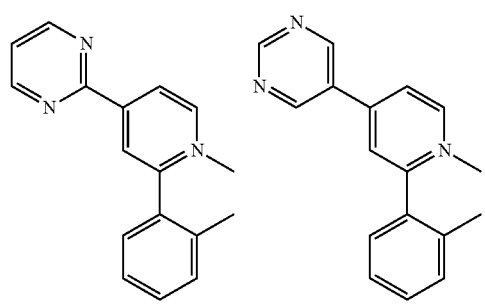
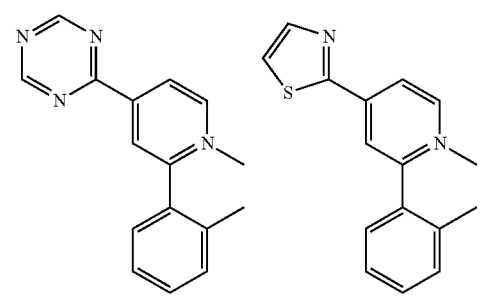
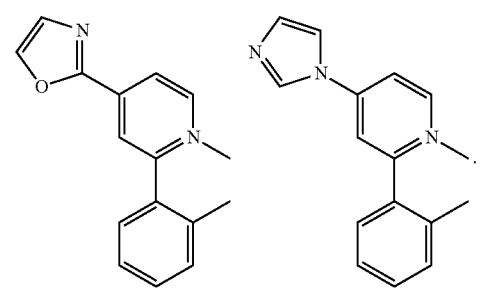
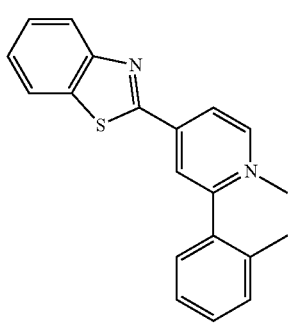
-continued
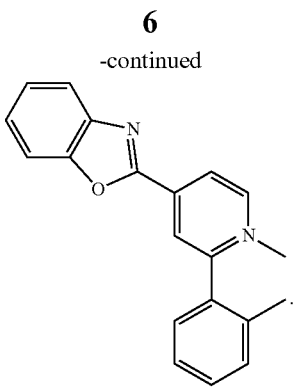
Specific examples of compounds comprising a phenyl pyridine ligand further substituted with a heterocyclic ring are also provided. In particular, the compound is selected from the group consisting of:
Compound 1
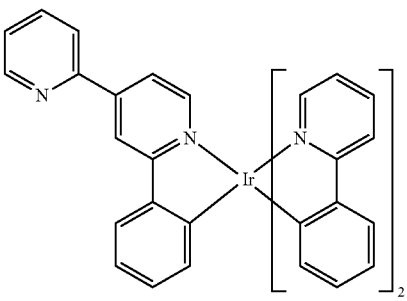
Compound 2
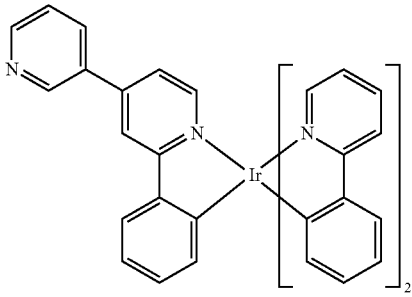
Compound 3
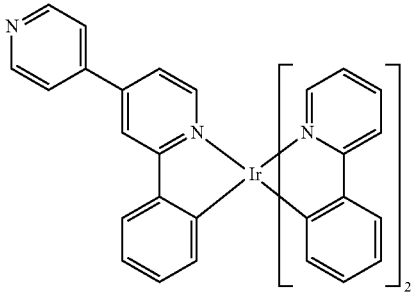

Compound 4
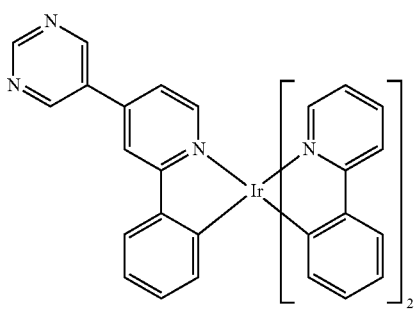
Compound 5
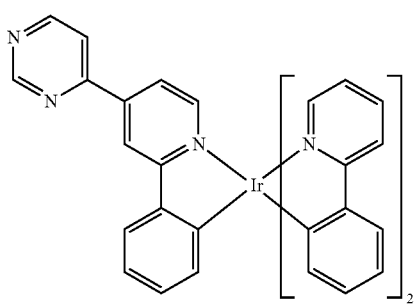
Compound 6
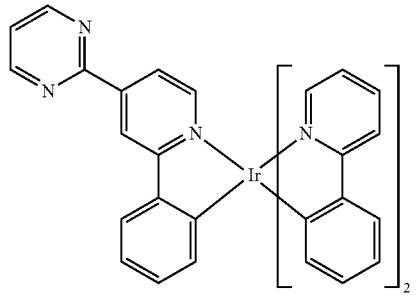
Compound 7
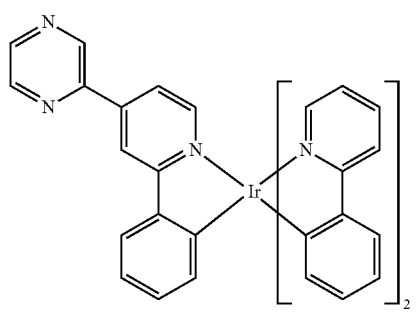
Compound 8
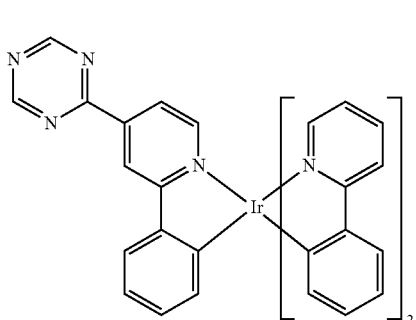
Compound 9
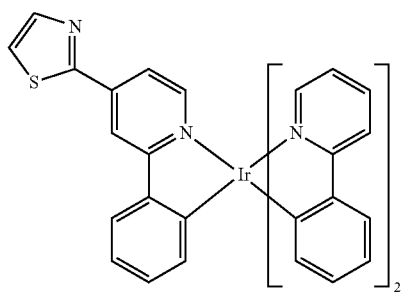
Compound 10
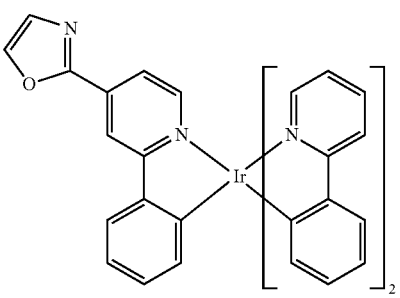
Compound 11
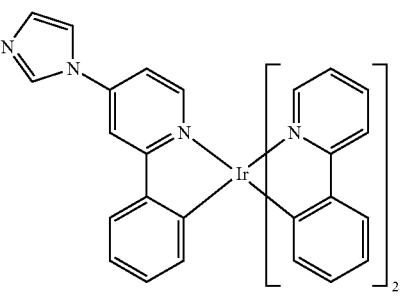
Compound 12
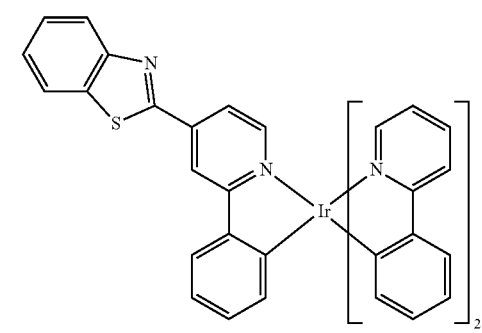
Compound 13
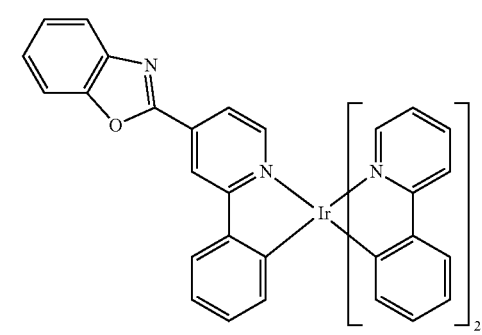

Compound 14
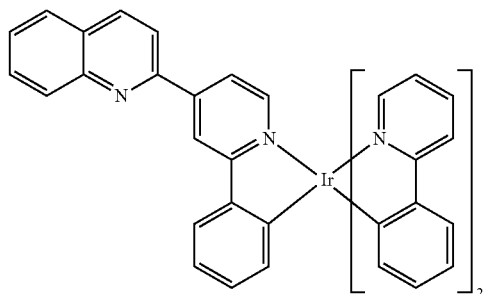
Compound 15
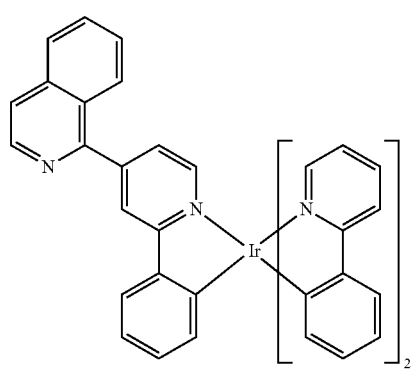
Compound 16
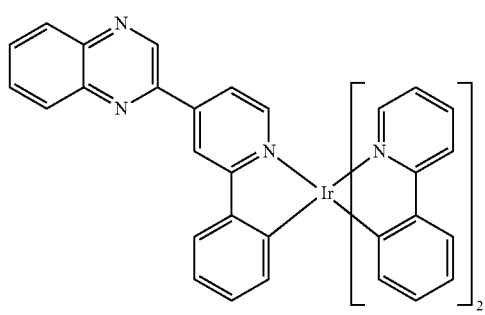
Compound 17
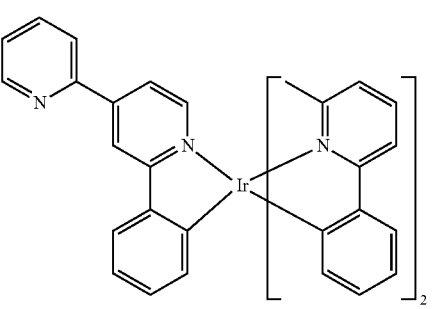
Compound 18
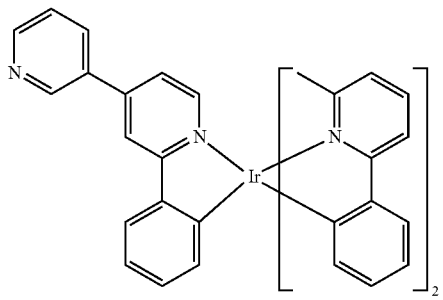
Compound 19
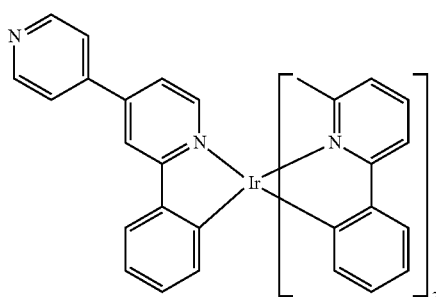
Compound 20
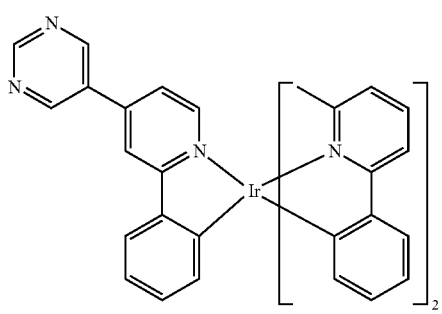
Compound 21
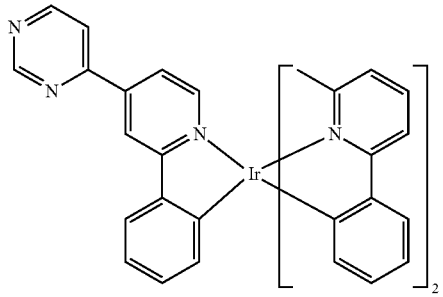
Compound 22
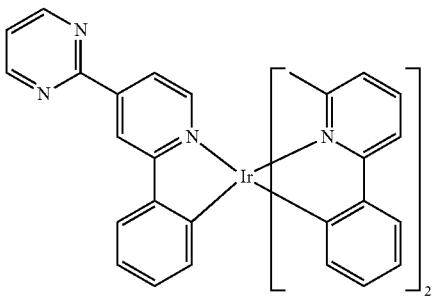

-continued
Compound 23
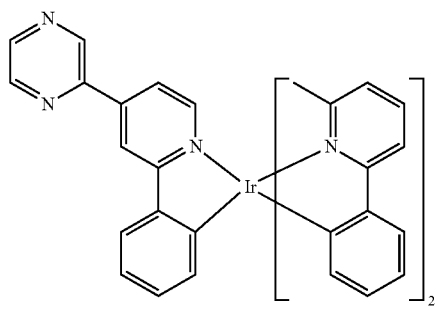
Compound 24
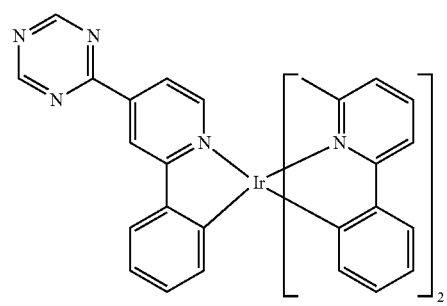
Compound 25
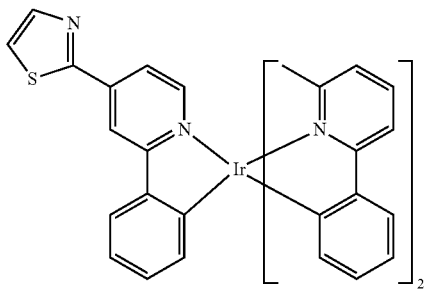
Compound 26
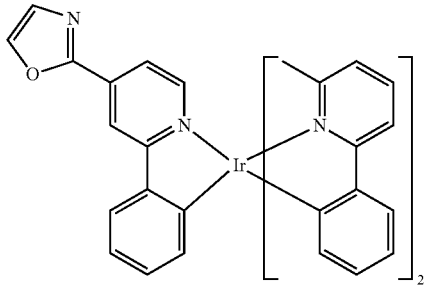
Compound 27
-continued
Compound 28
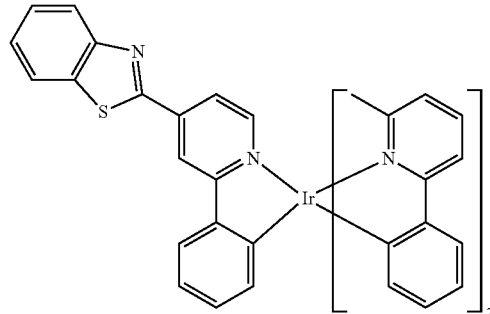
Compound 29
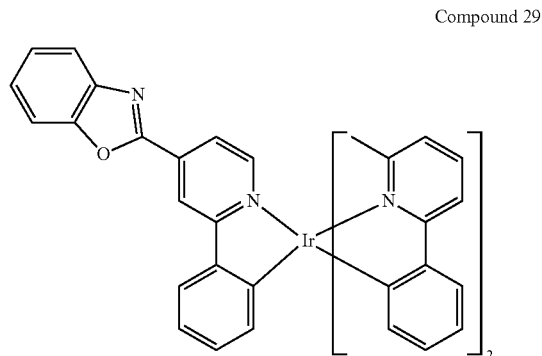
Compound 30
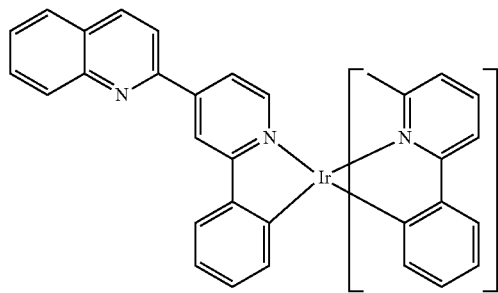
Compound 31
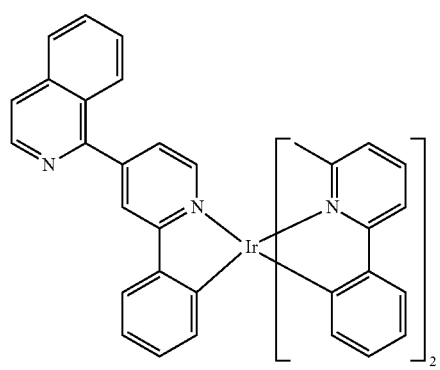

Compound 32

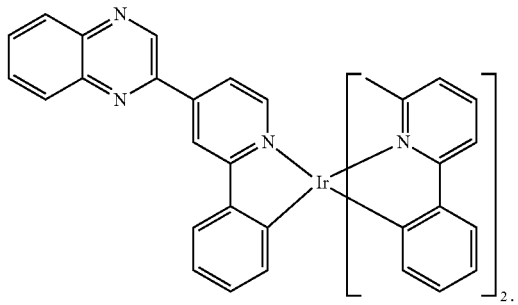

A first device is also provided. The first device comprises an organic light emitting device, further comprising an anode, a cathode, and an organic layer, disposed between the anode and the cathode. The organic layer comprising a first compound having the formula $M(L)_x(L_1)_y(L_2)_z$.

L is

Formula I

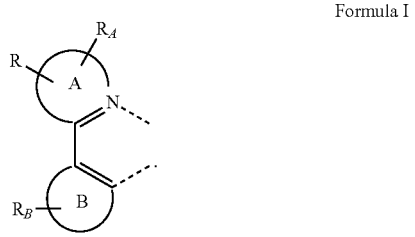

$L_1$ is

Formula II

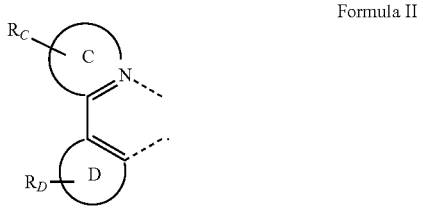

$L_2$ is

Formula III

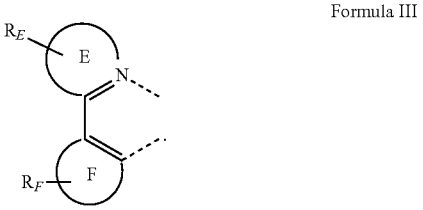

$L_1$ and $L_2$ can be the same or different. M is a metal having an atomic number greater than 40. Preferably, the metal M is Ir. x is 1, 2 or 3. y is 0, 1 or 2. z is 0, 1 or 2. x+y+z is the oxidation state of the metal M. A is a 6-membered heterocyclic ring. B, C, D, E and F are each independently a 5 or 6-membered carbocyclic or heterocyclic ring. Preferably, B is phenyl. R is a 5 or 6-membered heterocyclic ring. Preferably, R is a 5 or 6-membered heterocyclic ring that contains at least one nitrogen atom. R is attached to A at a position para to the metal M. $R_A$, $R_B$, $R_C$, $R_D$, $R_E$ and $R_F$ may represent mono, di, tri, tetra, or penta substitutions. Each of $R_A$, $R_B$, $R_C$, $R_D$, $R_E$ and $R_F$ is independently selected from the group consisting of hydrogen, alkyl, alkoxy, amino, alkenyl, alkynyl, arylkyl, aryl, and heteroaryl. The ligand L is coordinated bidentately to the metal M.

In one aspect, the ligand L has the formula:

Formula IV

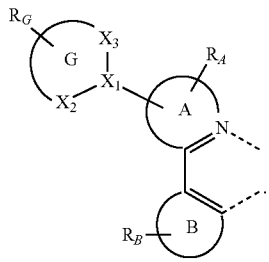

G is a 5 or 6-membered heterocyclic ring. Preferably, G is a 5 or 6-membered heterocyclic ring that contains at least one nitrogen atom. $X_1$, $X_2$, and $X_3$ are independently selected from carbon, oxygen, sulfur and nitrogen. Preferably, $X_1$, $X_2$, and $X_3$ are independently carbon or nitrogen. $R_G$ may represent mono, di, tri, tetra, or penta substitutions. $R_G$ is independently selected from the group consisting of hydrogen, alkyl, alkoxy, amino, alkenyl, alkynyl, arylkyl, aryl, and heteroaryl.

In one aspect, at least one of $X_1$, $X_2$, and $X_3$ is nitrogen. In another aspect, each of $X_1$, $X_2$, and $X_3$ is carbon.

In another aspect, L, $L_1$ and $L_2$ are connected to form a tetradentate ligand and a bidentate ligand or a hexadentate ligand.

In one aspect, the compound is homoleptic. In another aspect, the compound has the formula:

Formula V

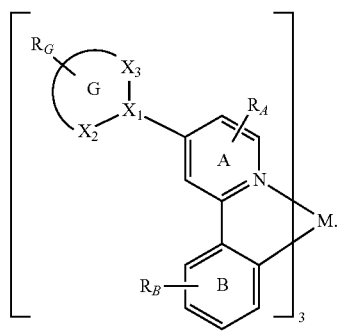

In one aspect, the compound is heteroleptic. In another aspect, the compound has the formula:

Formula VI

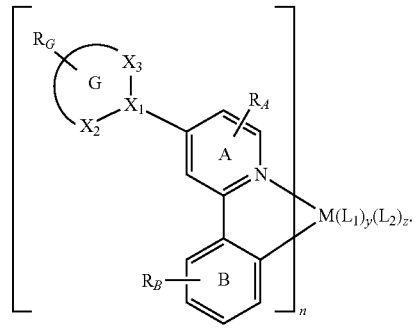

n+y+z is the oxidation state of the metal M. n is at least 1. y is 0, 1 or 2. x is 0, 1, or 2.

In one aspect, the ligand L is selected from the group consisting of:

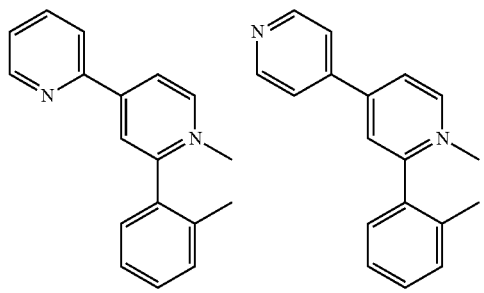

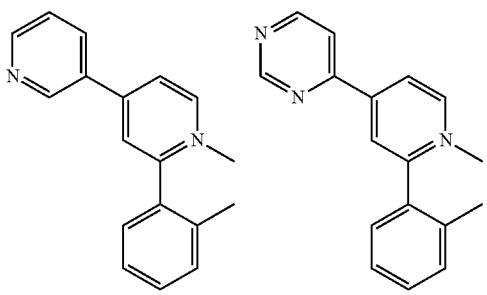

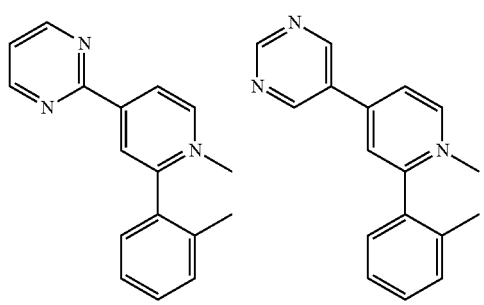

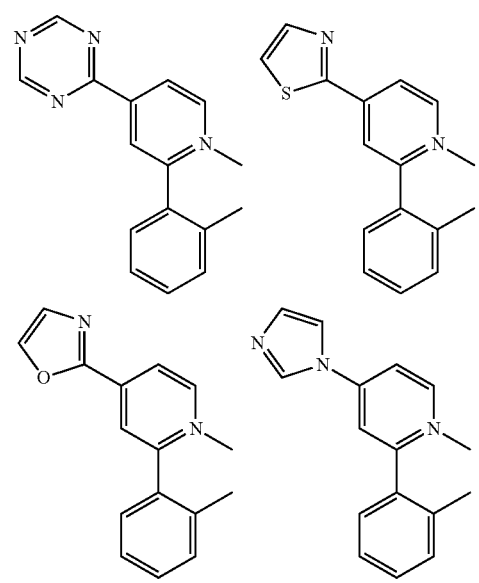

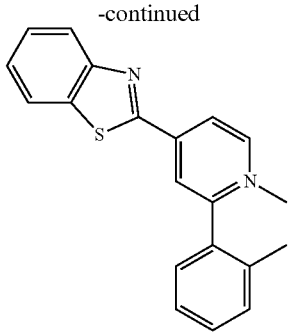

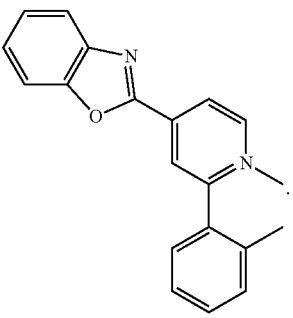

Specific examples of devices containing compounds comprising a phenyl pyridine ligand further substituted with a heterocyclic ring. In particular, the compound is selected from the group consisting of Compound 1-Compound 32.

In one aspect, the organic layer is an emissive layer and the first compound is an emissive compound.

In another aspect, the organic layer further comprises a second emissive compound. Preferably, the second emissive compound is Compound H

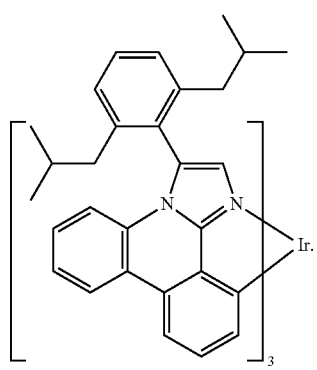

In another aspect, the organic layer further comprises a host having the formula:

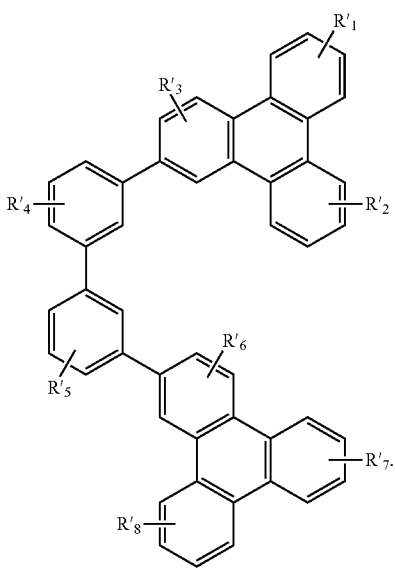

$R'_1$, $R'_2$, $R'_3$, $R'_4$, $R'_5$, $R'_6$, $R'_7$, and $R'_8$ are independently selected from the group consisting of hydrogen, alkyl, alkoxy, amino, alkenyl, alkynyl, arylkyl, aryl, and heteroaryl. Preferably, the host is:

Compound F

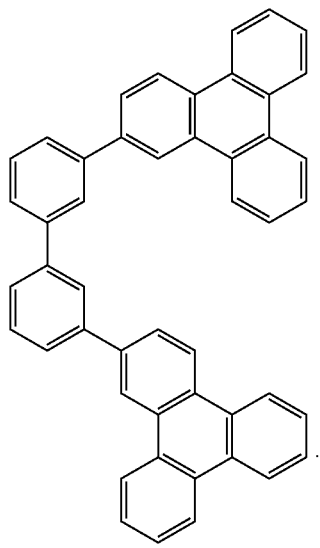

In one aspect, the first device is a consumer product. In another aspect, the first device is an organic light emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
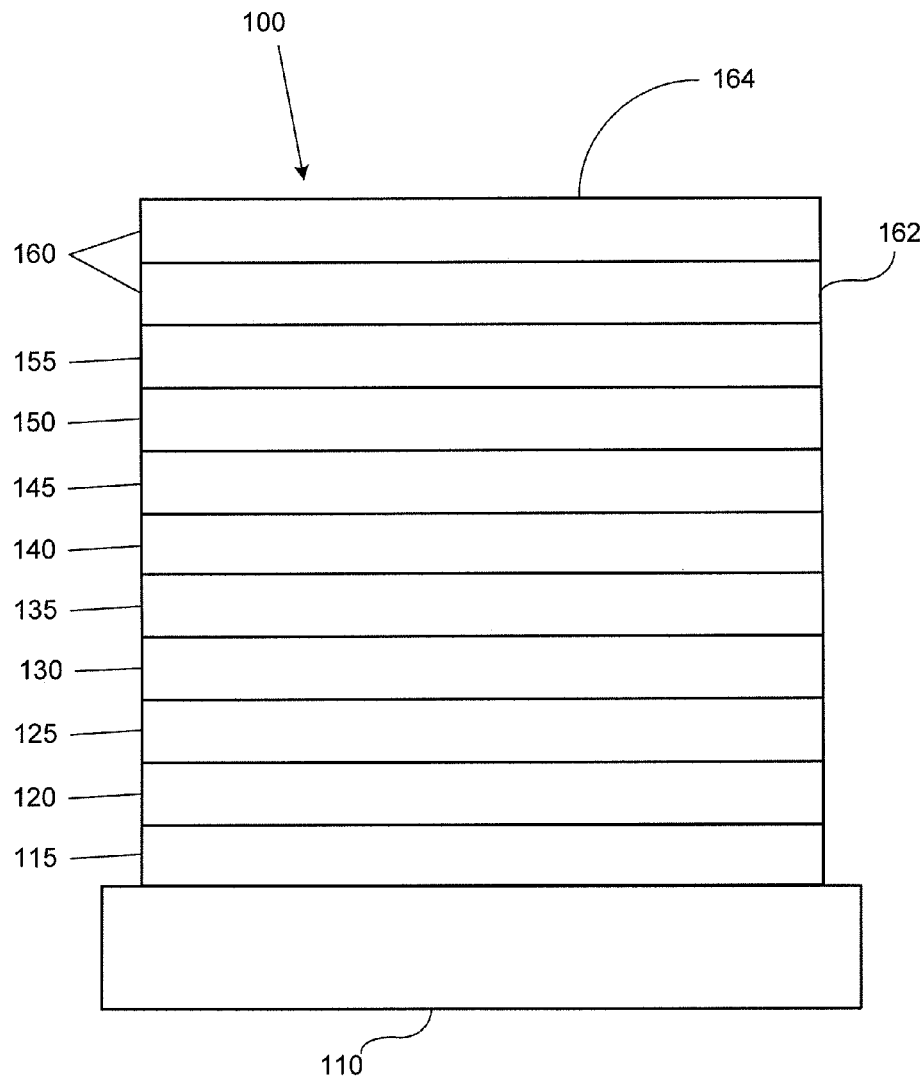
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
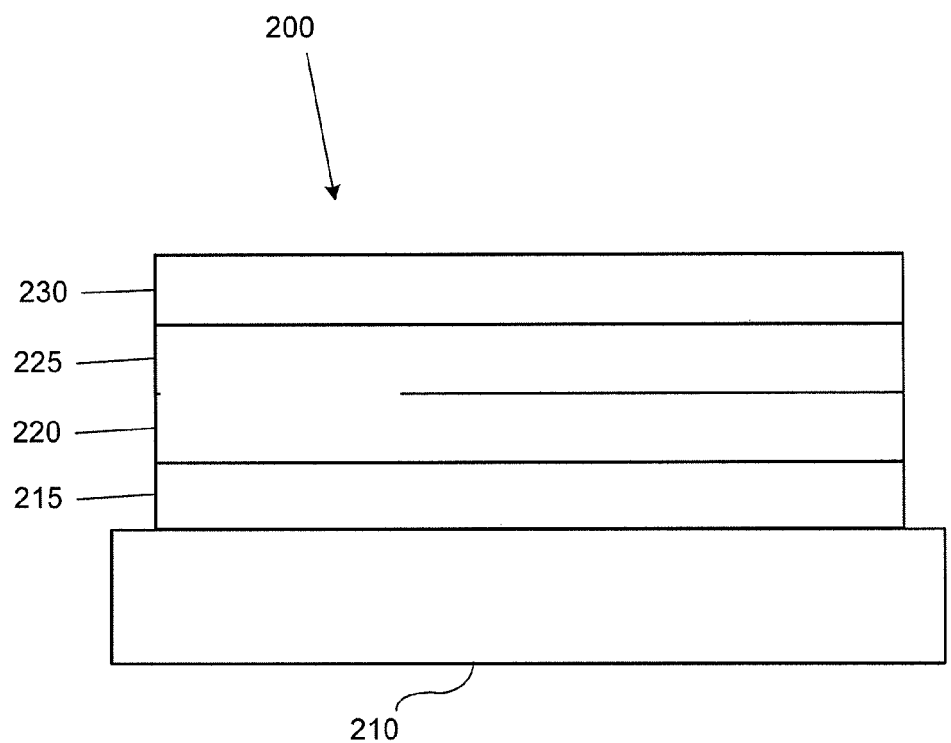
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet deposition (OVJD). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
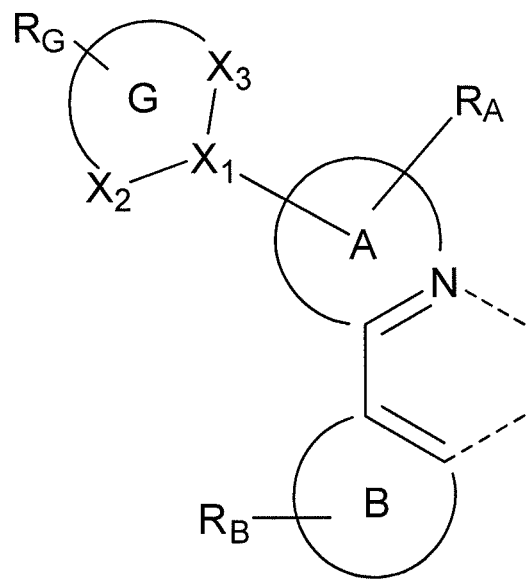
FIG. 3 shows a compound comprising a 2-phenylpyridine ligand further substituted with a heterocyclic group.

Novel compounds containing a phenylpyridine ligand further substituted with a heterocyclic ring are provided. In particular, the heterocyclic ring is attached to the pyridine ring of the 2-phenylpyridine ligand at the position para to the metal, i.e., the 4 position, to which the ligand is coordinated (illustrated in FIG. 3). The compounds may be used as emissive materials for phosphorescent OLEDs. All ligands in the compound are phenylpyridine-based, because these ligands may have higher stability. For example, a compound with all phenylpyridine-based ligands may have higher stability than a compound comprising an acetylacetone, i.e., acac, ligand.

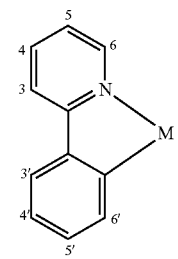

Phenylpyridine and alkyl substituted 2-phenylpyridine ligands have been reported in the literature. In particular, these ligands can bind strongly with iridium(III) to provide good chemical stability. Additionally, the tris complexes of iridium and 2-phenylpyridine ligands may evaporate under high vacuum at low temperatures (i.e., <250° C.). However, the use of these compounds in phosphorescent OLEDs is limited. The operational stability of OLEDs comprising these complexes as the emissive material is poor. Aryl and heterocyclic substitution on 2-phenylpyridine can improve device stability. As reported herein, homoleptic and heteroleptic compounds comprising of at least one ligand with a heterocyclic substituent provide improved devices. In particular, the compounds provided herein may provide high efficiency, high luminous efficiency:quantum efficiency ratio (LE:EQE) and high stability.

Phenyl groups substituted on the pyridine ring of the 2-phenylpyridine ligand may increase the conjugation of the ligand and, in some cases, result in a red shifted emission. This red-shifting effect may be desirable for emission with longer wavelengths (between 540 nm and 560 nm) in the yellow part of the spectrum. Heterocyclic groups substituted on the pyridine ring of the 2-phenylpyridine ligand may also increase the conjugation of the ligand resulting in even further red shifted emission of up to 590 nm. Without being bound by theory, it is believed that the heterocyclic group located at the 4 position of the pyridine ring of the 2-phenylpyridine ligand provides significant red shifting impact and broadens the emission spectra. That is, heterocyclic rings at the 4 position of the 2-phenylpyridine ligand may provide a broad organce spectrum, which may be especially desirable for white devices. In particular, a nitrogen containing heterocycle may be particularly beneficial for color tuning.

These materials can be very useful in certain applications, for example, the development of white OLEDs. Typical white OLEDs can be prepared by using a combination of emissive components with different wavelengths, which when optimized can produce white light. White OLEDs can typically be prepared by using a combination of 3 emissive components. In particular, a combination of blue, green and red emissive components can be used to generate white light. For manufacturing purposes, it is most desirable to incorporate a minimum number of materials into a device. Therefore, white OLEDs containing only two emissive components are highly desirable.

Generating a commercial device using two emissive components to generate white light is far more challenging than generating a commercial device using three components. Emitters with more specific colors are required. Without being bound by theory, it is believed that the compounds provided herein emit in an energy range suitable for use in two emitting component white devices. In addition, these compounds can also be used in a three emitting component white device.

Heterocyclic groups substituted at the 4 position on the pyridine ring of the 2-phenylpyridine not only provides the optimum desired color but in addition the ligand may also lower and stabilize the LUMO of the metal complex, thereby providing further device operational stability. The homoleptic and heteroleptic compounds provided herein comprise at least one 2-phenylpyridine ligand with a heterocyclic substituent attached to the pyridine para to the metal, i.e., the 4 position. These ligands result in a stabilized LUMO and red shifted emission of the metal complex. Therefore, the compounds provided herein may have emission energies red shifted from the target range of phenyl substituted or unsubstituted counterparts, i.e., 550 nm and 600 nm.

The compounds provided herein may provide devices having high efficiency, high stability and improved processiblity. These compounds are suitable for both monochrome displays and white devices for displays, medical backlight and lighting.

Compounds having the formula $M(L)_x(L_1)_y(L_2)_z$ are provided.

L is

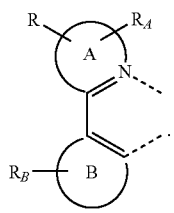

Formula I $L_1$ is

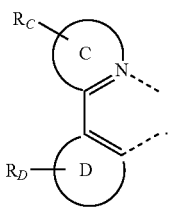

Formula II $L_2$ is

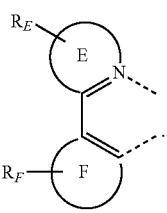

Formula III $L_1$ and $L_2$ can be the same or different. M is a metal having an atomic number greater than 40. Preferably, the metal M is Ir. x is 1, 2 or 3. y is 0, 1 or 2. z is 0, 1 or 2. x+y+z is the oxidation state of the metal M. A is a 6-membered heterocyclic ring. B, C, D, E and F are each independently a 5 or 6-membered carbocyclic or heterocyclic ring. Preferably, B is phenyl. R is a 5 or 6-membered heterocyclic ring. R is attached to A at a position para to the metal M. $R_A$, $R_B$, $R_C$, $R_D$, $R_E$ and $R_F$ may represent mono, di, tri, tetra, or penta substitutions. Each of $R_A$, $R_B$, $R_C$, $R_D$, $R_E$ and $R_F$ is independently selected from the group consisting of hydrogen, alkyl, alkoxy, amino, alkenyl, alkynyl, arylkyl, aryl, and heteroaryl. The ligand L is coordinated bidentately to the metal M. R is a 5 or 6-membered heterocyclic ring that contains at least one nitrogen atom.

In one aspect, the ligand L has the formula:

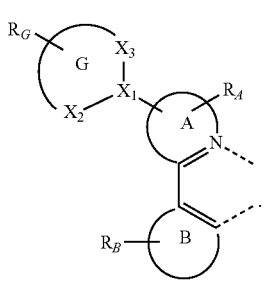

Formula IV

G is a 5 or 6-membered heterocyclic ring. Preferably, G is a 5 or 6-membered heterocyclic ring that contains at least one nitrogen atom. $X_1$, $X_2$, and $X_3$ are independently selected from carbon, oxygen, sulfur and nitrogen. Preferably, $X_1$, $X_2$, and $X_3$ are independently carbon or nitrogen. $R_G$ may represent mono, di, tri, tetra, or penta substitutions. $R_G$ is independently selected from the group consisting of hydrogen, alkyl, alkoxy, amino, alkenyl, alkynyl, arylkyl, aryl, and heteroaryl.

In one aspect, at least one of $X_1$, $X_2$, and $X_3$ is nitrogen. In another aspect, each of $X_1$, $X_2$, and $X_3$ is carbon.

In another aspect, L, $L_1$ and $L_2$ are connected to form a tetradentate ligand and a bidentate ligand or a hexadentate ligand. For example, L and $L_1$ may be connected to form a tetradentate ligand and $L_2$ is a bidentate ligand. Similarly, L and $L_2$ or $L_1$ and $L_2$ may be connected to form a tetradentate ligand while $L_1$ or L is a bidentate ligand. Additionally, L, $L_1$ and $L_2$ may all be connected to form a hexadentate ligand.

In one aspect, the compound is homoleptic. In another aspect, the compound has the formula:

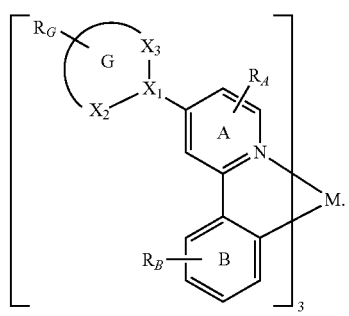

Formula V

In one aspect, the compound is heteroleptic. In another aspect, the compound has the formula:

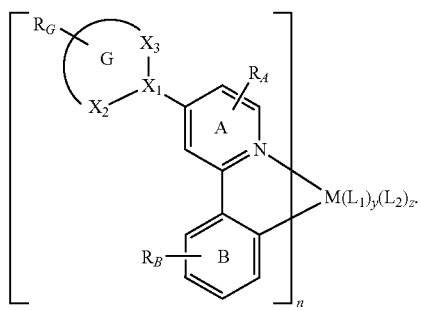

Formula VI n+y+z is the oxidation state of the metal M. n is at least 1. y is 0, 1 or 2. x is 0, 1, or 2.

In one aspect, the ligand L is selected from the group consisting of:

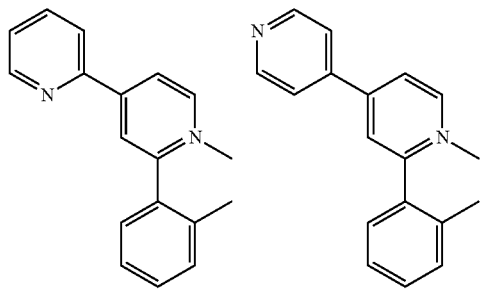

-continued

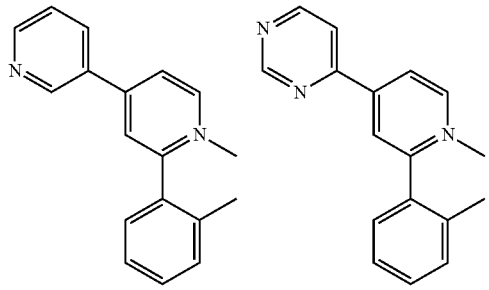

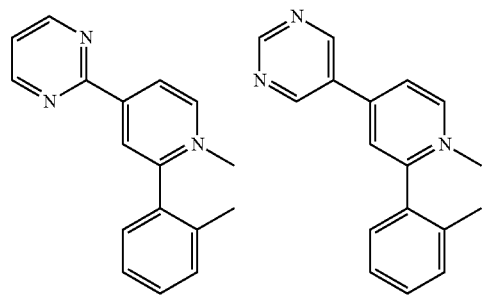

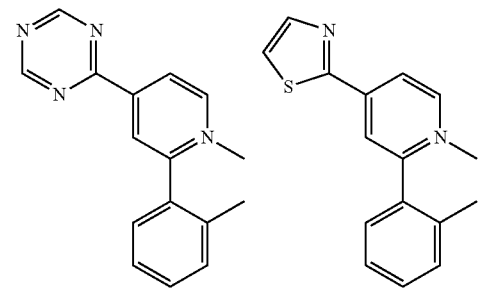

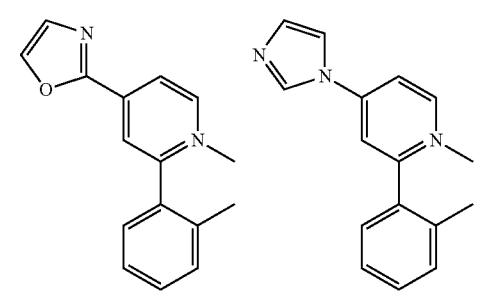

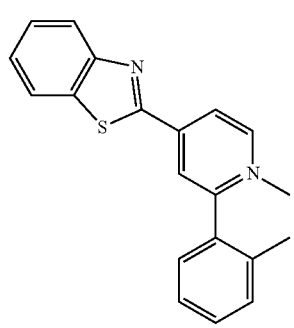

-continued
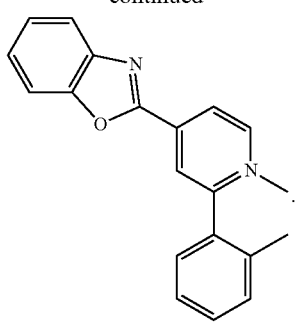
Specific examples of compounds comprising a phenyl pyridine ligand further substituted with a heterocyclic ring are also provided. In particular, the compound is selected from the group consisting of:
Compound 1
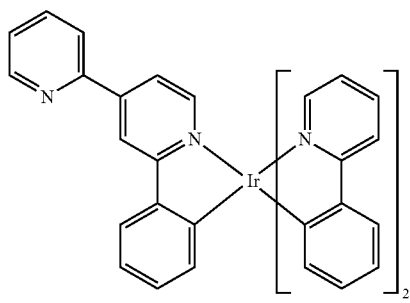
Compound 2
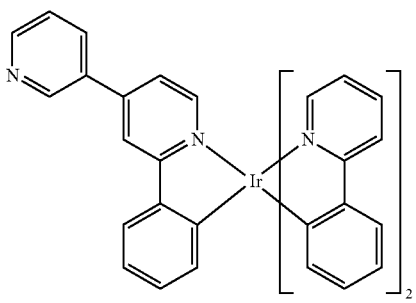
Compound 3
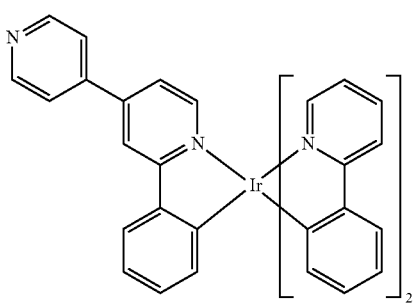
Compound 4
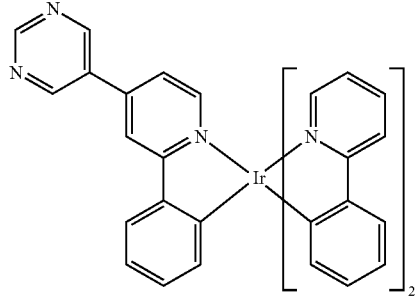
Compound 5
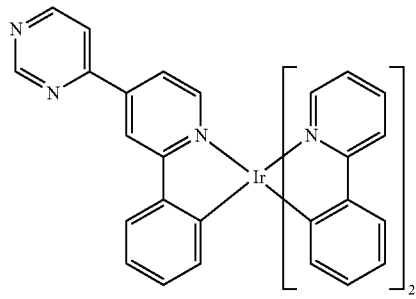
Compound 6
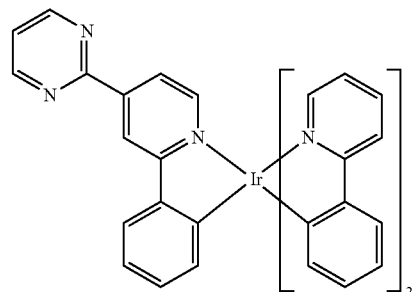
Compound 7
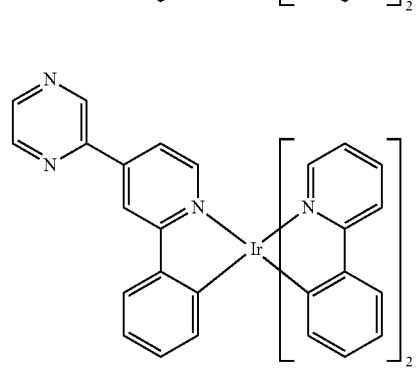
Compound 8
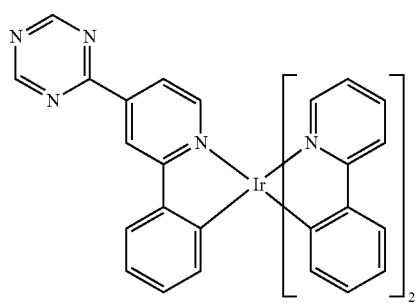

Compound 9
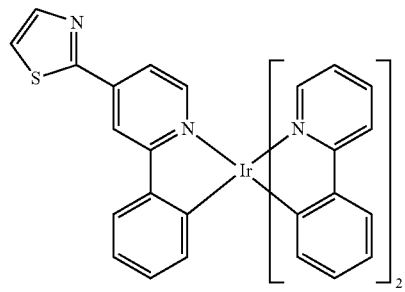
Compound 10
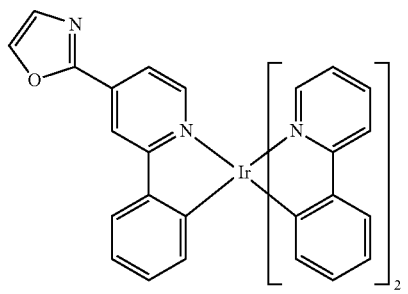
Compound 11
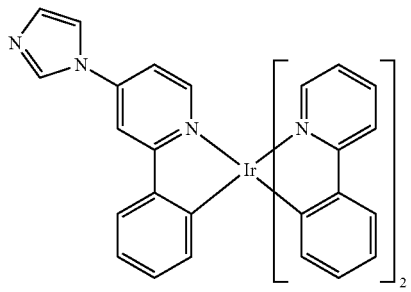
Compound 12
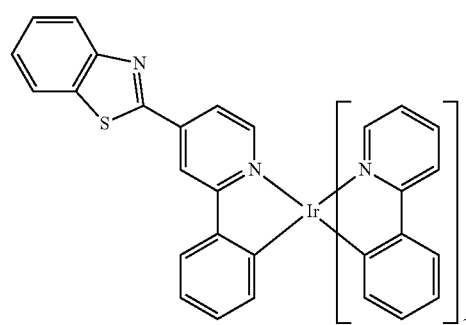
Compound 13
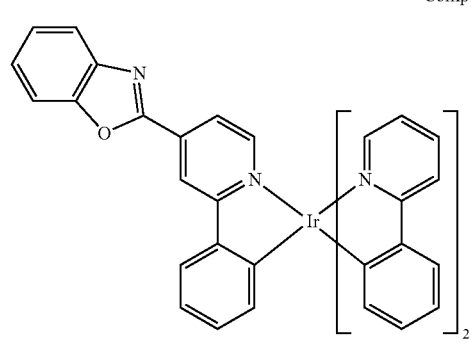
Compound 14
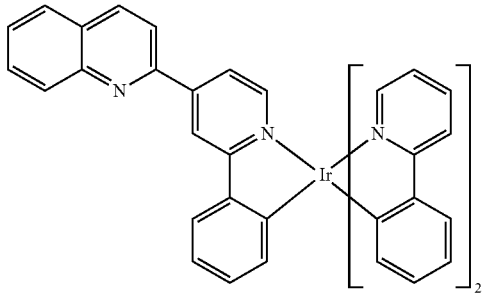
Compound 15
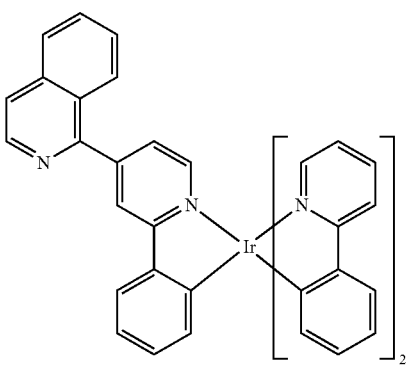
Compound 16
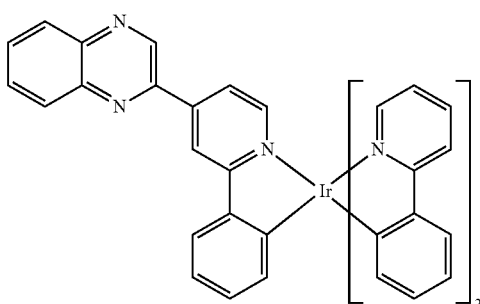
Compound 17
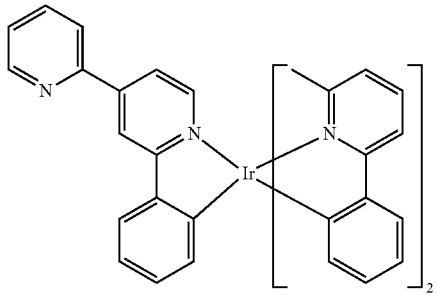

Compound 18
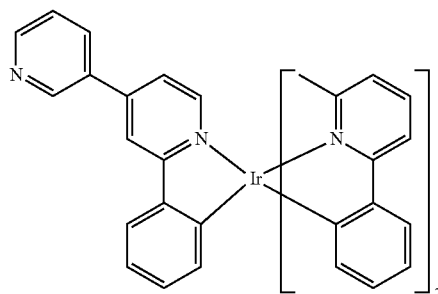
Compound 19
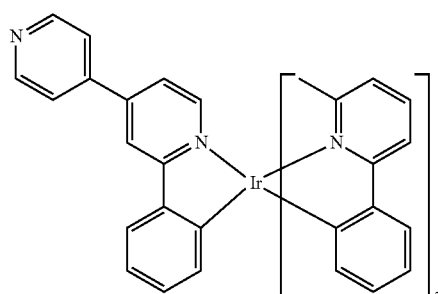
Compound 20
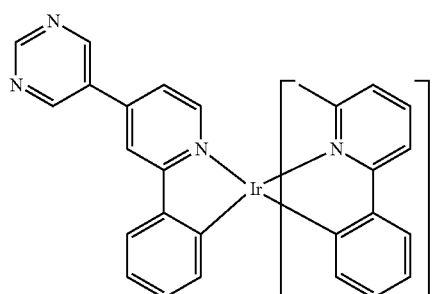
Compound 21
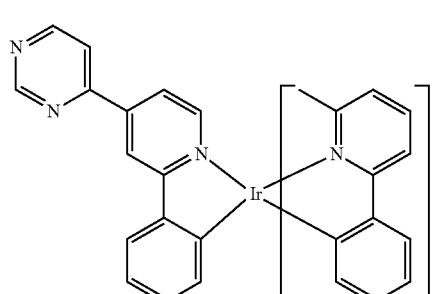
Compound 22
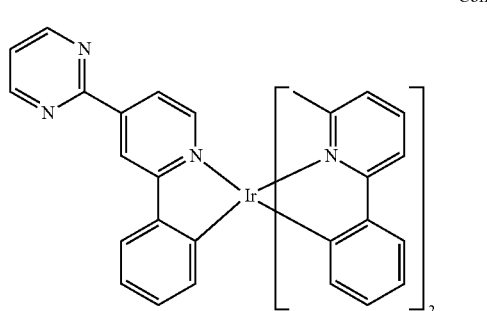
Compound 23
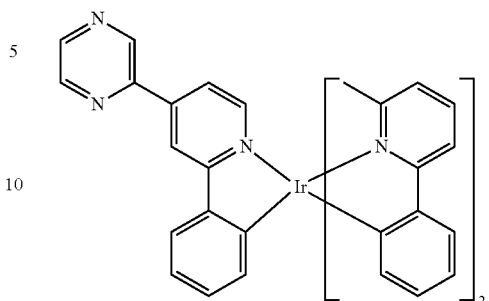
Compound 24
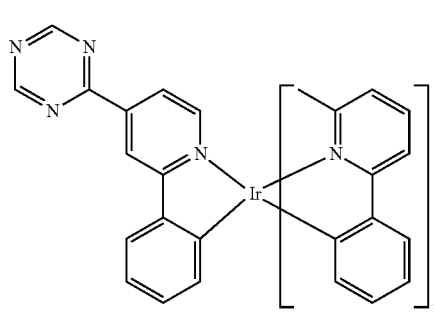
Compound 25
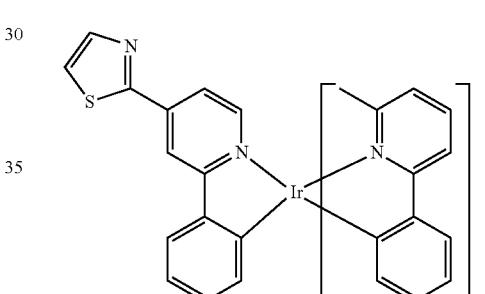
Compound 26
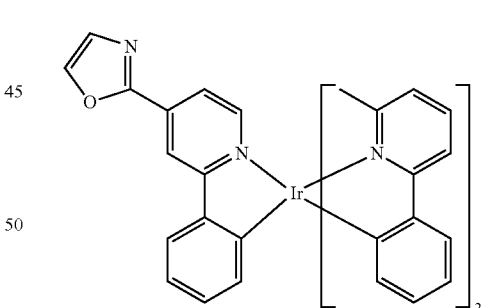
Compound 27
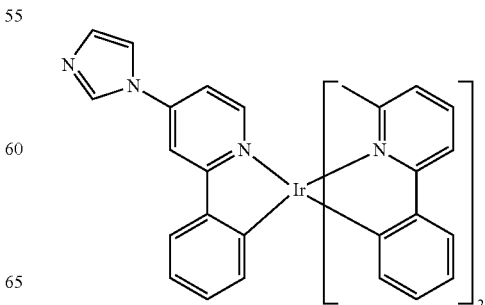

Compound 28

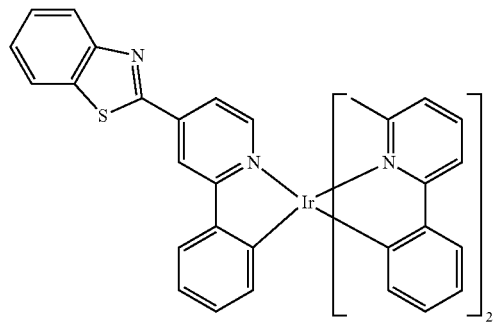

Compound 29

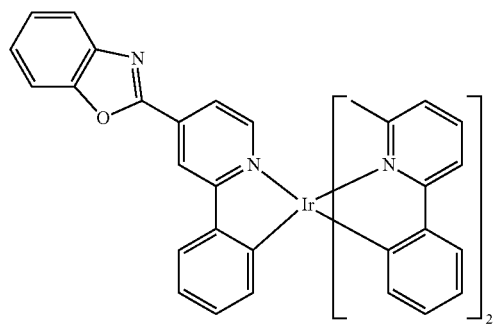

Compound 30

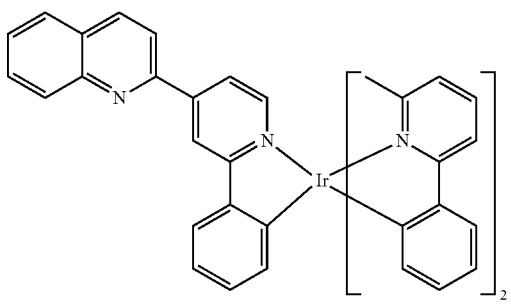

Compound 31

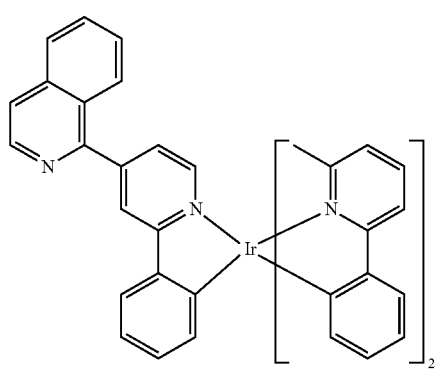

Compound 32

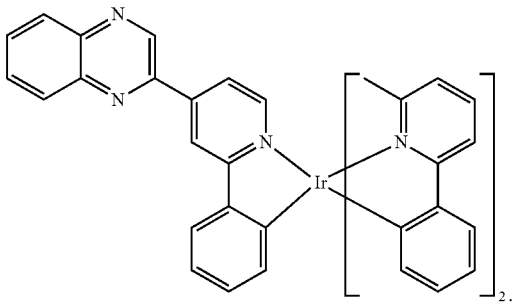

A first device is also provided. The first device comprises an organic light emitting device, further comprising an anode, a cathode, and an organic layer, disposed between the anode and the cathode. The organic layer comprising a first compound having the formula $M(L)_x(L_1)_y(L_2)_z$.

L is

Formula I

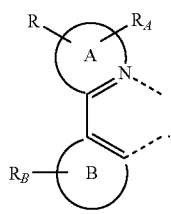

$L_1$ is

Formula II

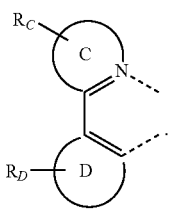

$L_2$ is

Formula III

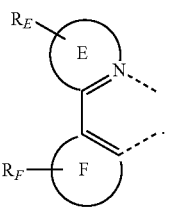

$L_1$ and $L_2$ can be the same or different. M is a metal having an atomic number greater than 40. Preferably, the metal M is Ir. x is 1, 2 or 3. y is 0, 1 or 2. z is 0, 1 or 2. x+y+z is the oxidation state of the metal M. A is a 6-membered heterocyclic ring. B, C, D, E and F are each independently a 5 or 6-membered carbocyclic or heterocyclic ring. Preferably, B is phenyl. R is a 5 or 6-membered heterocyclic ring. Preferably, R is a 5 or 6-membered heterocyclic ring that contains at least one nitrogen atom. R is attached to A at a position para to the metal M. $R_A$, $R_B$, $R_C$, $R_D$, $R_E$ and $R_F$ may represent mono, di, tri, tetra, or penta substitutions. Each of $R_A$, $R_B$, $R_C$, $R_D$, $R_E$ and $R_F$ is independently selected from the group consisting of hydrogen, alkyl, alkoxy, amino, alkenyl, alkynyl, arylkyl, aryl, and heteroaryl. The ligand L is coordinated bidentately to the metal M.

In one aspect, the ligand L has the formula:

Formula IV

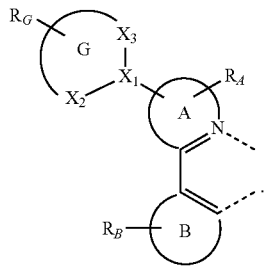

G is a 5 or 6-membered heterocyclic ring. Preferably, G is a 5 or 6-membered heterocyclic ring that contains at least one nitrogen atom. $X_1$, $X_2$, and $X_3$ are independently selected from carbon, oxygen, sulfur and nitrogen. Preferably, $X_1$, $X_2$, and $X_3$ are independently carbon or nitrogen. $R_G$ may represent mono, di, tri, tetra, or penta substitutions. $R_G$ is independently selected from the group consisting of hydrogen, alkyl, alkoxy, amino, alkenyl, alkynyl, arylkyl, aryl, and heteroaryl.

In one aspect, at least one of $X_1$, $X_2$, and $X_3$ is nitrogen. In another aspect, each of $X_1$, $X_2$, and $X_3$ is carbon.

In another aspect, L, $L_1$ and $L_2$ are connected to form a tetradentate ligand and a bidentate ligand or a hexadentate ligand.

In one aspect, the compound is homoleptic. In another aspect, the compound has the formula:

Formula V

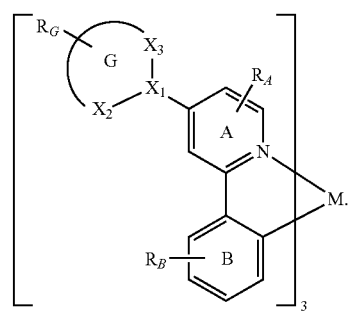

In one aspect, the compound is heteroleptic. In another aspect, the compound has the formula:

Formula VI

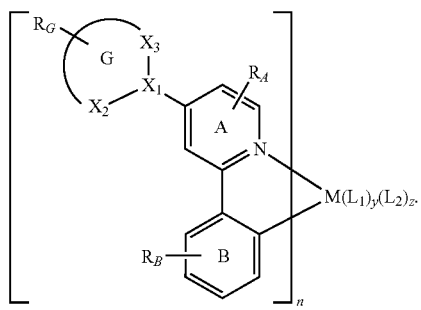

n+y+z is the oxidation state of the metal M. n is at least 1. y is 0, 1 or 2. x is 0, 1, or 2.

In one aspect, the ligand L is selected from the group consisting of:

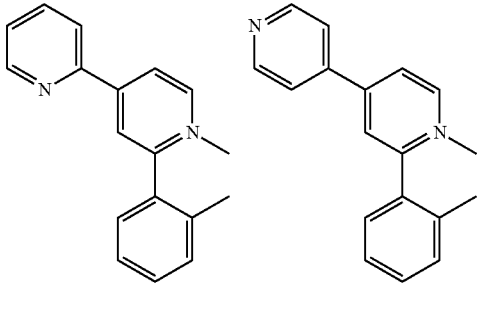

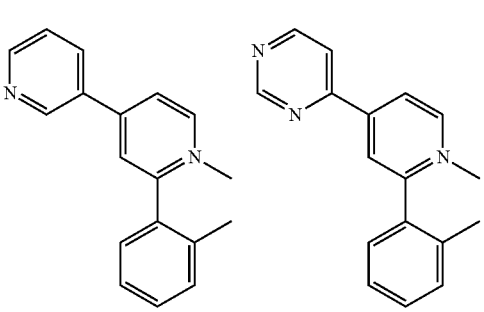

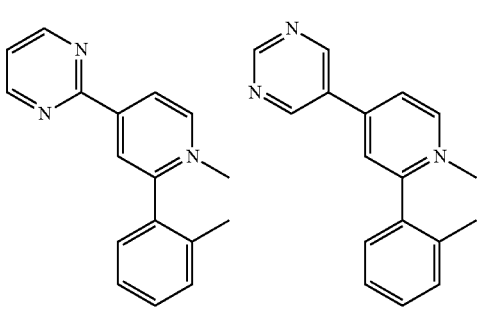

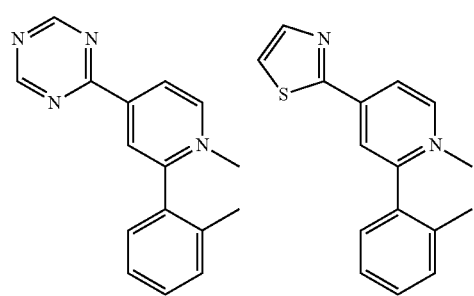

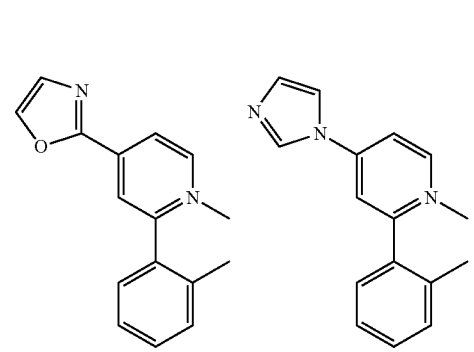

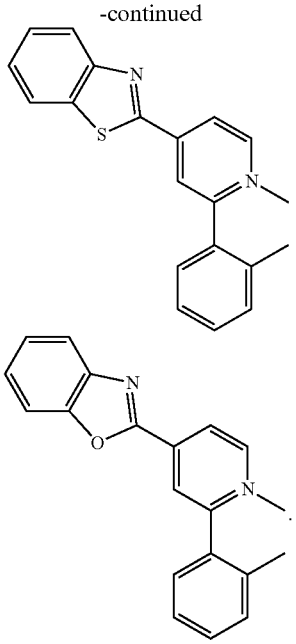
Specific examples of devices containing compounds comprising a phenyl pyridine ligand further substituted with a heterocyclic ring. In particular, the compound is selected from the group consisting of:
Compound 1
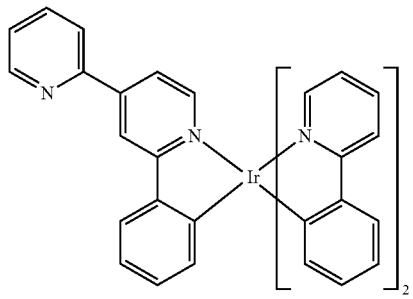
Compound 2
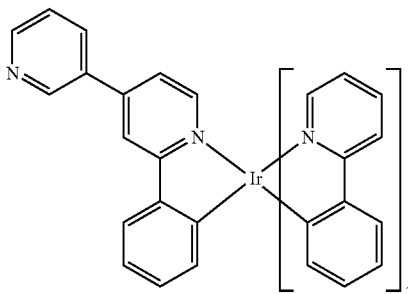
Compound 3
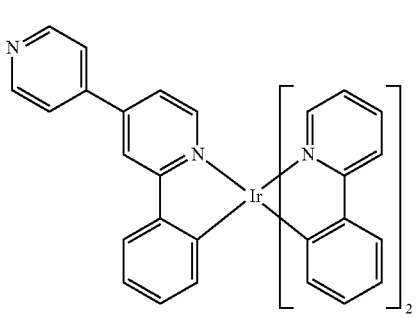
Compound 4
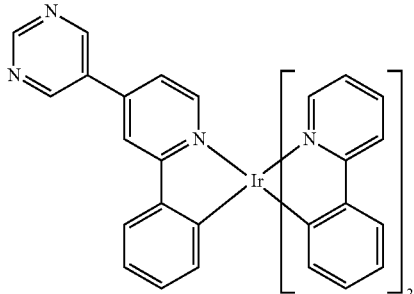
Compound 5
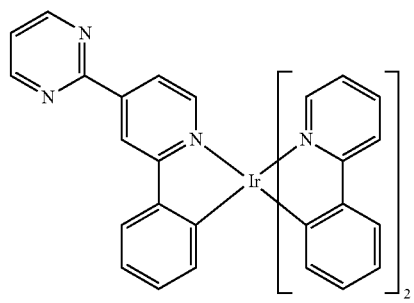
Compound 6
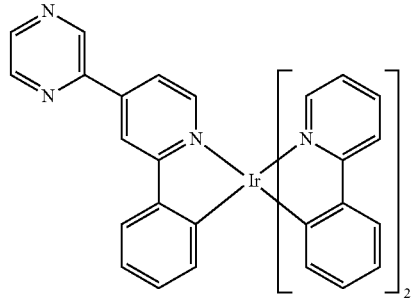
Compound 7
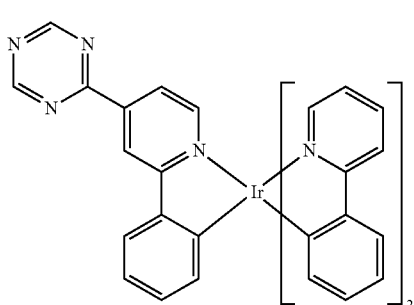
Compound 8

Compound 9
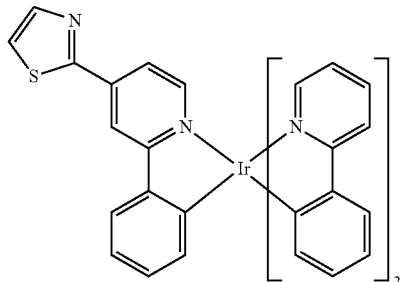
Compound 10
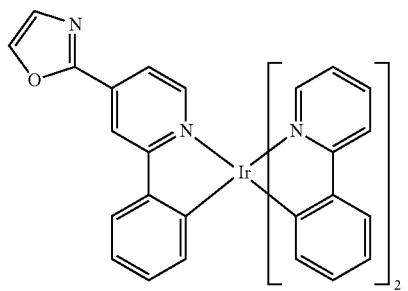
Compound 11
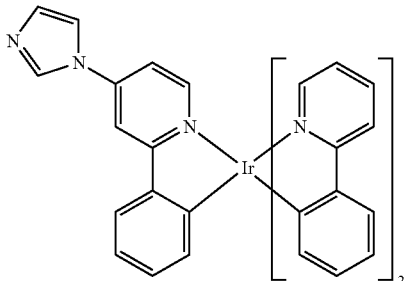
Compound 12
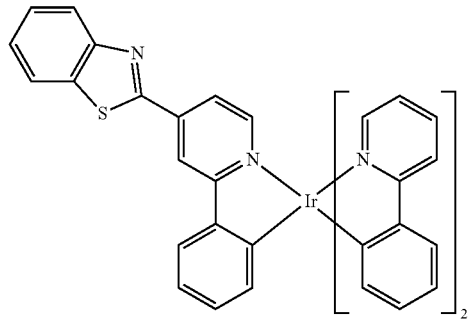
Compound 13
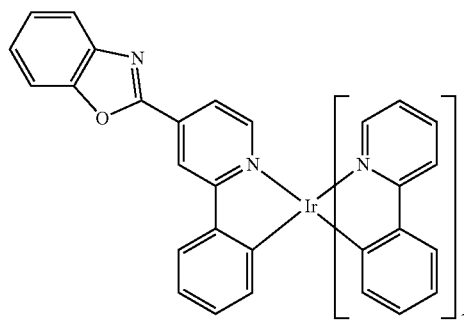
Compound 14
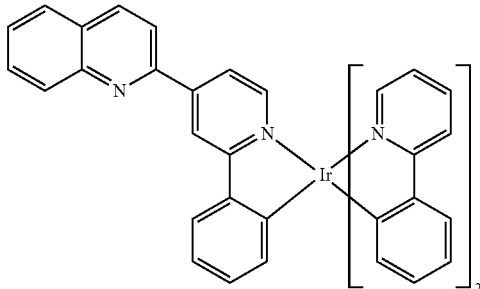
Compound 15
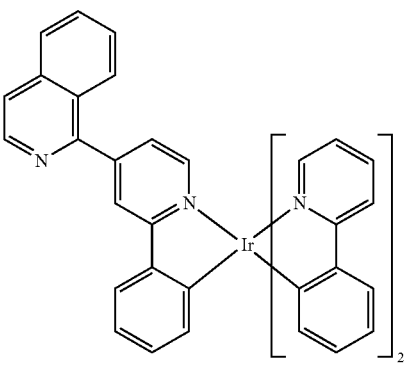
Compound 16
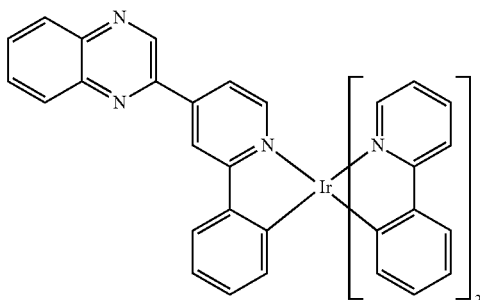
Compound 17
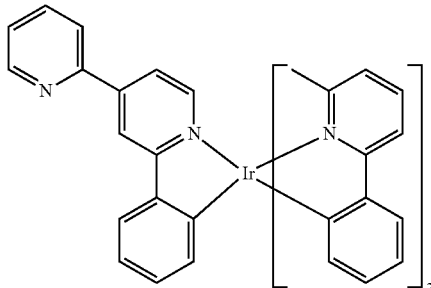

Compound 18
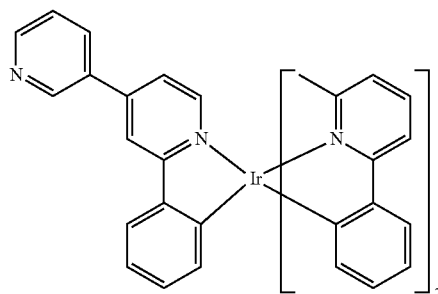
Compound 19
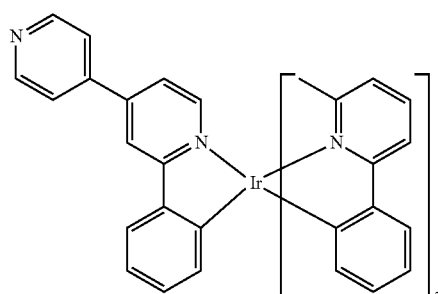
Compound 20
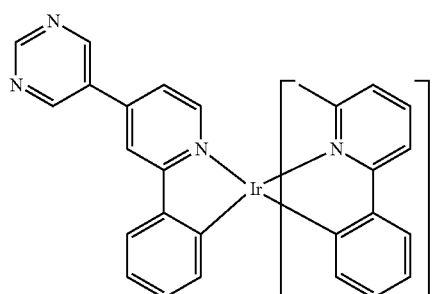
Compound 21
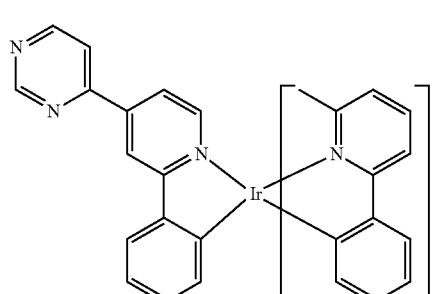
Compound 22
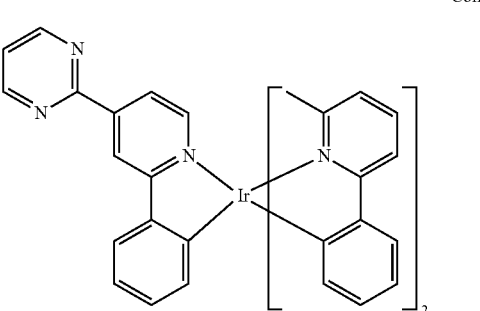
Compound 23
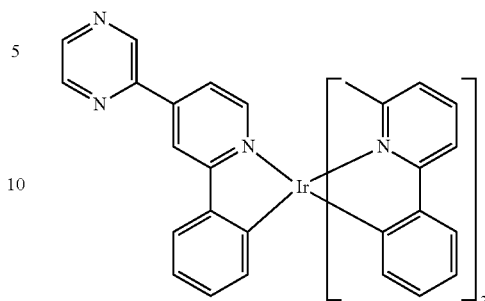
Compound 24
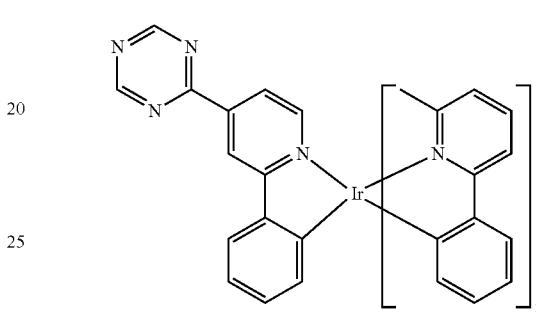
Compound 25
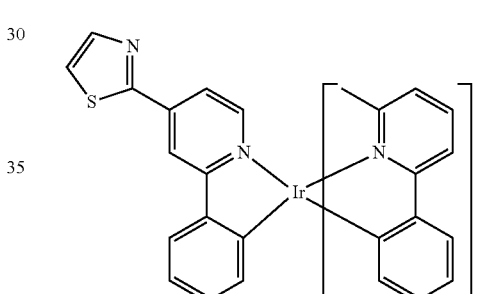
Compound 26
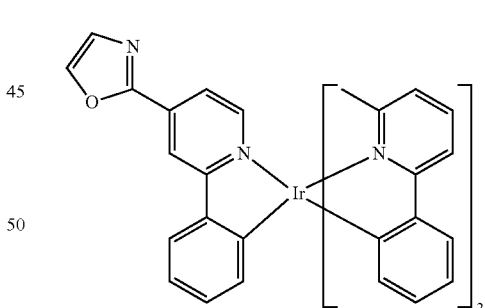
Compound 27
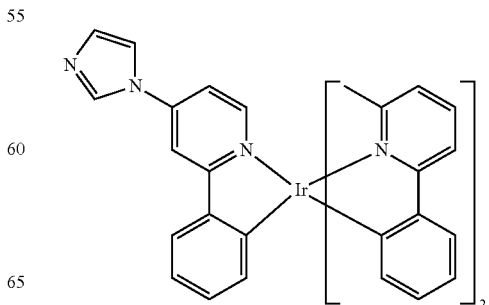

Compound 28

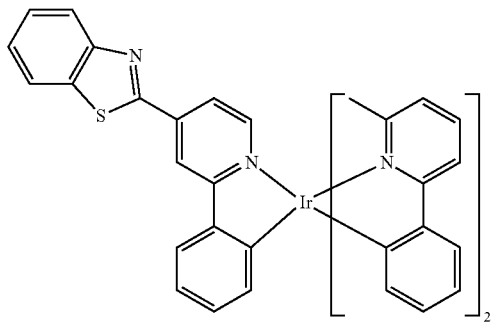

Compound 29

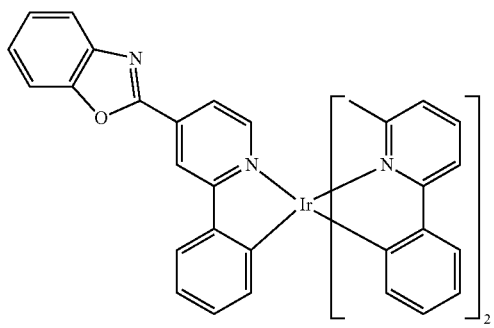

Compound 30

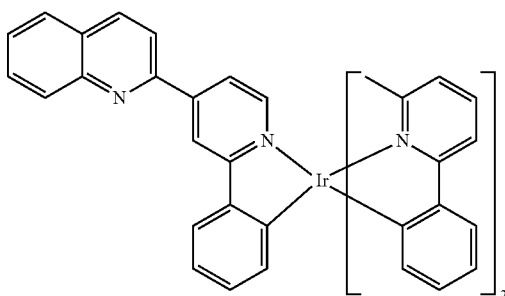

Compound 31

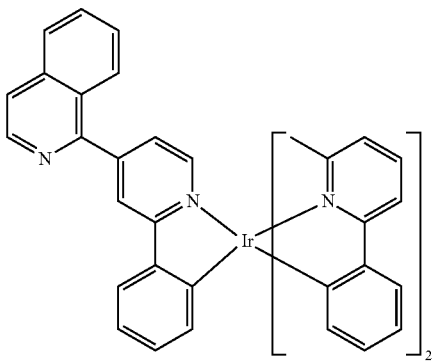

Compound 32

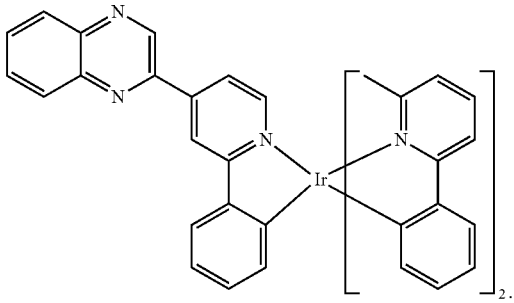

In one aspect, the organic layer is an emissive layer and the first compound is an emissive compound.

In another aspect, the organic layer further comprises a second emissive compound. Preferably, the second emissive compound is Compound H

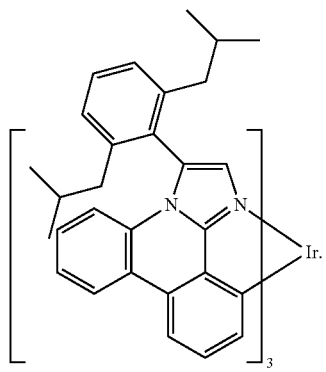

In another aspect, the organic layer further comprises a host having the formula:

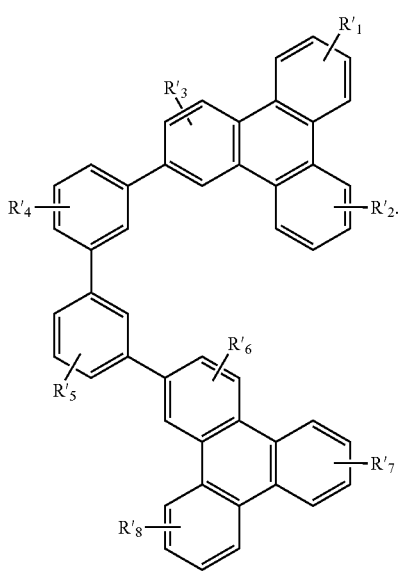

$R'_1$, $R'_2$, $R'_3$, $R'_4$, $R'_5$, $R'_6$, $R'_7$, and $R'_8$ are independently selected from the group consisting of hydrogen, alkyl, alkoxy, amino, alkenyl, alkynyl, arylkyl, aryl, and heteroaryl. Preferably, the host is:

Compound F

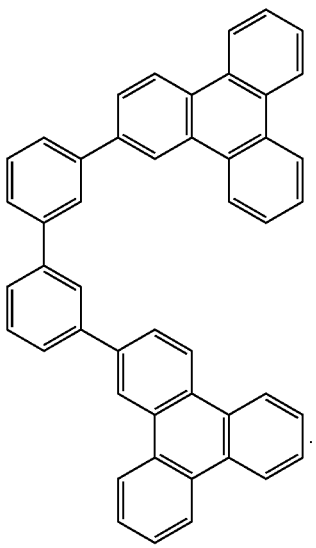

In one aspect, the first device is a consumer product. In another aspect, the first device is an organic light emitting device.

In addition, there are several other embodiments. However, these additional embodiments are less preferred.

Compounds comprising a 2-phenylpyridine ligand further substituted with a heterocyclic ring are provided. The compounds comprise a ligand L having the formula:

Formula VII

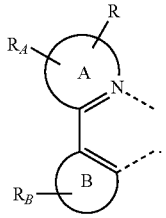

A and B are each independently a 5 or 6-membered carbocyclic or heterocyclic ring. Preferably, B is phenyl. R is a 5 or 6-membered heterocyclic ring. Preferably, R is a 5 or 6-membered heterocyclic ring that contains at least one nitrogen atom. $R_A$ and $R_B$ may represent mono, di, tri, tetra, or penta substitutions. $R_A$ and $R_B$ is independently selected from the group consisting of hydrogen, alkyl, alkoxy, amino, alkenyl, alkynyl, arylkyl, aryl, and heteroaryl. The ligand L is coordinated to a metal M having an atomic number greater than 40. Preferably, the metal M is Ir.

In one aspect, the compounds have the formula $M(L)_x(L_1)_y(L_2)_z$.

L is

Formula VIII

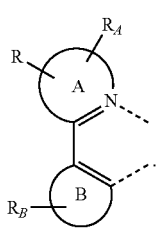

$L_1$ is

Formula IX

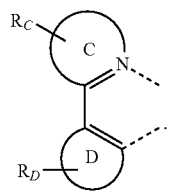

$L_2$ is

Formula X

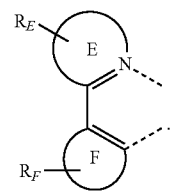

$L_1$ and $L_2$ can be the same or different. x is 1, 2 or 3, y is 0, 1 or 2, z is 0, 1 or 2. x+y+z is the oxidation state of the metal M. A, B, C, D, E and F are each independently a 5 or 6-membered carbocyclic or heterocyclic ring. R is a 5 or 6-membered heterocyclic ring. $R_A$, $R_B$, $R_C$, $R_D$, $R_E$ and $R_F$ may represent mono, di, tri, tetra, or penta substitutions. Each of $R_A$, $R_B$, $R_C$, $R_D$, $R_E$ and $R_F$ is independently selected from the group consisting of hydrogen, alkyl, alkoxy, amino, alkenyl, alkynyl, arylkyl, aryl, and heteroaryl. The ligand L is coordinated bidentately to a metal M having an atomic number greater than 40.

In one aspect, the compound is homoleptic. In a particular aspect, the compound has the formula:

Formula XI

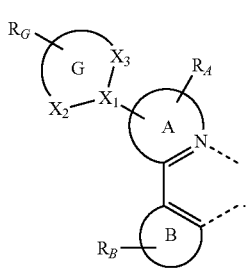

In another aspect, the compound has a formula selected from the group consisting of:

Formula XII

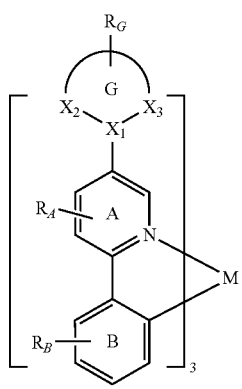

Formula XIII

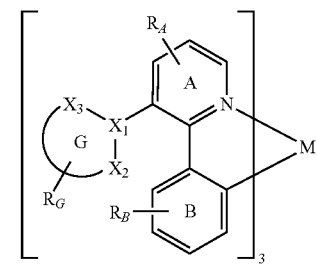

Formula XIV

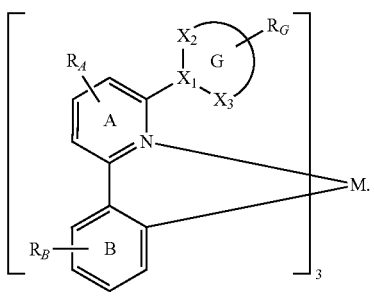

In one aspect, the compound is heteroleptic. In a particular aspect, the compound has the formula:

Formula XV

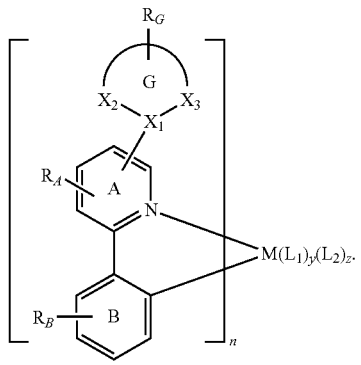

n+y+z is the oxidation state of the metal M. n is at least 1. y is 0, 1 or 2. x is 0, 1, or 2.

In another aspect, the compound has a formula selected from the group consisting of:

Formula XVI

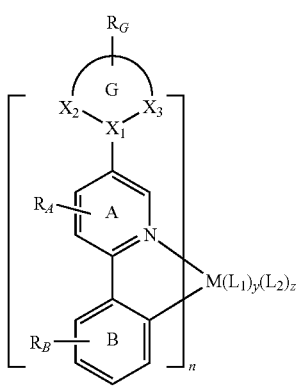

Formula XVII

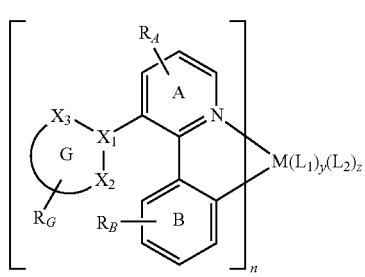

Formula XVIII

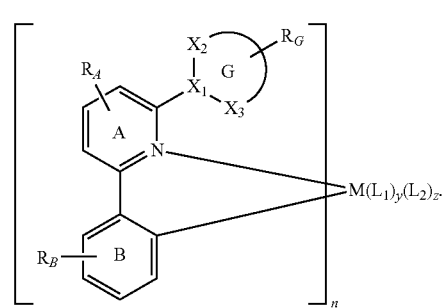

In one aspect, the ligand L is selected from the group consisting of:

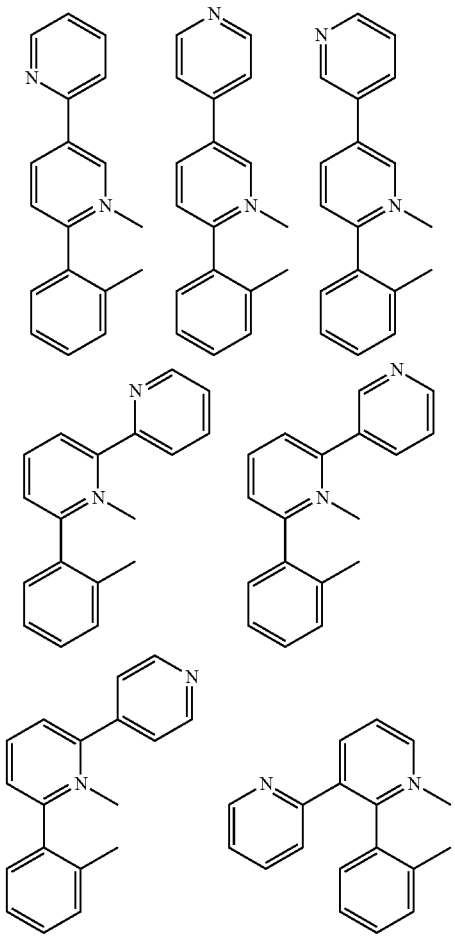

-continued
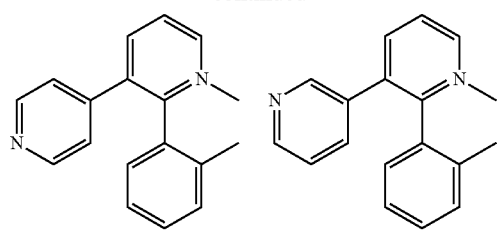
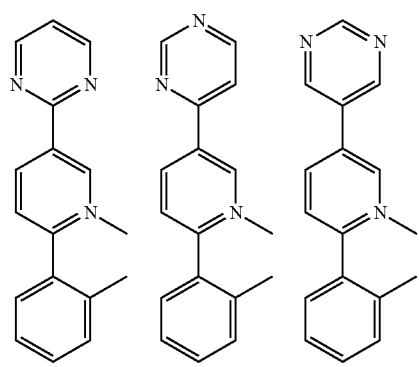
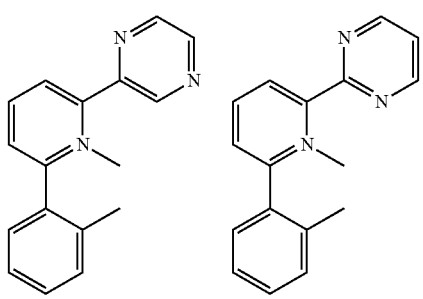
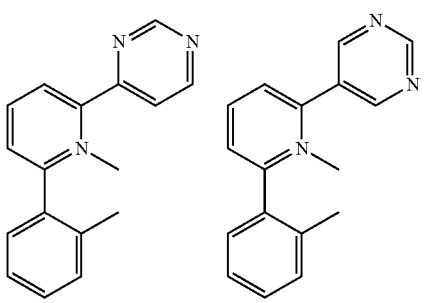
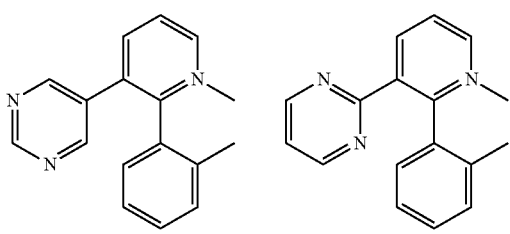
-continued
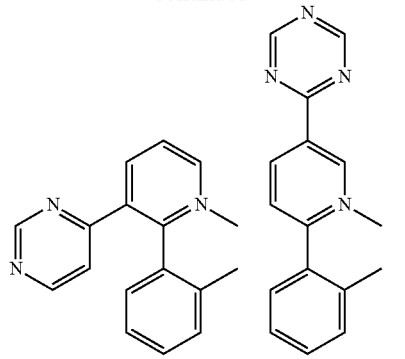
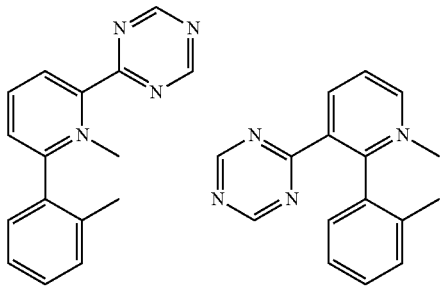
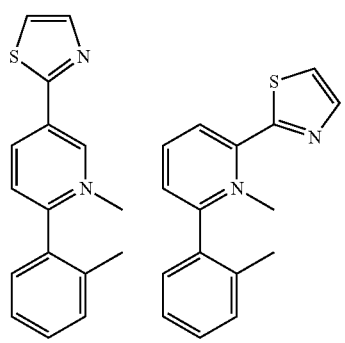
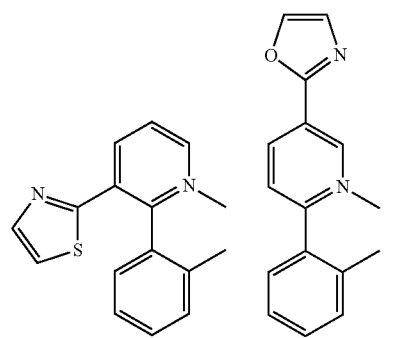
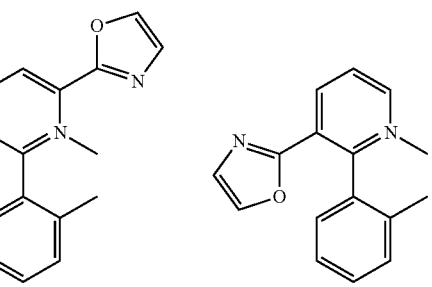

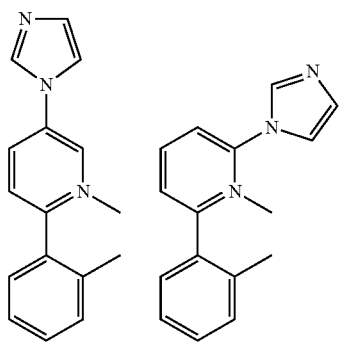
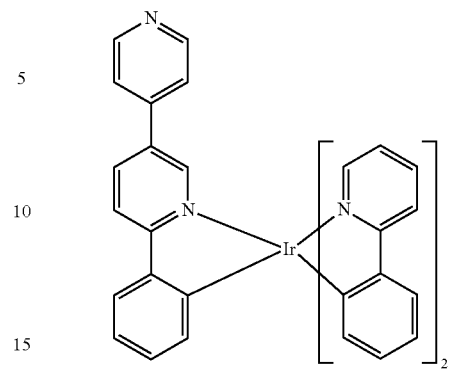
Compound 35
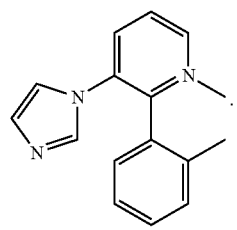
Specific examples of compounds comprising a phenyl pyridine ligand further substituted with a heterocyclic ring are also provided. In particular, the compound is selected from the group consisting of:
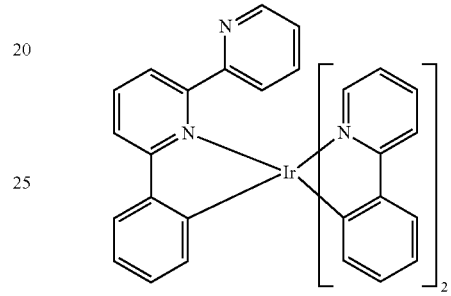
Compound 36
Compound 33
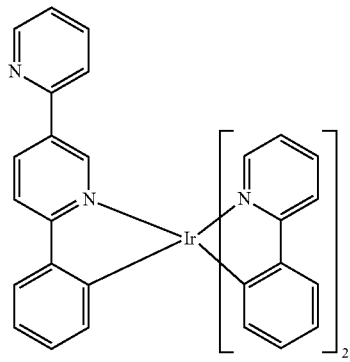
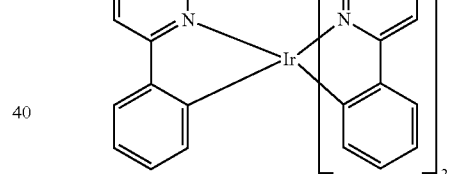
Compound 37
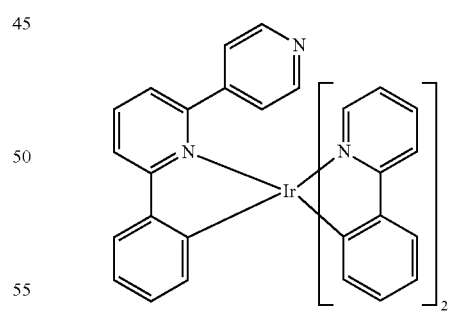
Compound 38
Compound 34
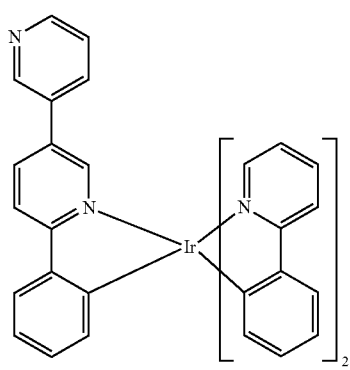
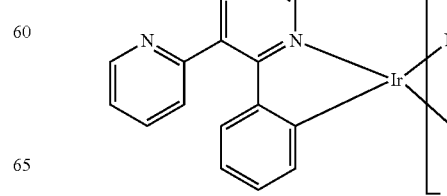
Compound 39

Compound 40
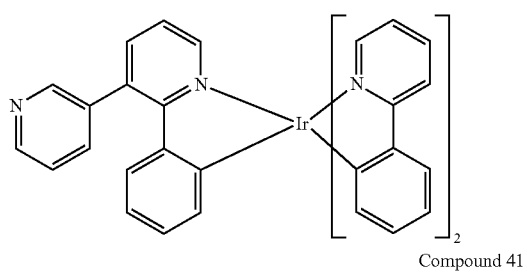
Compound 41
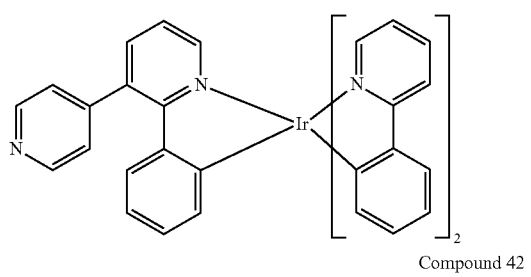
Compound 42
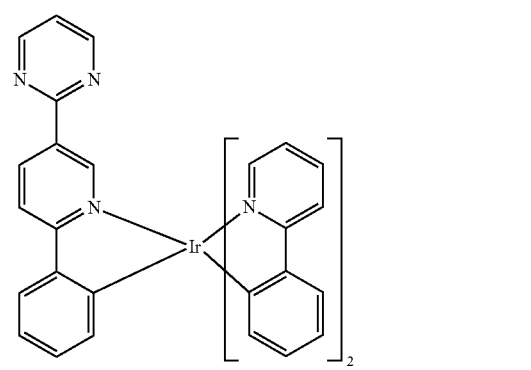
Compound 43
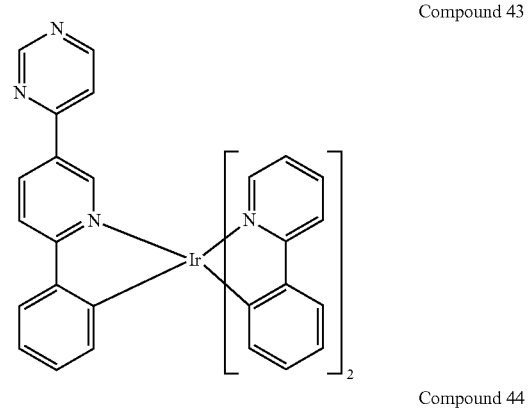
Compound 44
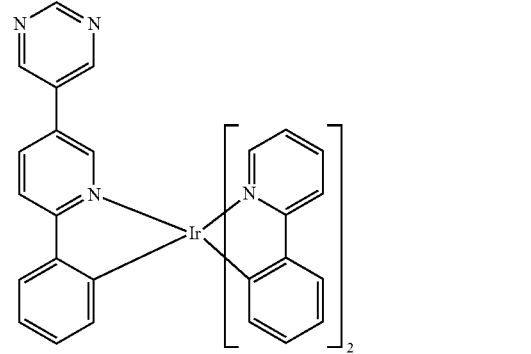
Compound 45
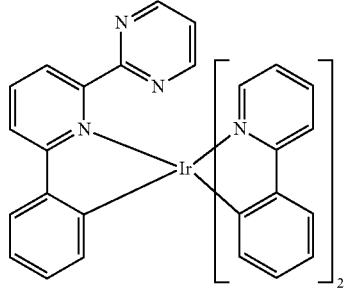
Compound 46
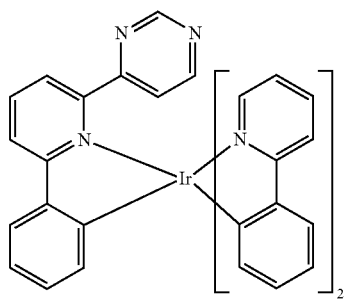
Compound 47
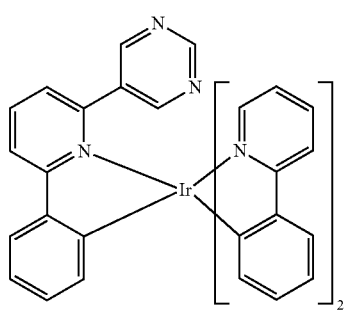
Compound 48
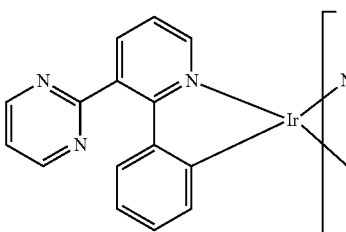
Compound 49
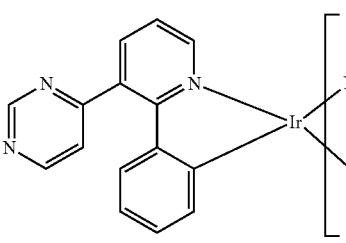

-continued

Compound 50
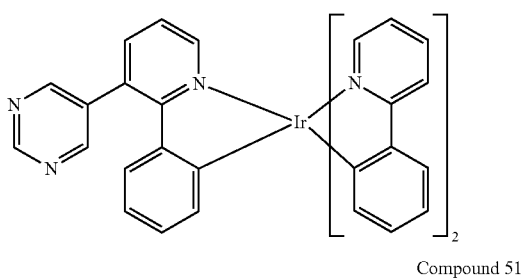

Compound 51
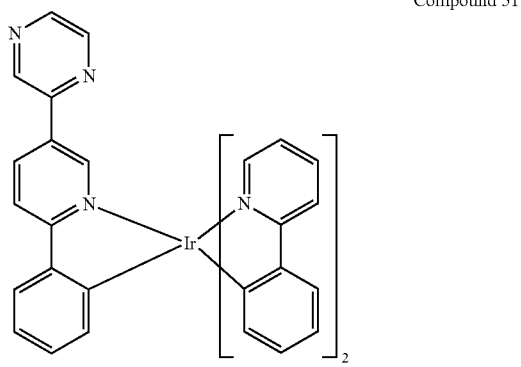

Compound 52
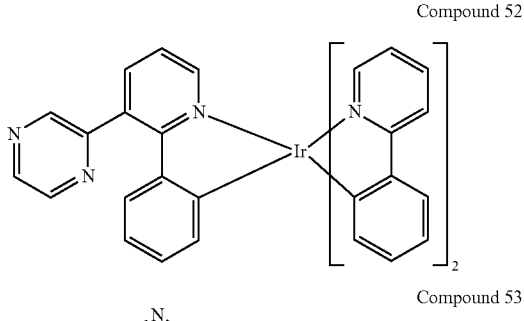

Compound 53
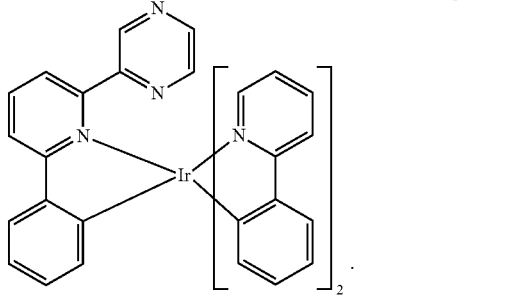

A first device comprising an organic light emitting device is also provided. The device further comprises an anode, a cathode, and an organic layer, disposed between the anode and the cathode. The organic layer comprises a first compound having the formula:

Formula VII
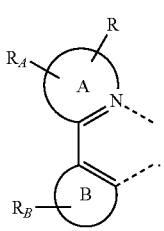

A and B are each independently a 5 or 6-membered carbocyclic or heterocyclic ring. Preferably, B is phenyl. R is a 5 or 6-membered heterocyclic ring. Preferably, R is a 5 or 6 membered heterocyclic ring that contains at least one nitrogen atom. $R_A$ and $R_B$ may represent mono, di, tri, tetra, or penta substitutions. $R_A$ and $R_B$ is independently selected from the group consisting of hydrogen, alkyl, alkoxy, amino, alkenyl, alkynyl, arylkyl, aryl, and heteroaryl. The ligand L is coordinated to a metal M having an atomic number greater than 40. Preferably, the metal M is Ir.

In one aspect, the device comprises a compound having the formula $M(L)_x(L_1)_y(L_2)_z$.

L is

Formula VIII
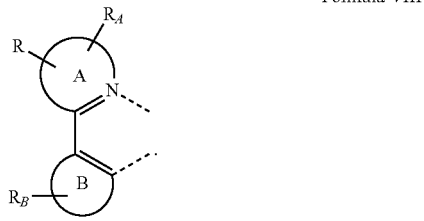

$L_1$ is

Formula IX
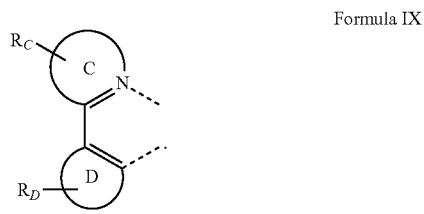

$L_2$ is

Formula X
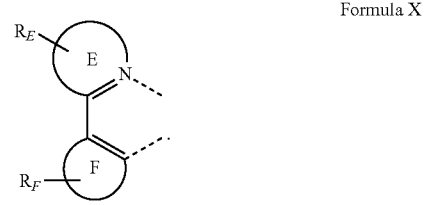

$L_1$ and $L_2$ can be the same or different. x is 1, 2 or 3, y is 0, 1 or 2, z is 0, 1 or 2. x+y+z is the oxidation state of the metal M. A, B, C, D, E and F are each independently a 5 or 6-membered carbocyclic or heterocyclic ring. R is a 5 or 6-membered heterocyclic ring. $R_A$, $R_B$, $R_C$, $R_D$, $R_E$ and $R_F$ may represent mono, di, tri, tetra, or penta substitutions. Each of $R_A$, $R_B$, $R_D$, $R_E$ and $R_F$ is independently selected from the group consisting of hydrogen, alkyl, alkoxy, amino, alkenyl, alkynyl, arylkyl, aryl, and heteroaryl. The ligand L is coordinated bidentately to a metal M having an atomic number greater than 40.

In one aspect, the compound is homoleptic. In a particular aspect, the compound has the formula:

Formula XI

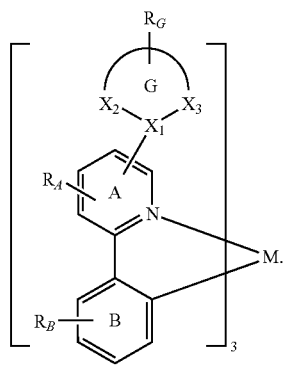

In another aspect, the compound has a formula selected from the group consisting of:

Formula XII

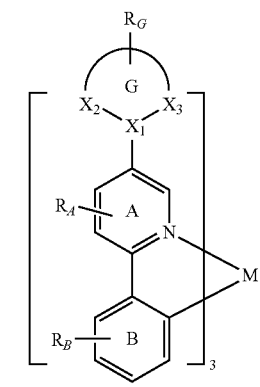

Formula XIII

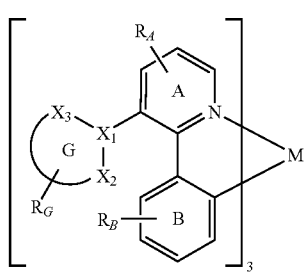

Formula XIV

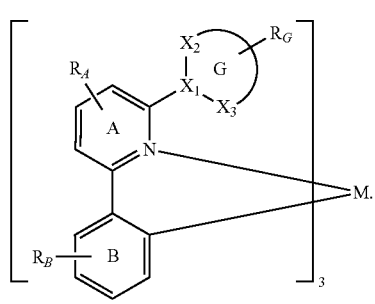

In another aspect, the compound is heteroleptic. In a particular aspect, the compound has the formula:

Formula XV

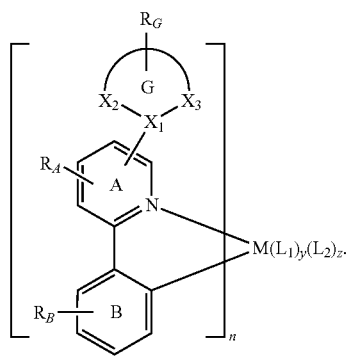

$n+y+z$ is the oxidation state of the metal M. n is at least 1. y is 0, 1 or 2. x is 0, 1, or 2.

In yet another aspect, the compound has a formula selected from the group consisting of:

Formula XVI

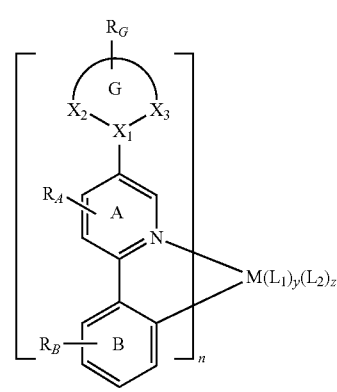

Formula XVII

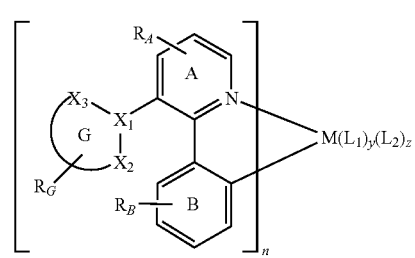

Formula XVIII

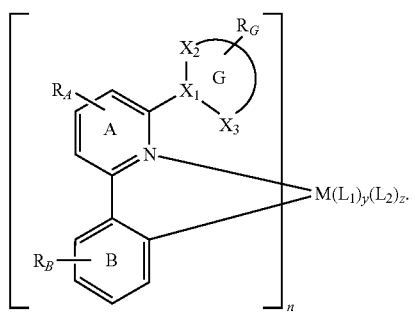

In one aspect, the ligand L is selected from the group consisting of:

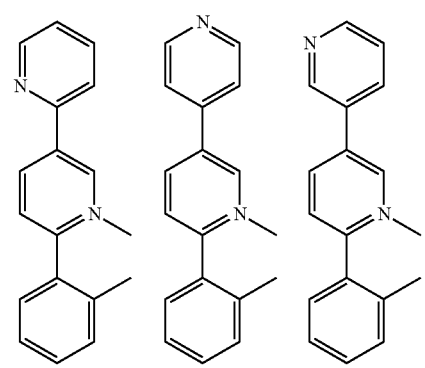
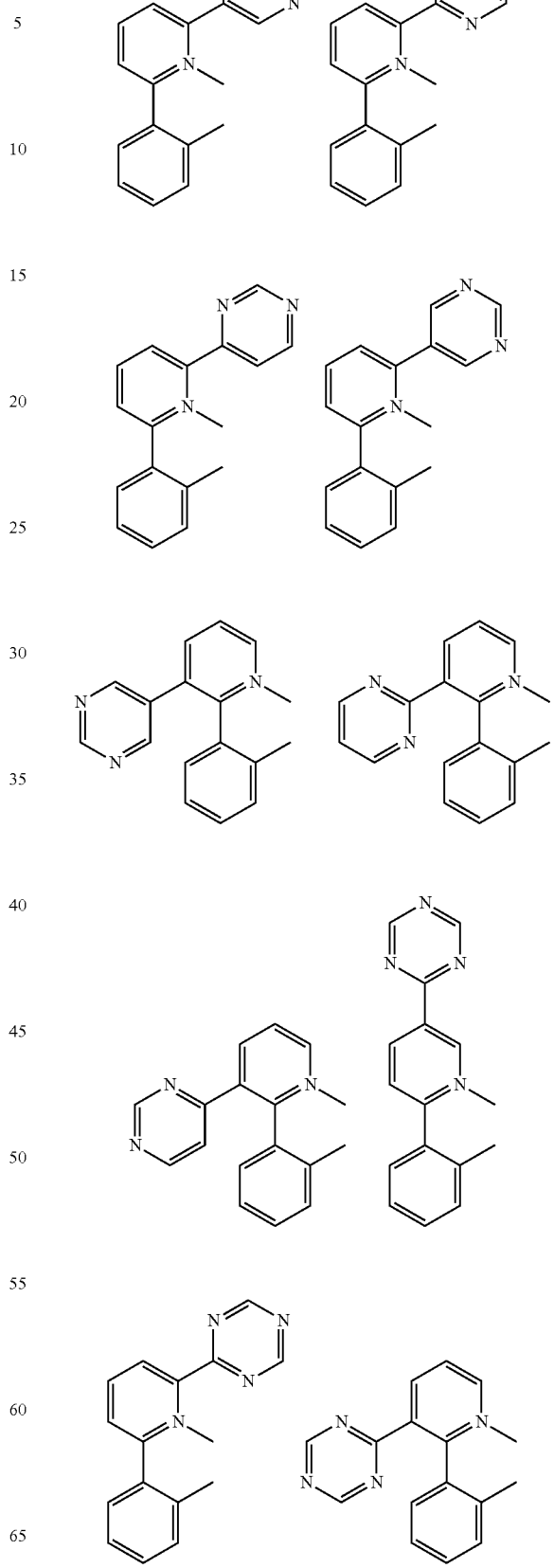

-continued
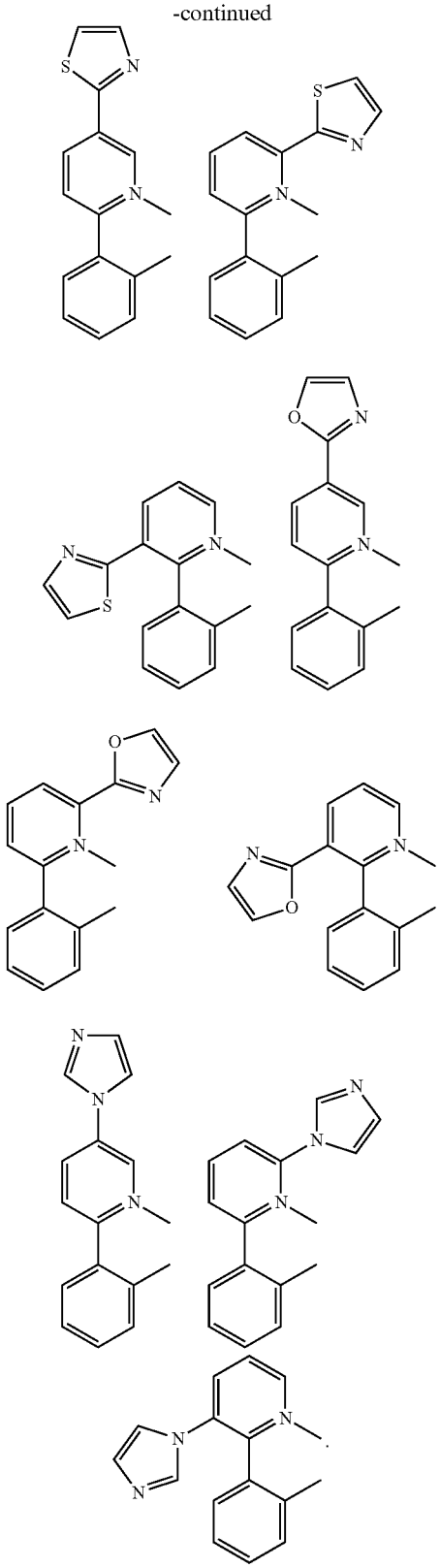
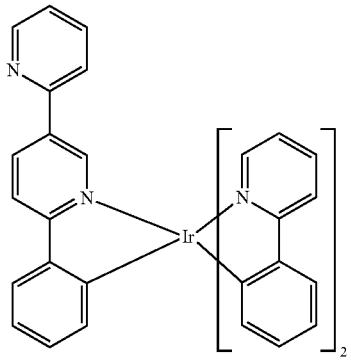
Compound 33
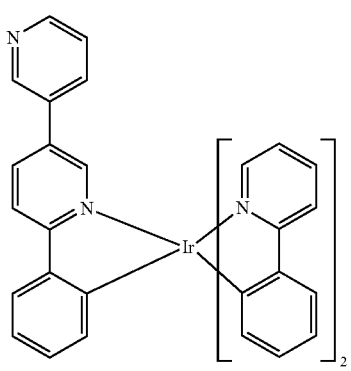
Compound 34
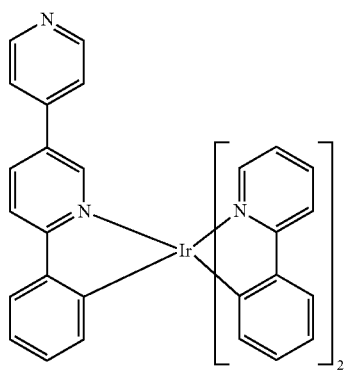
Compound 35
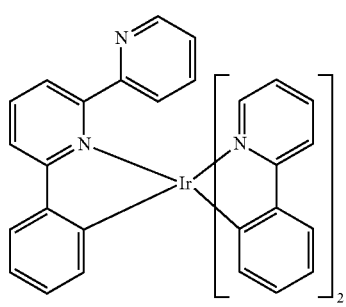
Compound 36
Specific examples of devices containing compounds comprising a phenyl pyridine ligand further substituted with a heterocyclic ring. In particular, the compound is selected from the group consisting of:

Compound 37
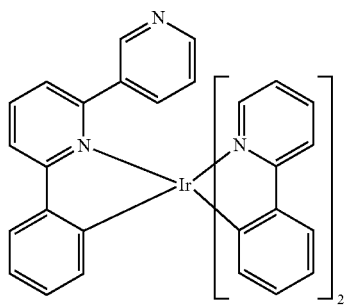
Compound 38
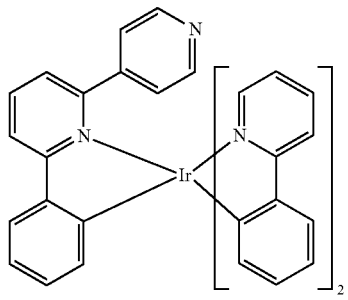
Compound 39
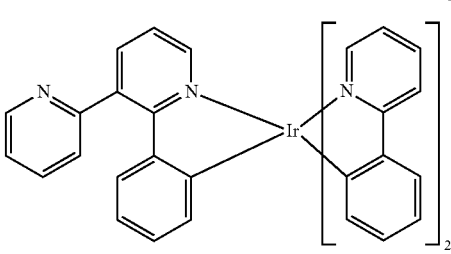
Compound 40
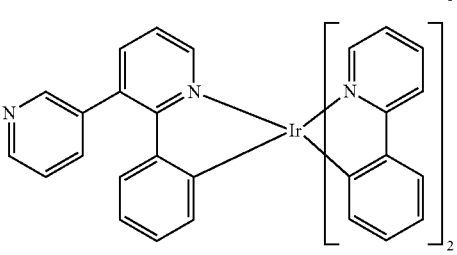
Compound 41
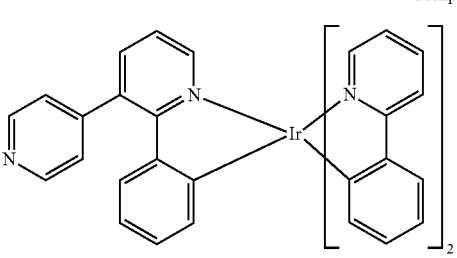
Compound 42
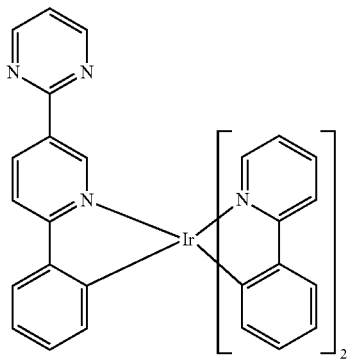
Compound 43
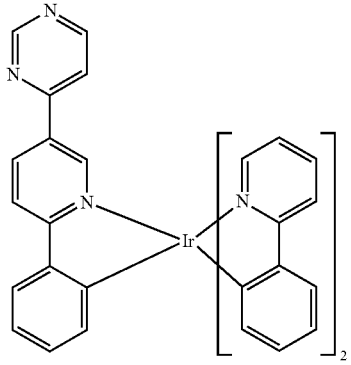
Compound 44
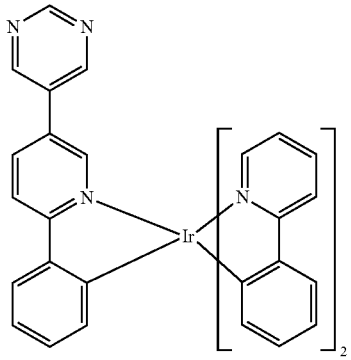
Compound 45
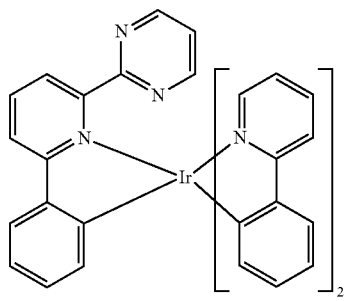

Compound 46

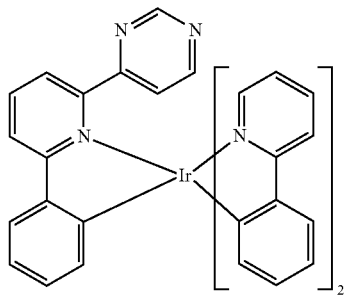

Compound 47

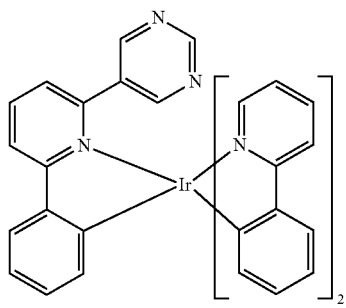

Compound 48

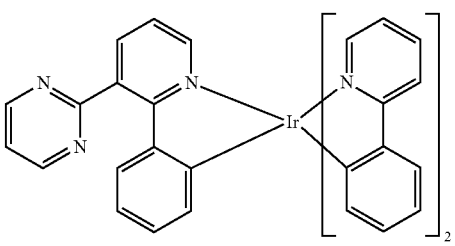

Compound 49

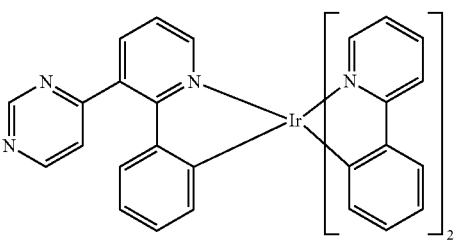

Compound 50

Compound 51

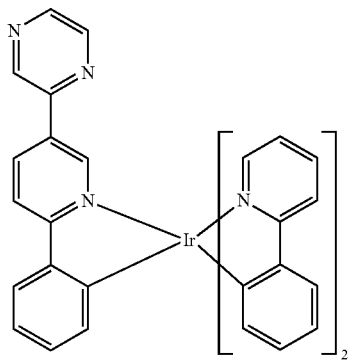

Compound 52

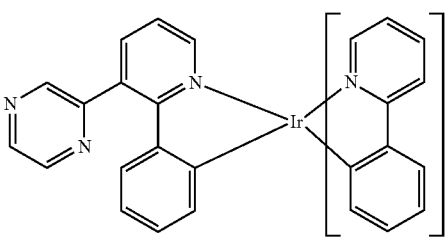

Compound 53

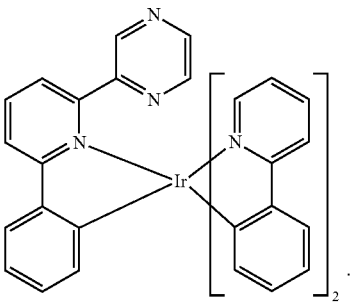

In one aspect, the organic layer is an emissive layer and the first compound having Formula I is an emissive compound.

In another aspect, the organic layer further comprises a second emissive compound. Preferably, the second emissive compound is Compound H

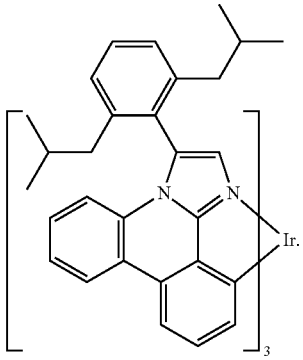

In yet another aspect, the organic layer further comprises a host having the formula:

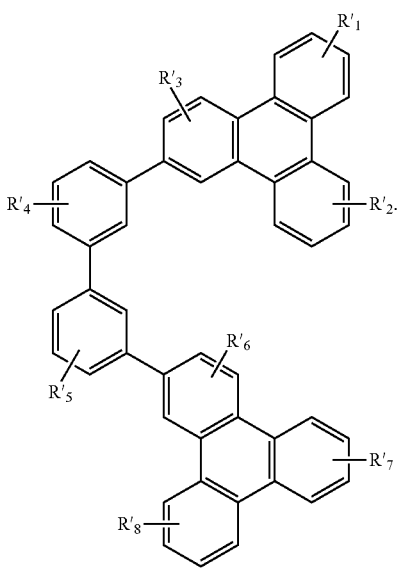

R'$_1$, R'$_2$, R'$_3$, R'$_4$, R'$_5$, R'$_6$, R'$_7$, and R'$_8$ are independently selected from the group consisting of hydrogen, alkyl, alkoxy, amino, alkenyl, alkynyl, arylkyl, aryl, and heteroaryl.

Preferably, the host is:

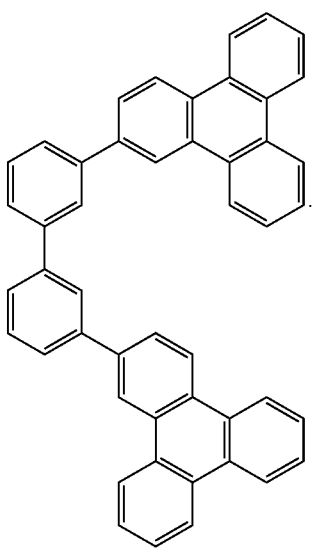

Compound F

In one aspect, the first device is a consumer product. In another aspect, the first device is an organic light emitting device.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed below. The list includes non-limiting classes of materials, non-limiting examples of compounds for each class, and references that disclose the materials.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

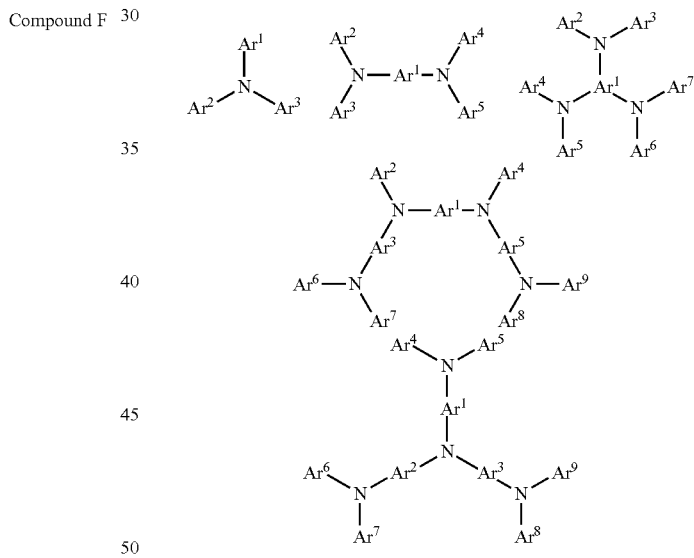

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, alkyl, alkoxy, amino, alkenyl, alkynyl, arylalkyl, heteroalkyl, aryl and heteroaryl.

In one aspect, $Ar^1$ to $Ar^9$ is independently, selected from the group consisting of:

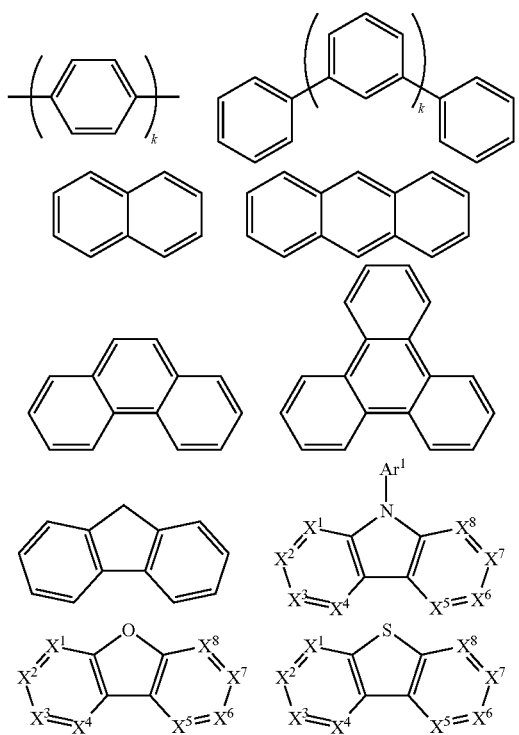

k is an integer from 1 to 20; $X^1$ to $X^8$ is CH or N; $Ar^1$ has the same group defined above.

Examples of metal complexes used in HIL or HTL include, but not limit to the following general formula:

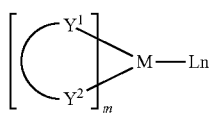

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.
In another aspect, $(Y^1-Y^2)$ is a carbene ligand.
In another aspect, M is selected from Ir, Pt, Os, and Zn.
In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

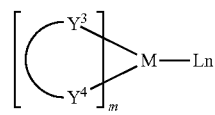

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

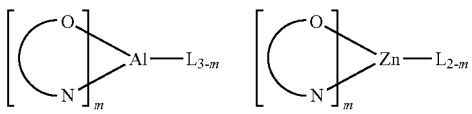

(O—N) is a bidentate ligand, having metal coordinated to atoms O and N.

In another aspect, M is selected from Ir and Pt.
In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, alkyl, alkoxy, amino, alkenyl, alkynyl, arylalkyl, heteroalkyl, aryl and heteroaryl.

In one aspect, host compound contains at least one of the following groups in the molecule:

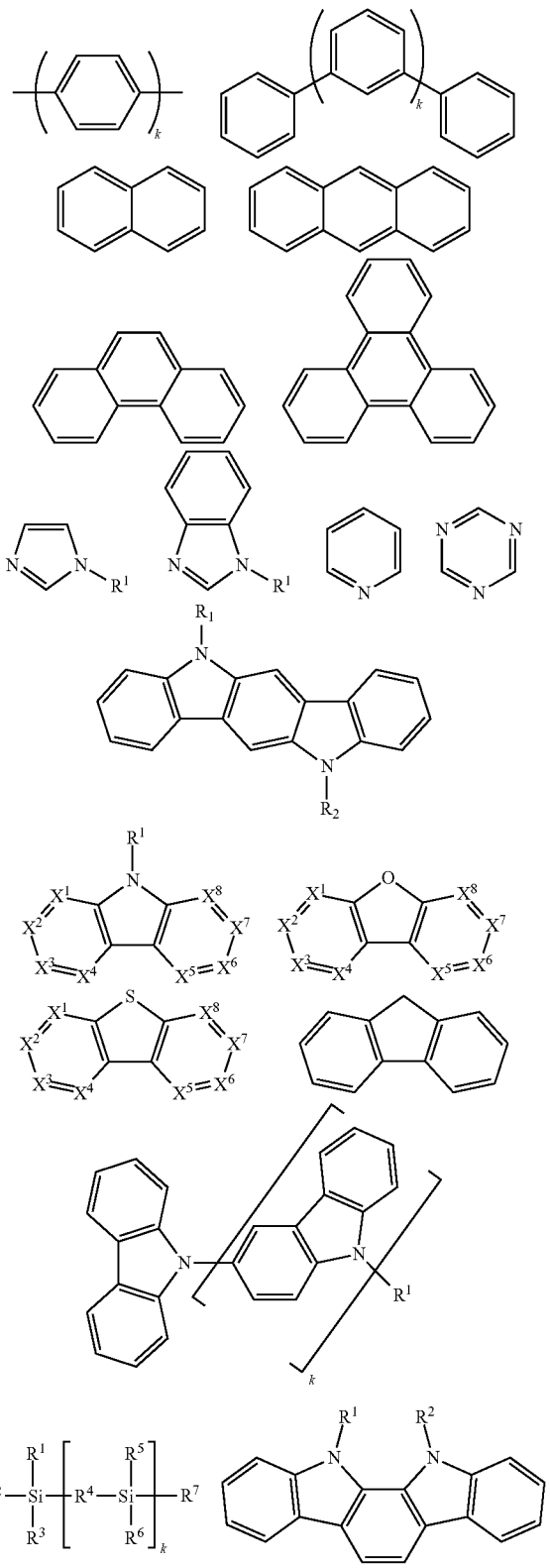

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

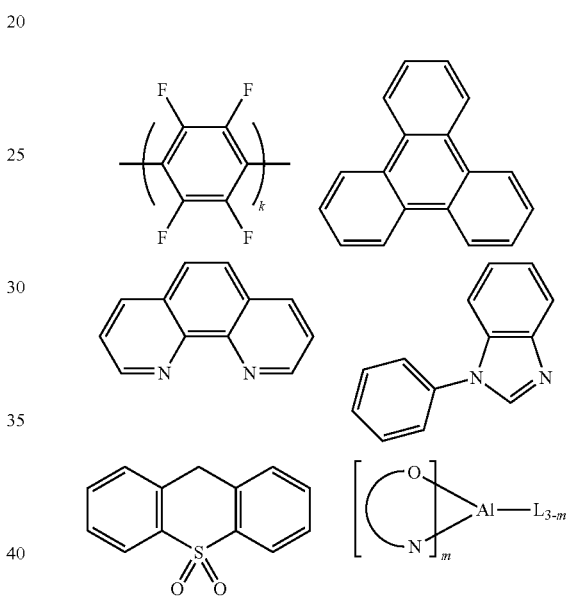

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

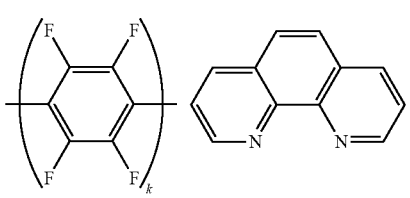

-continued

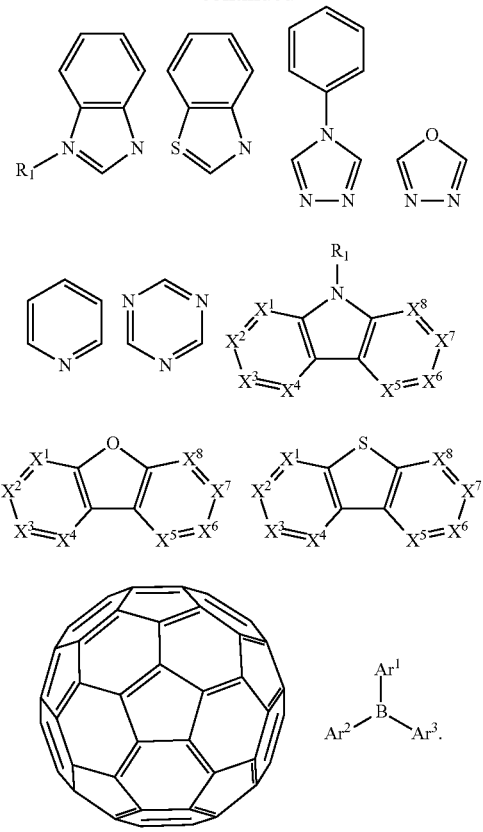

R¹ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

Ar¹ to Ar$^a$ has the similar definition as Ar's mentioned above.

k is an integer from 0 to 20.

X¹ to X⁸ is selected from CH or N.

In another aspect, the metal complexes used in ETL contains, but not limit to the following general formula:

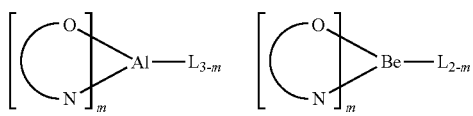

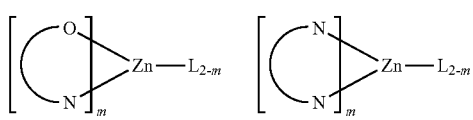

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of OLED device, the hydrogen atoms attached to conjugated rings can be partially or fully deuterated.

The materials described herein as useful for a particular layer in an organic light emitting device may be used in combination with a wide variety of other materials present in the device. For example, emissive dopants disclosed herein may be use din conjunction with a wide variety pf hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| | Hole injection materials | |
| Phthalocyanine and porphryin compounds | | Appl. Phys. Lett. 69, 2160 (1996) |

TABLE 1-continued
| MATERIAL | EXAMPLES OF MATERIAL | PUBLICATIONS |
|---|---|---|
| Starburst triarylamines | 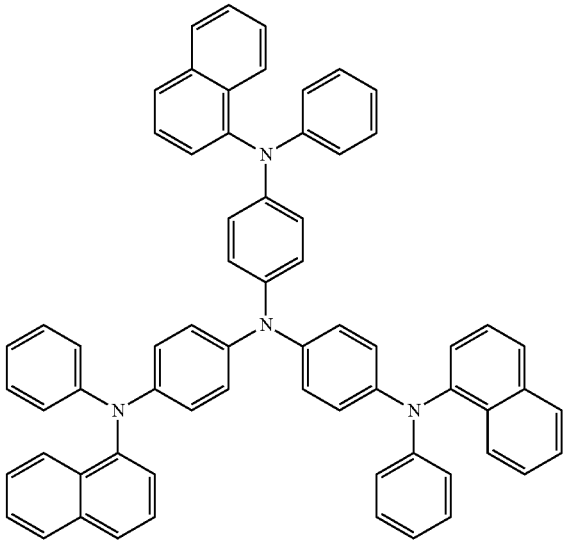 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | 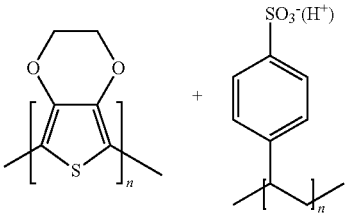 | Synth. Met. 87, 171 (1997) WO2007002683 |
| Phosphonic acid and sliane SAMs | 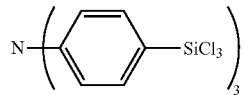 | US20030162053 |
| Triarylamine or polythiophene polymers with conductivity dopants | 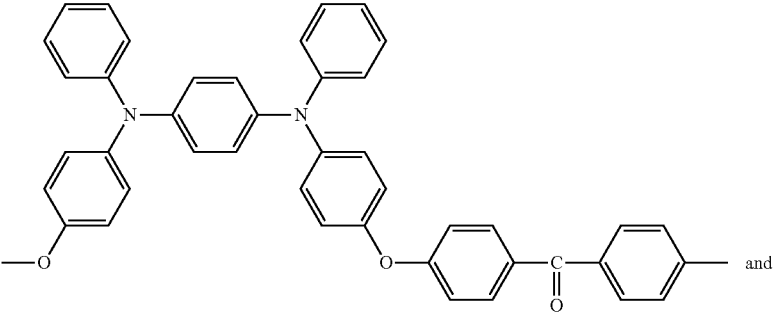 | EA01725079A1 |

TABLE 1-continued
| MATERIAL | EXAMPLES OF MATERIAL | PUBLICATIONS |
|---|---|---|
| | 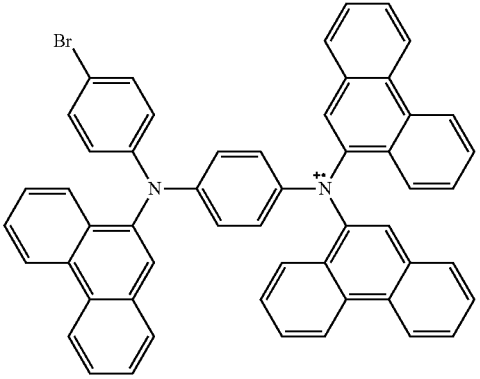 | |
| | 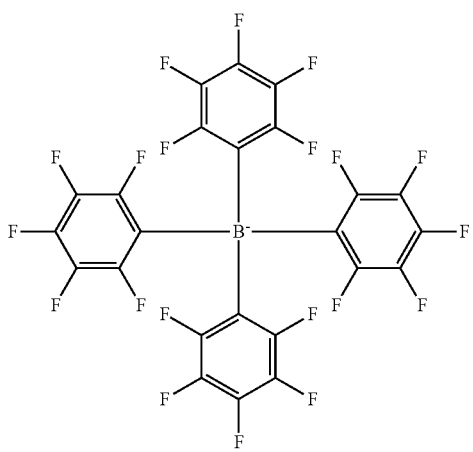 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Arylamines complexed with metal oxides such as molybdenum and tungsten oxides | 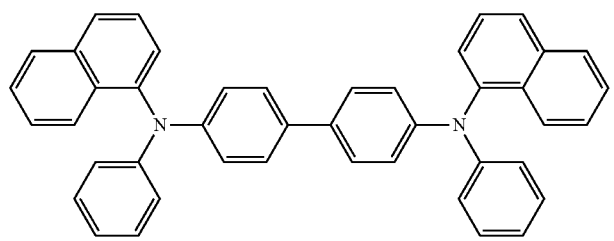 | SID Symposium Digest, 37, 923 (2006) WO2009018009 |
| p-type semi-conducting organic complexes | 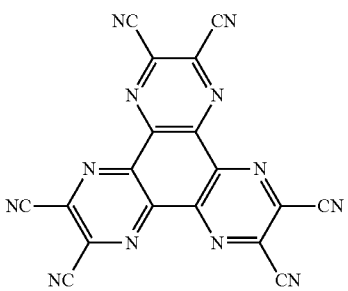 [SMILES: N#Cc1nc2c3nc(C#N)c(C#N)nc3c3nc(C#N)c(C#N)nc3c2nc1C#N] | US20020158242 |
| Metal organometallic complexes | 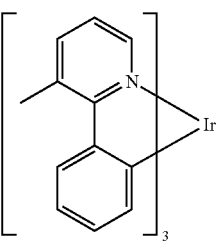 | US20060240279 |

TABLE 1-continued

| MATERIAL | EXAMPLES OF MATERIAL | PUBLICATIONS |
|---|---|---|
| Cross-linkable compounds | | US20080220265 |

Hole transporting materials

| | | |
|---|---|---|
| Triarylamines (e.g., TPD, α-NPD) | | Appl. Phys. Lett. 51, 913 (1987) |
| | | US5061569 |
| | | EP650955 |

TABLE 1-continued

| MATERIAL | EXAMPLES OF MATERIAL | PUBLICATIONS |
|---|---|---|
| | | J. Mater. Chem. 3, 319 (1993) |
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |

TABLE 1-continued
| MATERIAL | EXAMPLES OF MATERIAL | PUBLICATIONS |
|---|---|---|
| Arylamine carbazole compounds | 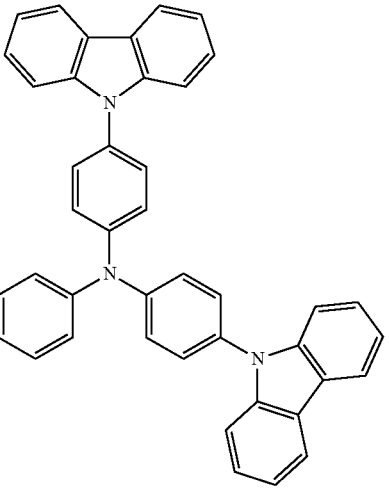 | Adv. Mater. 6, 677 (1994), US20080124572 |
| Triarylamine with (di)benzothiophene/ (di)benzofuran | 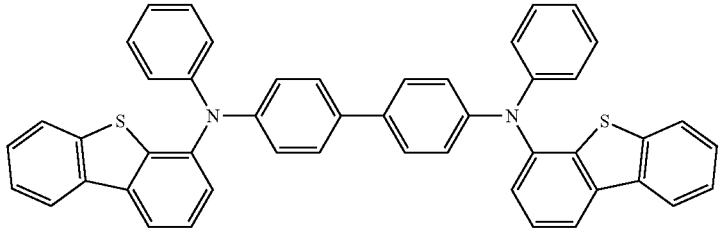 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |
| Indolocarbazoles | 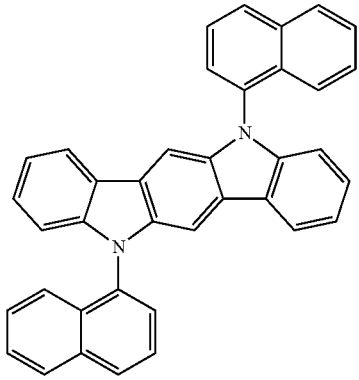 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 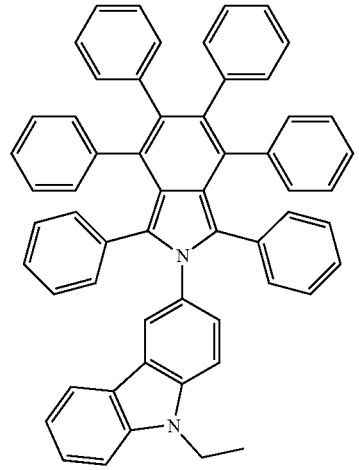 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |

TABLE 1-continued

| MATERIAL | EXAMPLES OF MATERIAL | PUBLICATIONS |
|---|---|---|
| Metal carbene complexes | | US20080018221 |

Phosphorescent OLED host materials

Red hosts

| | | |
|---|---|---|
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |

TABLE 1-continued

| MATERIAL | EXAMPLES OF MATERIAL | PUBLICATIONS |
|---|---|---|
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2009062578 |

Green hosts

| | | |
|---|---|---|
| Arylcarbazoles | | Appl. Phys. Lett. 78, 1622 (2001) |
| | | US20030175553 |

TABLE 1-continued

| MATERIAL | EXAMPLES OF MATERIAL | PUBLICATIONS |
|---|---|---|
| | | WO2001039234 |
| Aryltriphenylene compounds | | US20060280965 |
| | | US20060280965 |
| | | WO2009021126 |
| Donor acceptor type molecules | | WO2008056746 |

TABLE 1-continued

| MATERIAL | EXAMPLES OF MATERIAL | PUBLICATIONS |
|---|---|---|
| Aza-carbazole/ DBT/DBF | | JP2008074939 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |
| | | WO2006132173 |

TABLE 1-continued

| MATERIAL | EXAMPLES OF MATERIAL | PUBLICATIONS |
|---|---|---|
| | | JP200511610 |
| Spirofluorene-carbazole compounds | | JP2007254297 |
| | | JP2007254297 |
| Indolocabazoles | | WO2007063796 |

| MATERIAL | EXAMPLES OF MATERIAL | PUBLICATIONS |
|---|---|---|
| | 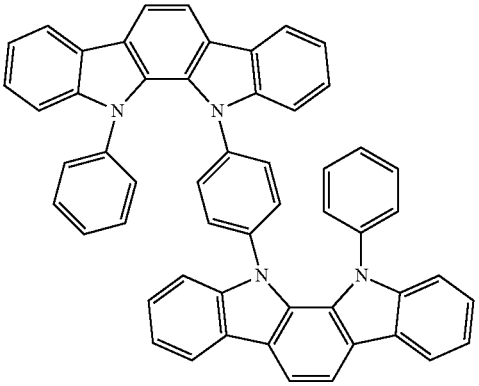 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 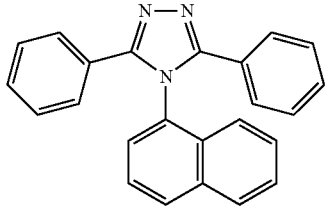 [SMILES: c1ccc(-c2nnc(-c3ccccc3)n2-c2cccc3ccccc23)cc1] | J. Appl. Phys. 90, 5048 (2001) |
| | 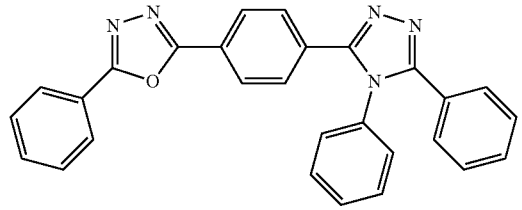 [SMILES: c1ccc(-c2nnc(-c3ccc(-c4nnc(-c5ccccc5)n4-c4ccccc4)cc3)o2)cc1] | WO2004107822 |
| Tetraphenylene complexes | 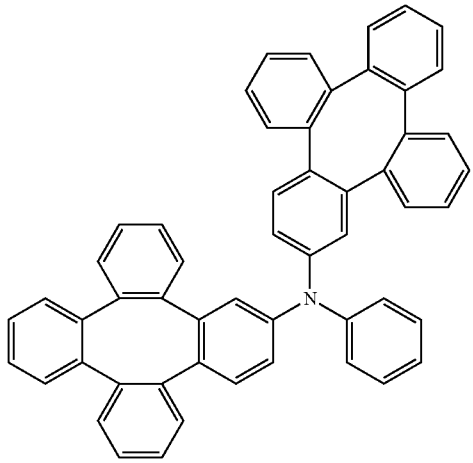 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 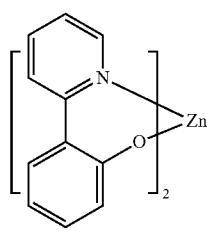 | WO2005030900 |

TABLE 1-continued

| MATERIAL | EXAMPLES OF MATERIAL | PUBLICATIONS |
| --- | --- | --- |
| Metal coordination complexes (e.g., Zn, Al with N^N ligands) | | US20040137268, US20040137267 |

Blue hosts

| MATERIAL | EXAMPLES OF MATERIAL | PUBLICATIONS |
| --- | --- | --- |
| Arylcarbazoles | | Appl. Phys. Lett. 82, 2422 (2003) |
| | | US20070190359 |
| Dibenzothiophene/ Dibenzofuran- carbazole compounds | | WO2006114966, US20090167162 |
| | | US20090167162 |
| | | WO2009086028 |

TABLE 1-continued
| MATERIAL | EXAMPLES OF MATERIAL | PUBLICATIONS |
|---|---|---|
| | 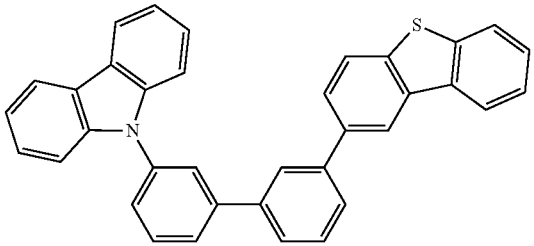 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 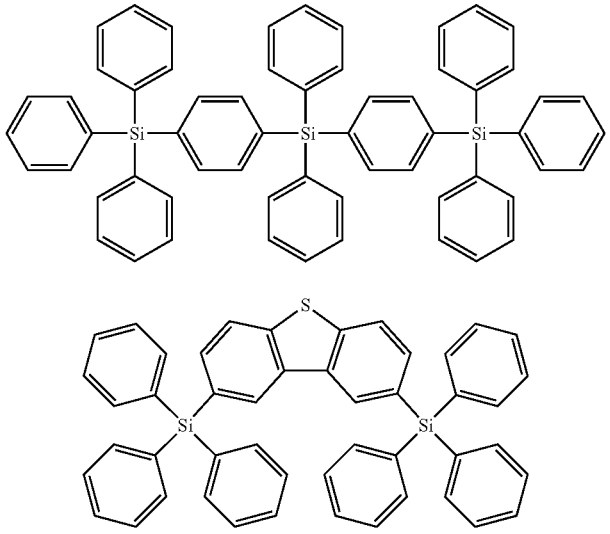 | US20050238919 |
| | | WO2009003898 |
| Silicon/Germanium aryl compounds | 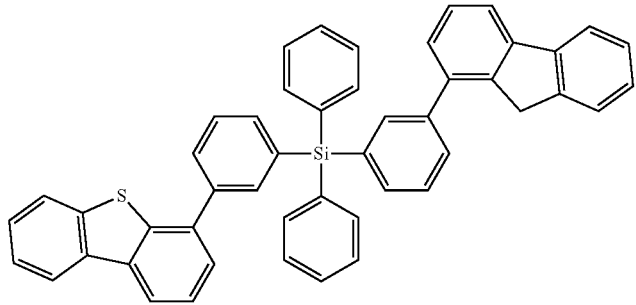 [SMILES: c1ccc([Si](c2ccccc2)(c2cccc(-c3cccc4c3Cc3ccccc3-4)c2)c2cccc(-c3cccc4c3sc3ccccc34)c2)cc1] | EP2034538A |
| Aryl benzoyl ester | 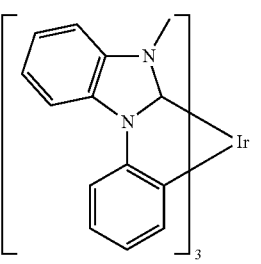 | WO2006100298 |
| High triplet metal organometallic complex | | US7154114 |

TABLE 1-continued

| MATERIAL | EXAMPLES OF MATERIAL | PUBLICATIONS |
|---|---|---|
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 1-continued

| MATERIAL | EXAMPLES OF MATERIAL | PUBLICATIONS |
|---|---|---|
| | | US20060202194 |
| | | US20070087321 |
| | | US20070087321 |
| | | Adv. Mater. 19, 739 (2007) |
| | | WO2009100991 |

TABLE 1-continued
| MATERIAL | EXAMPLES OF MATERIAL | PUBLICATIONS |
|---|---|---|
| | 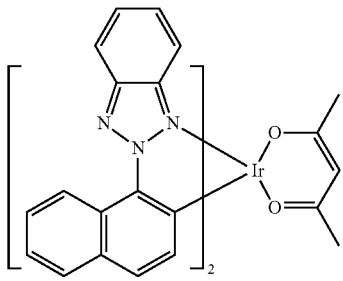 | WO2008101842 |
| Platinum(II) organometallic complexes | 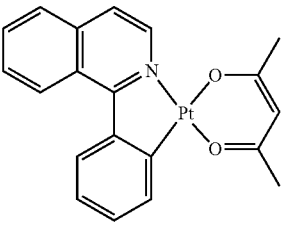 | WO2003040257 |
| Osminum(III) complexes | 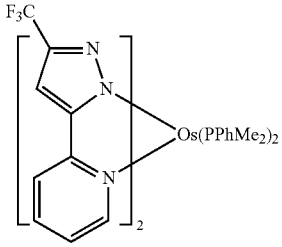 | Chem. Mater. 17, 3532 (2005) |
| Ruthenium(II) complexes | 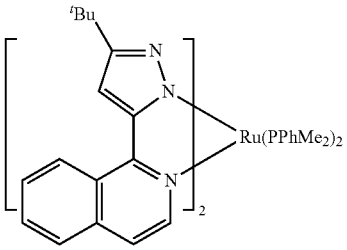 | Adv. Mater. 17, 1059 (2005) |
| Rhenium (I), (II), and (III) complexes | 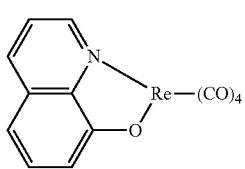 | US20050244673 |

TABLE 1-continued
| MATERIAL | EXAMPLES OF MATERIAL | PUBLICATIONS |
|---|---|---|
| Green dopants | | |
| Iridium(III) organometallic complexes | 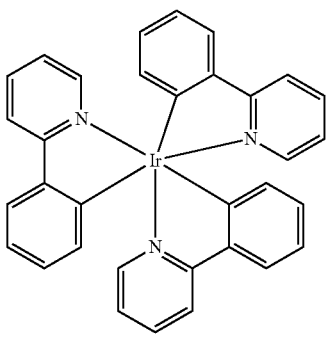<br>and its derivatives | Inorg. Chem. 40, 1704 (2001) |
| | 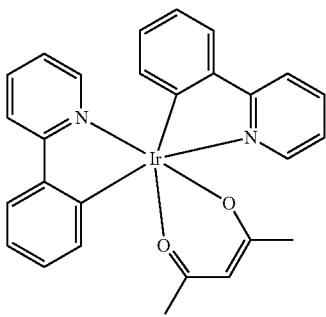 | US20020034656 |
| | 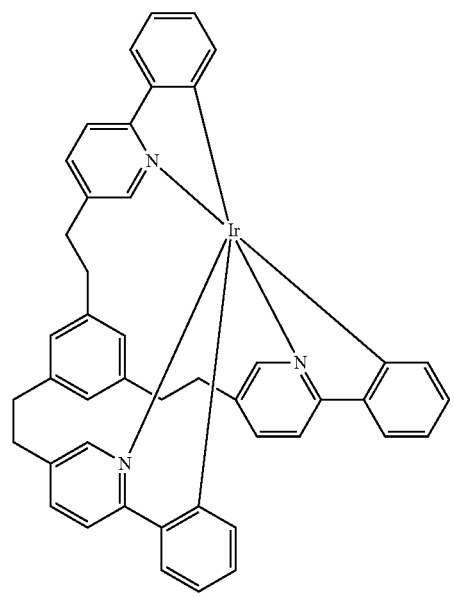 | US7332232 |

TABLE 1-continued

| MATERIAL | EXAMPLES OF MATERIAL | PUBLICATIONS |
|---|---|---|
| | | US20090108737 |
| | | US20090039776 |
| | | US6921915 |
| | | US6687266 |
| | | Chem. Mater. 16, 2480 (2004) |

TABLE 1-continued

| MATERIAL | EXAMPLES OF MATERIAL | PUBLICATIONS |
|---|---|---|
| | | US20070190359 |
| | | US 20060008670<br>JP2007123392 |
| | | Adv. Mater. 16, 2003 (2004) |
| | | Angew. Chem. Int. Ed. 2006, 45, 7800 |
| | | WO2009050290 |
| | | US20090165846 |

TABLE 1-continued

| MATERIAL | EXAMPLES OF MATERIAL | PUBLICATIONS |
|---|---|---|
| | | US20080015355 |
| Monomer for polymeric metal organometallic compounds | | US7250226, US7396598 |
| Pt(II) organometallic complexes, including polydentated ligands | | Appl. Phys. Lett. 86, 153505 (2005) |
| | | Appl. Phys. Lett. 86, 153505 (2005) |

TABLE 1-continued
| MATERIAL | EXAMPLES OF MATERIAL | PUBLICATIONS |
|---|---|---|
| | 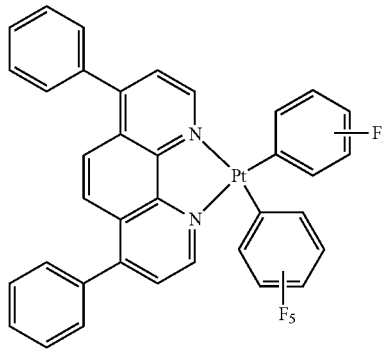 | Chem. Lett. 34, 592 (2005) |
| | 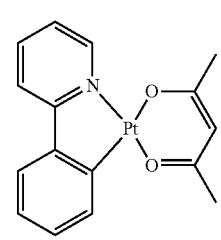 | WO2002015645 |
| | 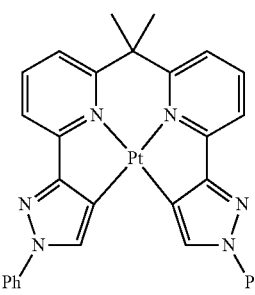 | US20060263635 |
| Cu complexes | 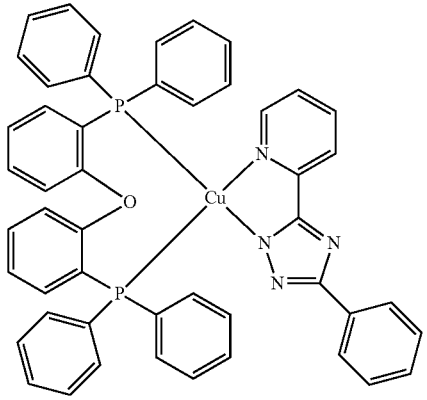 | WO2009000673 |
| Gold complexes | 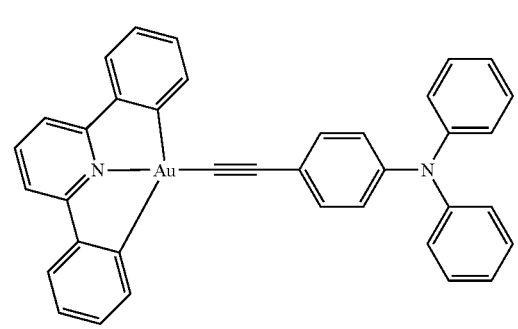 | Chem. Commun. 2906 (2005) |

TABLE 1-continued

| MATERIAL | EXAMPLES OF MATERIAL | PUBLICATIONS |
|---|---|---|
| Rhenium(III) complexes | | Inorg. Chem. 42, 1248 (2003) |
| Deuterated organometallic complexes | | US20030138657 |
| Organometallic complexes with two or more metal centers | | US20030152802 |
| | | US7090928 |

TABLE 1-continued
| MATERIAL | EXAMPLES OF MATERIAL | PUBLICATIONS |
|---|---|---|
| Blue dopants | | |
| Iridium(III) organometallic complexes | 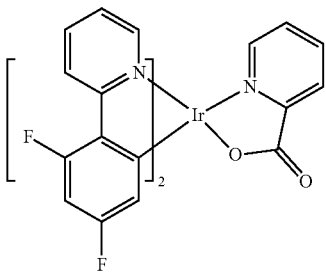 | WO2002002714 |
| | 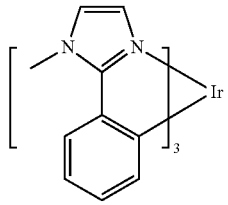 | WO2006009024 |
| | 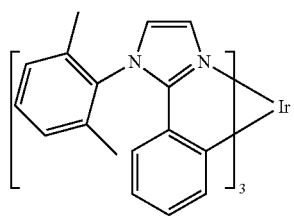 | US20060251923 |
| | 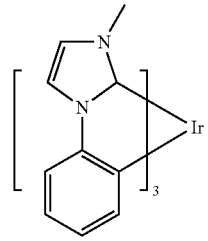 | US7393599, WO2006056418, US20050260441, WO2005019373 |
| | 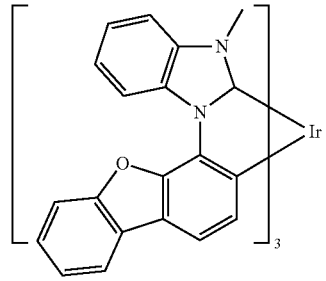 | US7534505 |
| | 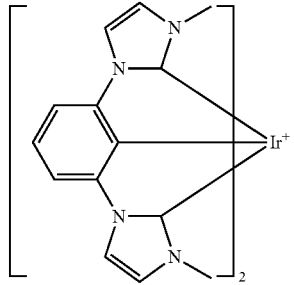 | US7445855 |

TABLE 1-continued

| MATERIAL | EXAMPLES OF MATERIAL | PUBLICATIONS |
|---|---|---|
| | | US20070190359, US20080297033 |
| | | US7338722 |
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |

TABLE 1-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | US7279704 |

TABLE 1-continued

| MATERIAL | EXAMPLES OF MATERIAL | PUBLICATIONS |
|---|---|---|
|  |  | Organometallics 23, 3745 (2004) |
| Gold complexes |  | Appl. Phys. Lett. 74, 1361 (1999) |
| Platinum(II) complexes |  | WO2006098120, WO2006103874 |
| Exciton/hole blocking layer materials | | |
| Bathocuprine compounds (e.g., BCP, BPhen) |  | Appl. Phys. Lett. 75, 4 (1999) |
|  |  | Appl. Phys. Lett. 79, 449 (2001) |
| Metal 8-hydroxyquinolates (e.g., BAlq) |  | Appl. Phys. Lett. 81, 162 (2002) |

TABLE 1-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 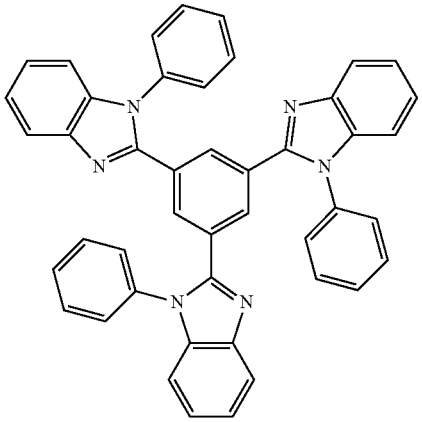 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 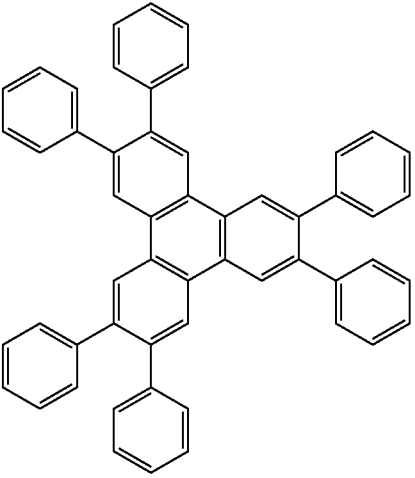 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 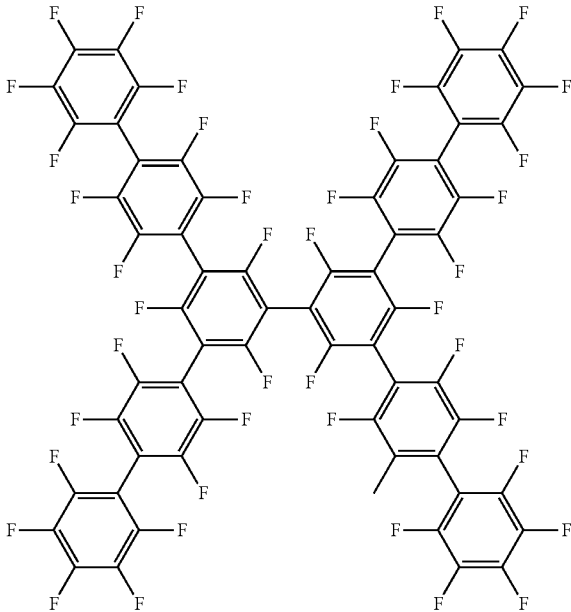 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 1-continued

| MATERIAL | EXAMPLES OF MATERIAL | PUBLICATIONS |
|---|---|---|
| Phenothiazine-S-oxide | | WO2008132085 |
| Electron transporting materials | | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |

TABLE 1-continued

| MATERIAL | EXAMPLES OF MATERIAL | PUBLICATIONS |
|---|---|---|
| Metal 8-hydroxyquinolates (e.g., $Alq_3$, $Zrq_4$) | | Chem. Lett. 5, 905 (1993) |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE 1-continued
| MATERIAL | EXAMPLES OF MATERIAL | PUBLICATIONS |
|---|---|---|
|  | 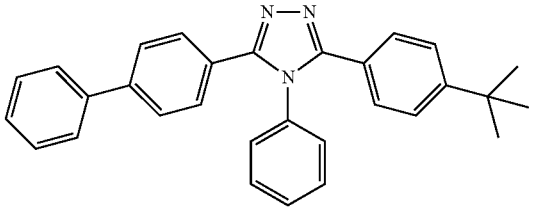 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 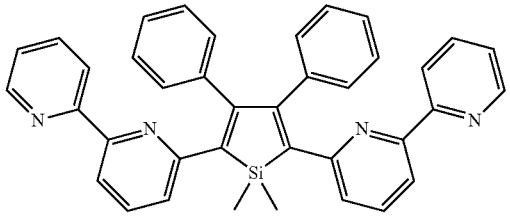 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 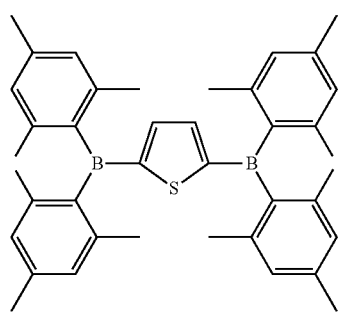 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 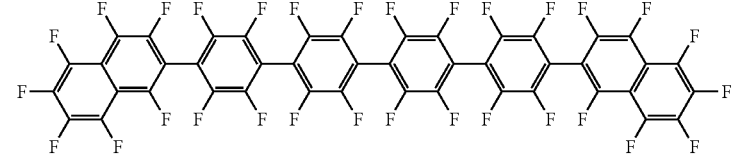 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 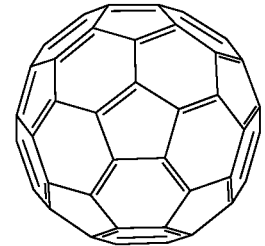 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 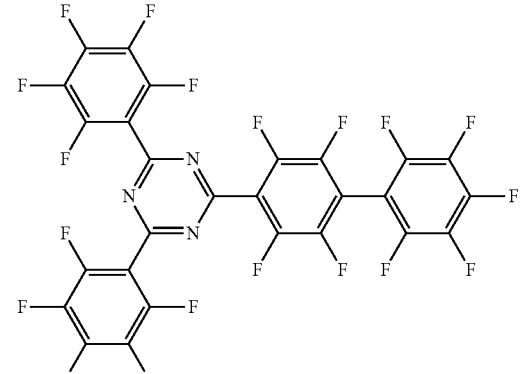 | US20040036077 |

TABLE 1-continued
| MATERIAL | EXAMPLES OF MATERIAL | PUBLICATIONS |
|---|---|---|
| Zn (N^N) complexes | | US6528187 |
EXPERIMENTAL
Compound Examples
Several of the compounds were synthesized as follows:
Example 1
Synthesis of Compound 1
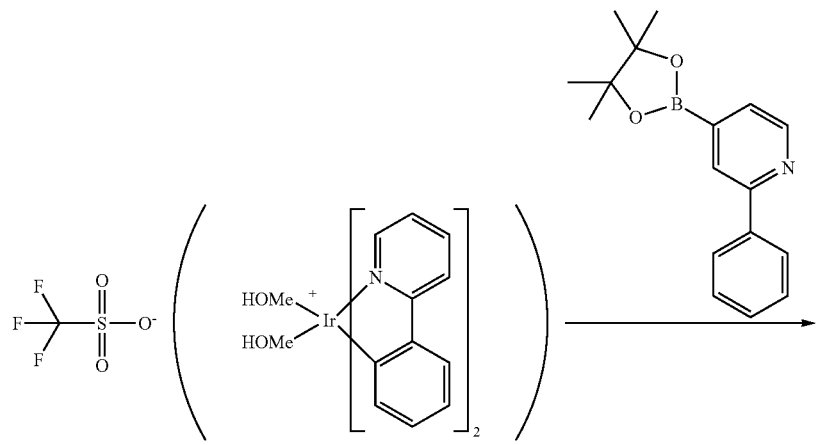
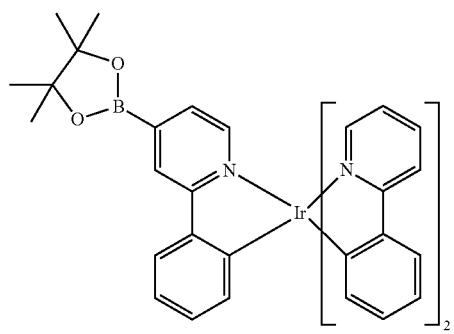

The iridium phenylpyridine triflate salt was refluxed in ethanol with 2-phenyl-4-(4,4,5,5-tetramethyl-1,3,2-dioxaborolan-2-yl)pyridine (4 g, 14.23 mmol) under nitrogen for 24 h. After cooling to room temperature, the mixture was filtered through a Celite pad and washed with ethanol and hexanes to give 60% yield of the desired product. The product was used for the next step without further purification.

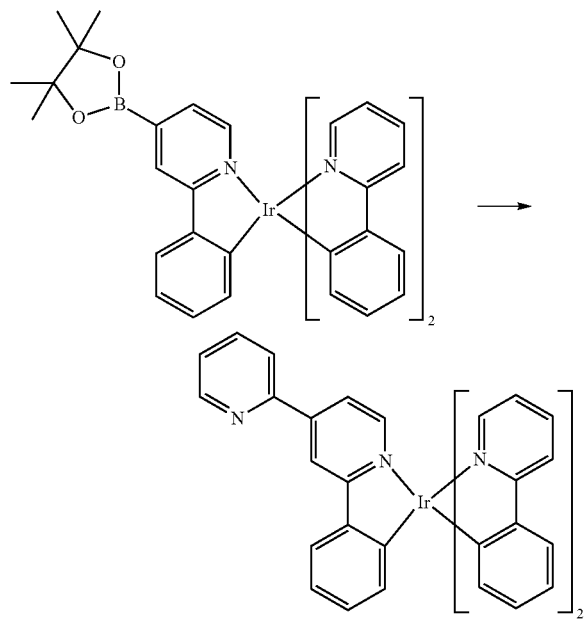

A mixture of Iridium phenylpyridine boronic ester complex (2.5 g, 3.20 mmol), 2-chloropyridine (0.545 g, 4.80 mmol), and Potassium phosphate (1.699 g, 8.01 mmol) in 100 mL of toluene and 10 mL of H$_2$O was bubbled with N$_2$ for 20 minutes. Pd$_2$(dba)$_3$ (0.029 g, 0.032 mmol) and dicyclohexyl (2',6'-dimethoxy-[1,1'-biphenyl]-2-yl)phosphine (0.053 g, 0.128 mmol) were then added, and the mixture was heated to reflux under N$_2$ for 14 h. The mixture was cooled and extracted with dichloromethane. The organic extracts were dried over MgSO$_4$, filtered and evaporated to a residue. The residue was coated on Celite and purified by column using dichloromethane as solvent. 0.8 g product was obtained.

Example 2

Synthesis of Compound 2

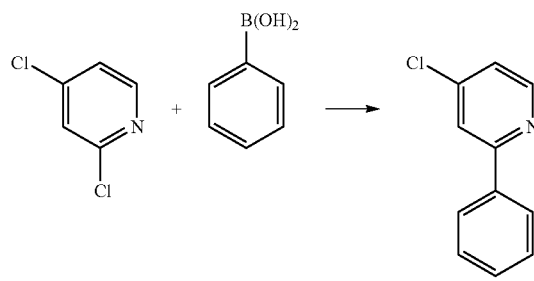

2,4-dichloropyridine (21.90 mL, 203 mmol), phenylboronic acid (24.72 g, 203 mmol) and Potassium carbonate (84.0 g, 608 mmol), dimethoxy ethane (500 mL) and water (150 mL) were placed in a 3-neck round bottom flask. Nitrogen gas was bubbled through the reaction mixture for 30 minutes. Tetrakis triphenylphosphine Pd(0) (2.343 g, 2.027 mmol)) was then added and the reaction mixture was refluxed for 18 h. The aqueous layer was removed and organic layer was concentrated to dryness. The crude product was purified using silica gel chromatography.

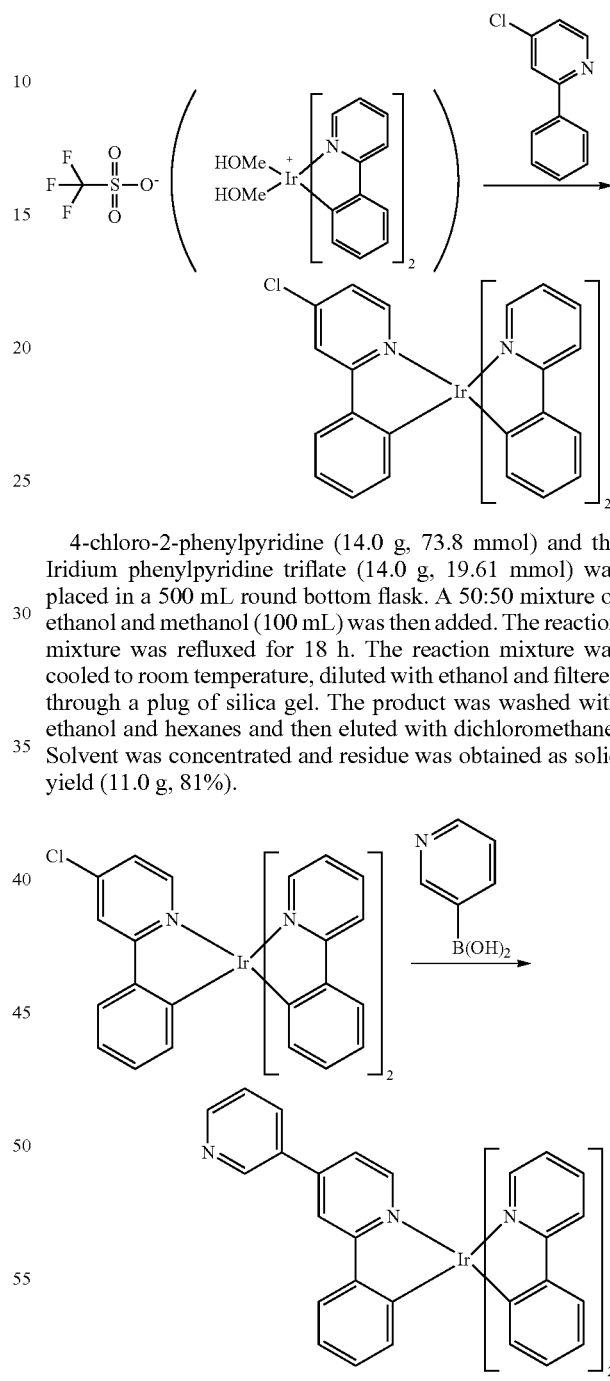

4-chloro-2-phenylpyridine (14.0 g, 73.8 mmol) and the Iridium phenylpyridine triflate (14.0 g, 19.61 mmol) was placed in a 500 mL round bottom flask. A 50:50 mixture of ethanol and methanol (100 mL) was then added. The reaction mixture was refluxed for 18 h. The reaction mixture was cooled to room temperature, diluted with ethanol and filtered through a plug of silica gel. The product was washed with ethanol and hexanes and then eluted with dichloromethane. Solvent was concentrated and residue was obtained as solid yield (11.0 g, 81%).

The heteroleptic Iridium pre cursor (4.0 g, 5.80 mmol), pyridin-3-ylboronic acid (3.57 g, 29.0 mmol), Potassium phosphate tribasic monohydrate (4.01 g, 17.41 mmol) and dicyclohexyl(2',6'-dimethoxy-[1,1'-biphenyl]-2-yl)phosphine (0.095 g, 0.232 mmol), toluene (250 mL) and Water (25 mL) were all placed in a 500 mL 3-neck round bottom flask. Nitrogen gas was bubbled through the reaction mixture 30 minutes. Pd$_2$(dba)$_3$ (0.053 g, 0.058 mmol) was then added and the reaction mixture was refluxed for 18 h. They reaction was cooled to room temperature and the aqueous layer was removed. The organic fraction was concentrated and the crude product was obtained. The crude was further purified using deactivated neutral alumina to give 1.2 g of product (Yield=28.2%).

Example 3

Synthesis of Compound 3

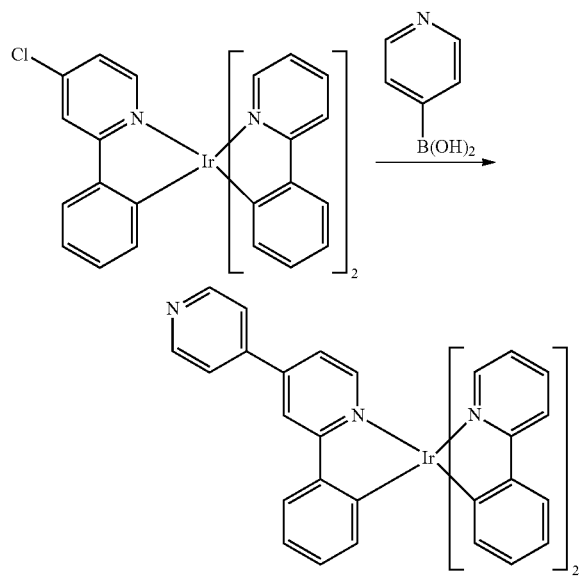

The heteroleptic Iridium pre cursor (4.0 g, 5.80 mmol), pyridin-4-ylboronic acid (1.0 g, 9 mmol), Potassium phosphate tribasic monohydrate (4.01 g, 17.41 mmol) and dicyclohexyl(2',6'-dimethoxy-[1,1'-biphenyl]-2-yl)phosphine (0.095 g, 0.232 mmol), toluene (250 mL) and Water (25 mL) were all placed in a 500 mL 3-neck round bottom flask. Nitrogen gas was bubbled through the reaction mixture 30 minutes. $Pd_2(dba)_3$ (0.106 g, 0.116 mmol) was then added and the reaction mixture was refluxed for 18 h. The reaction was cooled to room temperature and the aqueous layer was removed. The organic fraction was concentrated and the crude product was obtained. The crude was further purified using deactivated neutral alumina to give 2.9 g of product (68.2% yield).

Example 4

Synthesis of Compound 4

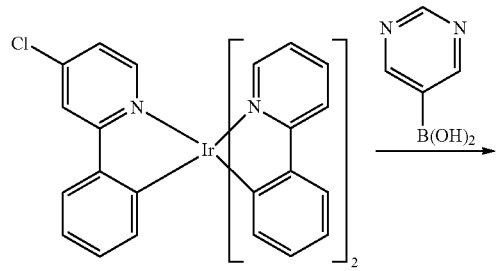

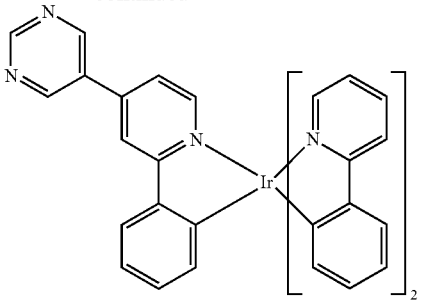

The heteroleptic Iridium pre cursor (5.56 g, 8.09 mmol), pyrimidin-5-ylboronic acid (5.01 g, 40.5 mmol), Potassium phosphate tribasic monohydrate (5.59 g, 24.27 mmol) and dicyclohexyl(2',6'-dimethoxy-[1,1'-biphenyl]-2-yl)phosphine (0.133 g, 0.324 mmol), toluene (250 mL) and water (25 mL) were all placed in a 500 mL 3-neck round bottom flask. Nitrogen gas was bubbled through the reaction mixture 30 minutes. $Pd_2(dba)_3$ (0.222 g, 0.243 mmol) was then added and the reaction mixture was refluxed for 18 h. The reaction was cooled to room temperature and the aqueous layer was removed. The organic fraction was concentrated and the crude product was obtained. The crude was further purified using deactivated neutral alumina to give 3.9 g of product (66.4% yield).

DEVICE EXAMPLES

All device examples were fabricated by high vacuum ($<10^{-7}$ Ton) thermal evaporation. The anode electrode is 1200 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

The organic stack of the Device Example consisted of sequentially, from the ITO surface, 100 Å of hole injection layer (HIL), 300 Å of 4,4'-bis[N-(1-naphthyl)-N-phenylamino]biphenyl (α-NPD) as the hole transporting later (HTL), 300 Å of host doped with 7-10% of Compound 1-4 as the emissive layer (EML), 100 Å of blocking layer (BL) and 400 Å of $Alq_3$ (tris-8-hydroxyquinoline aluminum) as the ETL1. For devices in which LG101 was used as the HIL, LG101 was purchased from LG Chem and used as received.

Examples 6 and 7 were fabricated similarly to other device examples except there were two emissive compounds in the EML.

As used herein, the following compounds have the following structures:

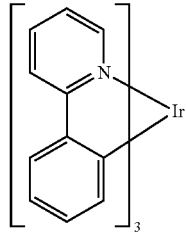

Compound A

Compound B
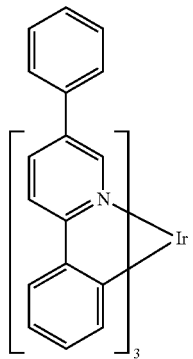
Compound C
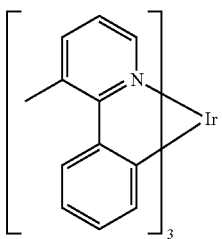
Compound D
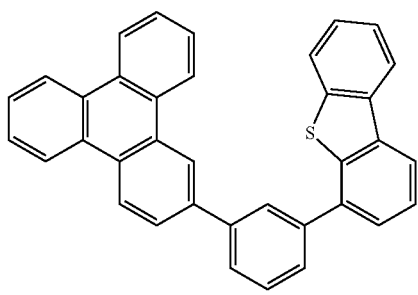
Compound E
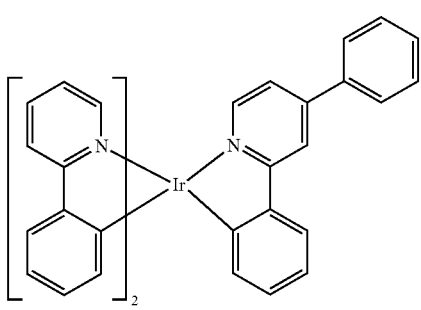
Compound F
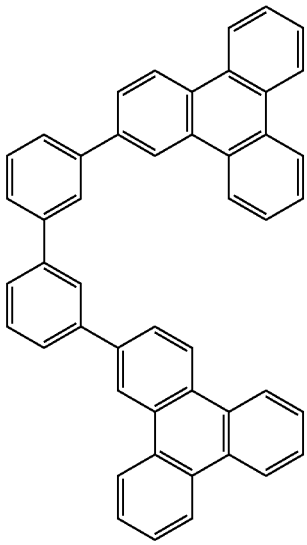
Compound G
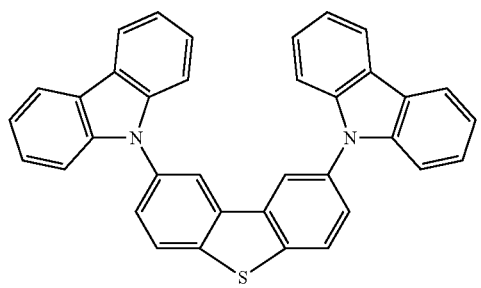
Compound H
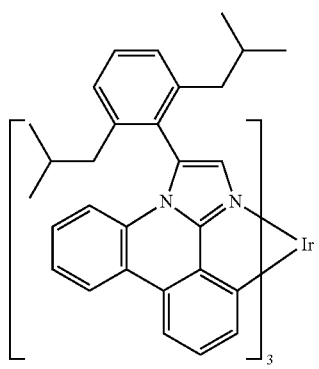
CBP
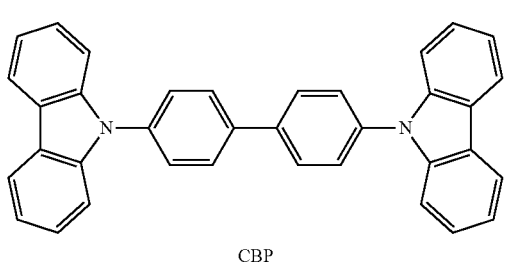

-continued

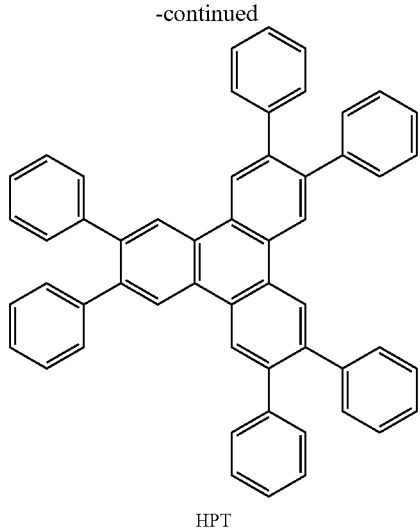

HPT

Particular emissive dopants for the emissive layer of an OLED are provided. These compounds may lead to devices having particularly good properties. The device structures are provided in Table 2, and the corresponding device data is provided in Table 3.

TABLE 2

VTE PHOLEDs

| Device Example | HIL | HTL | EML(doping %) | | BL | ETL |
|---|---|---|---|---|---|---|
| Example 1 | Compound C | NPD | Compound D | Compound 1 (7%) | Compound D | Alq3 |
| Example 2 | LG101 | NPD | Compound F | Compound 1 (10%) | Compound F | Alq3 |
| Example 3 | LG101 | NPD | Compound F | Compound 2 (10%) | Compound F | Alq3 |
| Example 4 | LG101 | NPD | Compound F | Compound 3 (10%) | Compound F | Alq3 |
| Example 5 | LG101 | NPD | Compound F | Compound 4 (10%) | Compound F | Alq3 |
| Example 6 | LG101 | NPD | Compound G | Compound 1 (10%) | Compound G | Alq3 |
| | | | Compound G | Compound H (20%) | | |
| Example 7 | LG101 | NPD | Compound G | Compound 3 (10%) | Compound G | Alq3 |
| | | | Compound G | Compound H (20%) | | |
| Comparative Example 1 | Compound C | NPD | CBP | Compound A (7%) | HPT | Alq3 |
| Comparative Example 2 | Compound C | NPD | Compound F | Compound B (9%) | HPT | Alq3 |
| Comparative Example 3 | LG101 | NPD | Compound F | Compound E (10%) | Compound F | Alq3 |

TABLE 3

VTE Device data

| | | CIE | | | At 1000 cd/m2 | | | at J = 40 mA/cm2 | |
|---|---|---|---|---|---|---|---|---|---|
| Device Example | Imax | FWHM/ nm | CIE (x) | CIE (y) | V [V] | cd/ A | EQE % | lm/W | cd/A/ EQE | Lo, nits | RT$_{80\%}$ (h) |
| Example 1 | 578 | 84 | 0.51 | 0.48 | 6.3 | 41.4 | 15.1 | 20.7 | 2.7 | 14,019 | 700 |
| Example 2 | 574 | 88 | 0.51 | 0.48 | 6.1 | 41.8 | 15.3 | 21.7 | 2.7 | 12,550 | 1150 |
| Example 3 | 572 | 86 | 0.49 | 0.51 | 6.1 | 43.5 | 14.6 | 22.3 | 3 | 13,567 | 216 |
| Example 4 | 588 | 90 | 0.54 | 0.45 | 6.8 | 29.7 | 12.7 | 13.8 | 2.3 | 9,696 | 1800 |
| Example 5 | 588 | 88 | 0.54 | 0.46 | 6.9 | 30.4 | 12.6 | 13.8 | 2.4 | 9,753 | 547 |
| Example 6 | 574 | 176 | 0.4 | 0.41 | 5.7 | 30 | 12.1 | 16.6 | 2.5 | 9,994 | 38 |
| Example 7 | 462 | 178 | 0.37 | 0.36 | 5.9 | 24.7 | 11.8 | 13.2 | 2.1 | 8,525 | 25 |
| Comparative example 1 | 519 | 74 | 0.32 | 0.62 | 6 | 45.1 | 12.6 | 23.6 | 3.6 | 13,835 | 196 |

TABLE 3-continued

| | | VTE Device data | | | | | | | | |
|---|---|---|---|---|---|---|---|---|---|---|
| | | CIE | | | At 1000 cd/m2 | | | | at J = 40 mA/cm2 | |
| Device Example | Imax | FWHM/ nm | CIE (x) | CIE (y) | V [V] | cd/ A | EQE % | lm/W | cd/A/ EQE | Lo, nits | RT$_{80\%}$ (h) |
| Comparative example 2 | 548 | 70 | 0.44 | 0.55 | 5.5 | 56.0 | 16.0 | 32 | 3.5 | 15,970 | 348 |
| Comparative example 3 | 560 | 84 | 0.44 | 0.54 | 5.6 | 53.5 | 16 | 30.3 | 3.3 | 16,415 | 252 |

In particular Device Examples 1-5 are significantly red shifted from Comparative Device Examples 1-3. This supports that the LUMO of the complex has been lowered, reducing the HOMO-LUMO gap and the triplet energy. The external quantum efficiencies of Devices 1-5 are comparable to comparative examples 1-3. In particular the device lifetimes of devices 1, 2, 4 and 5 are significantly better than comparative examples 1-3 which shows that complexes with heterocyclic groups substituted at the 4 position on the pyridine ring of the 2-phenylpyridine may also lower and stabilize the LUMO of the metal complex, thereby providing further device operational stability.

Device Example 6 shows a warm white with CIE (x=0.4. y=0.4) and Device Example 7 shows a cooler white with CIE (x=0.37. y=0.36). This supports that the compounds herein can be used to make white OLEDs with two component emitters.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A heteroleptic compound having the formula $M(L)_x(L_1)_y(L_2)_z$:

wherein L is

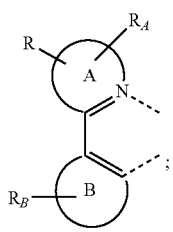

Formula I wherein $L_1$ is

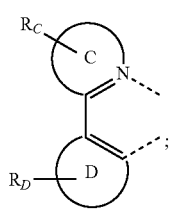

Fomula II wherein $L_2$ is

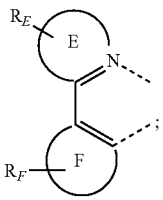

Formula III wherein $L_1$ and $L_2$ can be the same or different;
wherein M is Ir;
wherein x is 1 or 2, y is 1 or 2, z is 0, 1 or 2;
wherein x+y+z is the oxidation state of the metal M;
wherein ring C is pyridine;
wherein ring D is phenyl;
wherein rings B, E and F are each independently a 5 or 6-membered carbocyclic or heterocyclic ring;
wherein L and $L_1$ are different;
wherein R is a 6-membered heterocyclic aromatic ring that contains at least one nitrogen atom, wherein R is, optionally, further substituted by one or more of hydrogen, alkyl, alkoxy, amino, alkenyl, alkynyl, arylkyl, aryl, and heteroaryl;
wherein $R_A$, $R_B$, $R_C$, $R_D$, $R_E$ and $R_F$ may represent mono, di, tri, or tetra substitutions;
wherein each of $R_A$, $R_B$, $R_C$, $R_D$, $R_E$ and $R_F$, is independently selected from the group consisting of hydrogen, alkyl, alkoxy, amino, alkenyl, alkynyl, arylkyl, aryl, and heteroaryl; and
wherein the ligand L is coordinated bidentately to the metal M, wherein said compound is heteroleptic.

2. The compound of claim 1, wherein the ligand L has the formula:

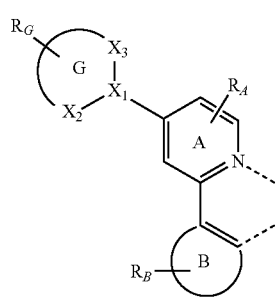

Formula IV wherein G is a 6-membered heterocyclic aromatic ring that contains at least one nitrogen atom;
wherein $X_1$, $X_2$, and $X_3$ are independently selected from carbon, oxygen, sulfur and nitrogen;

wherein $R_G$ may represent mono, di, tri, tetra, or penta substitutions;

wherein $R_G$ is independently selected from the group consisting of hydrogen, alkyl, alkoxy, amino, alkenyl, alkynyl, arylkyl, aryl, and heteroaryl.

3. The compound of claim 2, wherein $X_1$, $X_2$, and $X_3$ are independently carbon or nitrogen.

4. The compound of claim 2, wherein at least one of $X_1$, $X_2$, and $X_3$ is nitrogen.

5. The compound of claim 2, wherein each of $X_1$, $X_2$, and $X_3$ is carbon.

6. The compound of claim 2, wherein the compound has the formula:

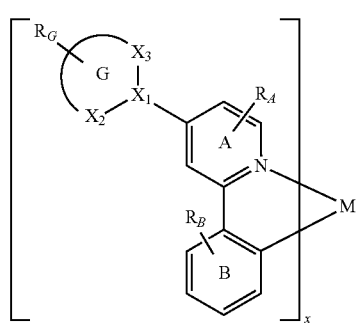

Formula VI

7. The compound of claim 1, wherein B is phenyl.

8. The compound of claim 1, wherein L, $L_1$ and $L_2$ are connected to form a tetradentate ligand and a bidentate ligand or a hexadentate ligand.

9. The compound of claim 1, wherein the ligand L is selected from the group consisting of:

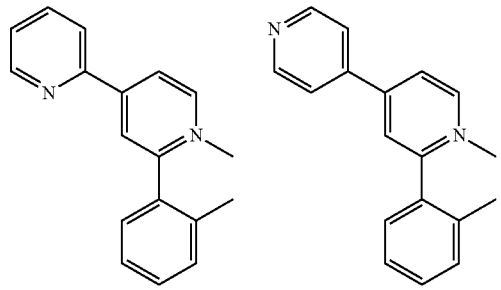

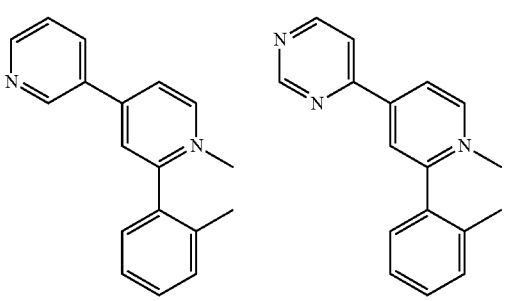

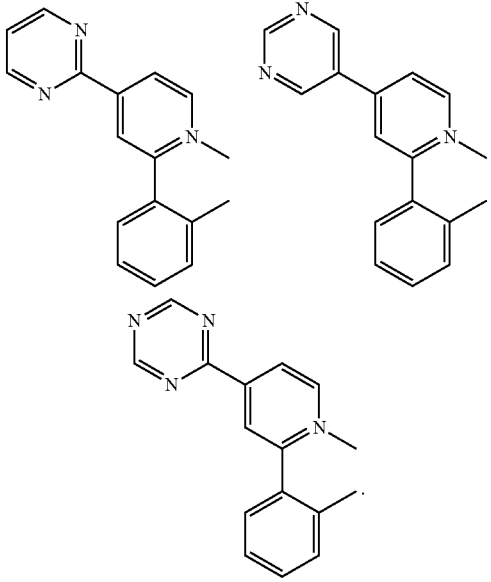

10. A compound selected from the group consisting of:

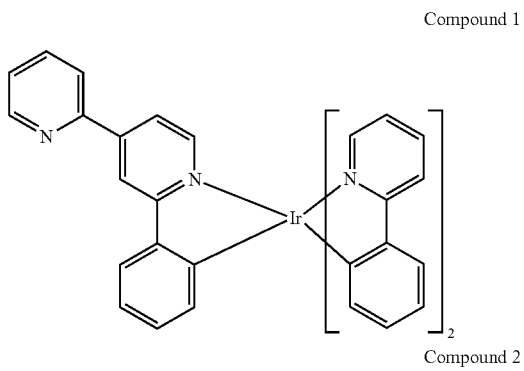

Compound 1

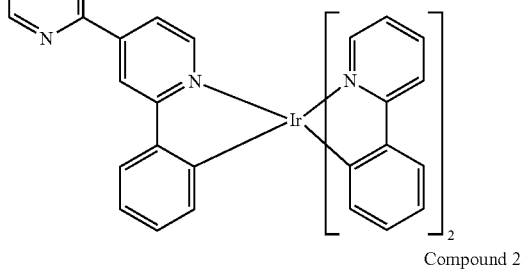

Compound 2

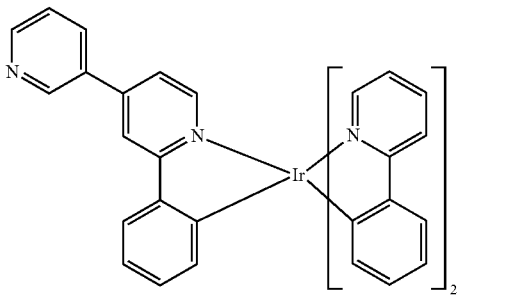

Compound 3

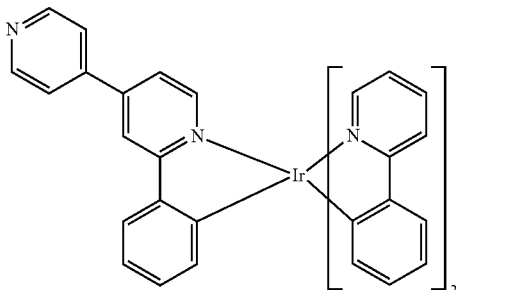

Compound 4
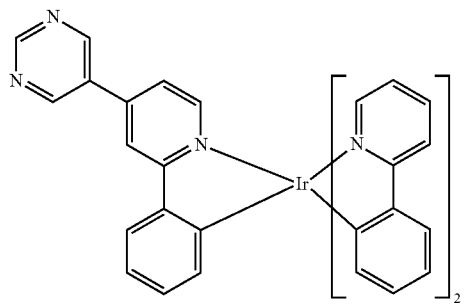
Compound 5
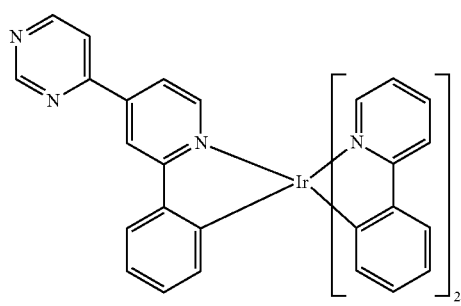
Compound 6
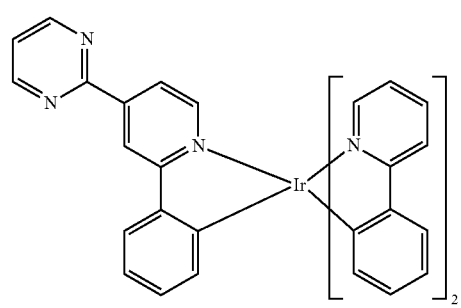
Compound 7
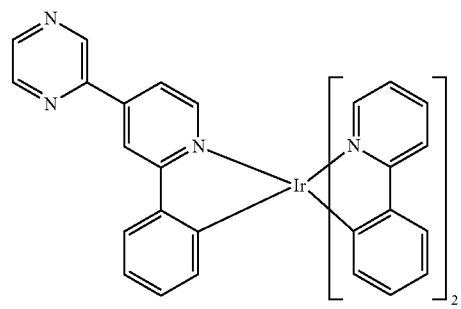
Compound 8
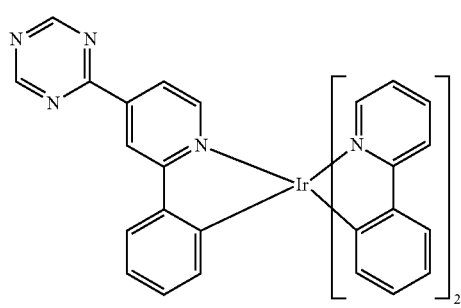
Compound 14
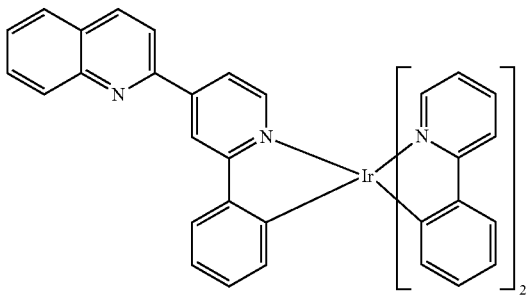
Compound 15
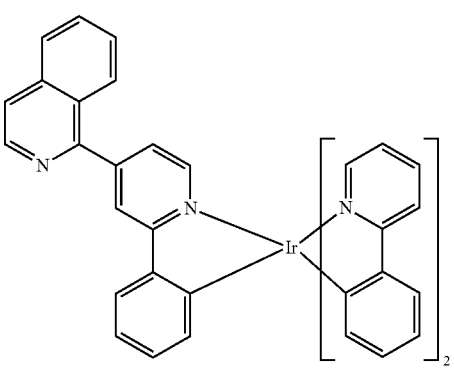
Compound 16
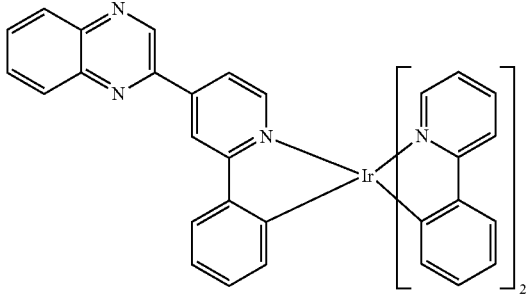
Compound 17
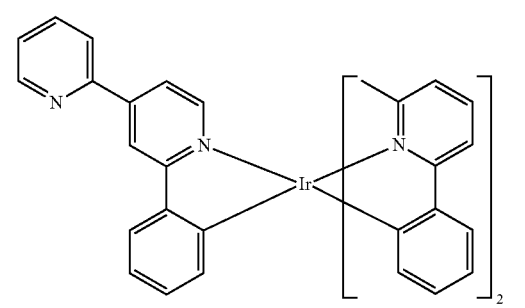

Compound 18
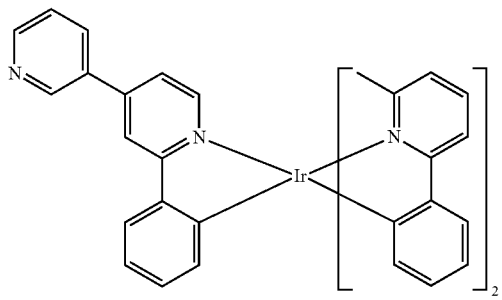
Compound 19
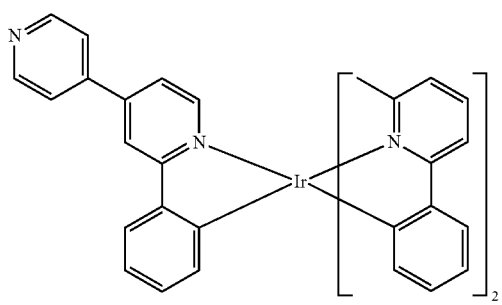
Compound 20
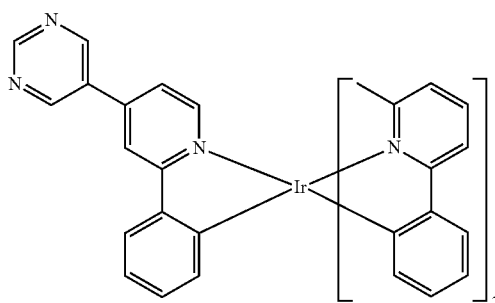
Compound 21
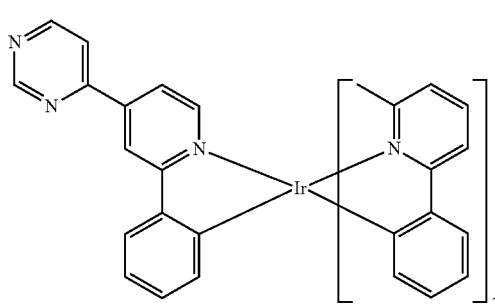
Compound 22
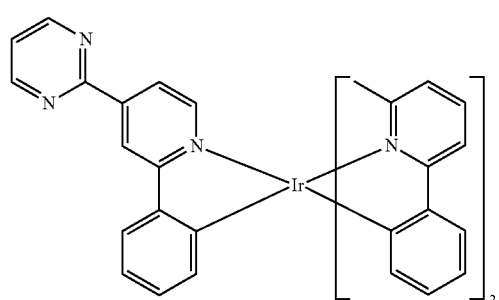
Compound 23
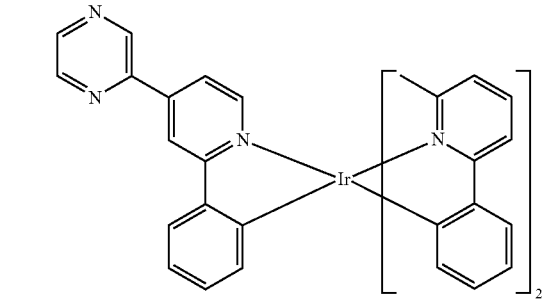
Compound 24
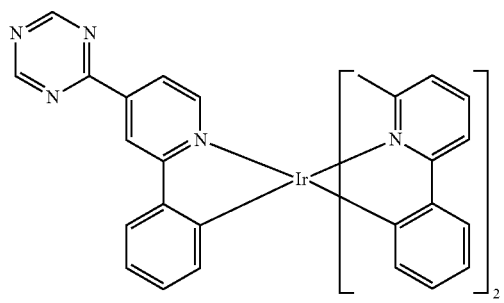
Compound 30
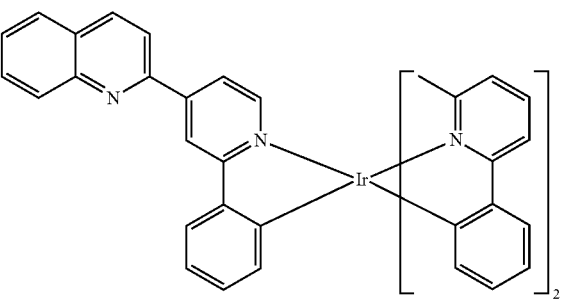
Compound 31
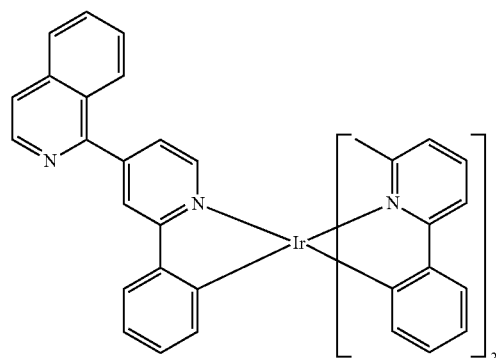

-continued

Compound 32

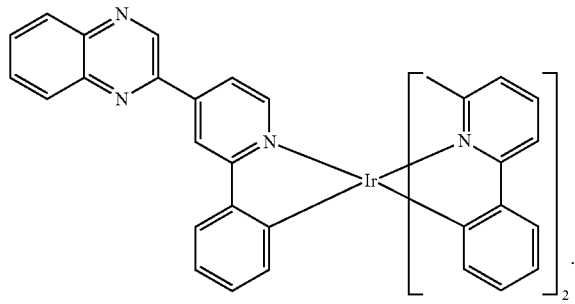

11. A first device comprising an organic light emitting device, further comprising:
an anode;
a cathode; and
an organic layer, disposed between the anode and the cathode, the organic layer comprising a first heteroleptic compound having the formula $M(L)_x(L_1)_y(L_2)_z$:
wherein L is Formula I

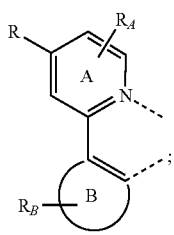

wherein $L_1$ is

Formula II

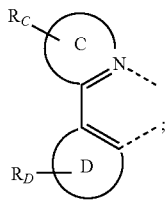

wherein $L_2$ is

Formula III

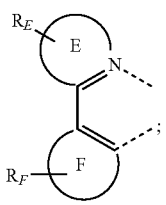

wherein $L_1$ and $L_2$ can be the same or different;
wherein M is Ir;
wherein x is 1 or 2, y is 1 or 2, z is 0, 1 or 2;
wherein x+y+z is the oxidation state of the metal M;
wherein ring C is pyridine;
wherein ring D is phenyl;
wherein rings B, E and F are each independently a 5 or 6-membered carbocyclic or heterocyclic ring;
wherein L and $L_1$ are different;
wherein R is a 6-membered heterocyclic aromatic ring that contains at least one nitrogen atom, wherein R is, optionally, further substituted by one or more of hydrogen, alkyl, alkoxy, amino, alkenyl, alkynyl, arylkyl, aryl, and heteroaryl;
wherein $R_A$, $R_B$, $R_C$, $R_D$, $R_E$ and $R_F$ may represent mono, di, tri, or tetra substitutions;
wherein each of $R_A$, $R_B$, $R_C$, $R_D$, $R_E$ and $R_F$ is independently selected from the group consisting of hydrogen, alkyl, alkoxy, amino, alkenyl, alkynyl, arylkyl, aryl, and heteroaryl; and
wherein the ligand L is coordinated bidentately to the metal M, wherein said first compound is heteroleptic.

12. The device of claim 11, wherein the ligand L has the formula:

Formula IV

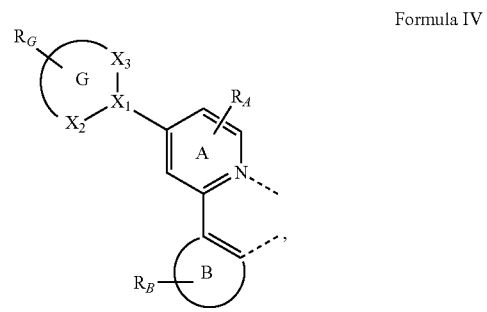

wherein G is a 6-membered heterocyclic aromatic ring that contains at least one nitrogen atom;
wherein $X_1$, $X_2$, and $X_3$ are independently selected from carbon, oxygen, sulfur and nitrogen;
wherein $R_G$ may represent mono, di, tri, tetra, or penta substitutions;
wherein $R_G$ is independently selected from the group consisting of hydrogen, alkyl, alkoxy, amino, alkenyl, alkynyl, arylkyl, aryl, and heteroaryl.

13. The device of claim 12, wherein $X_1$, $X_2$, and $X_3$ are independently carbon or nitrogen.

14. The compound of claim 12, wherein at least one of $X_1$, $X_2$, and $X_3$ is nitrogen.

15. The device of claim 12, wherein each of $X_1$, $X_2$, and $X_3$ is carbon.

16. The device of claim 12, wherein the compound has the formula:

Formula VI

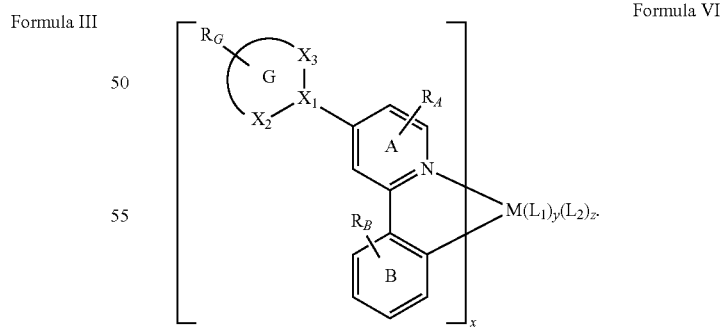

17. The device of claim 11, wherein B is phenyl.

18. The device of claim 11, wherein L, $L_1$ and $L_2$ are connected to form a tetradentate ligand and a bidentate ligand or a hexadentate ligand.

19. The device of claim 11, wherein the ligand L is selected from the group consisting of:

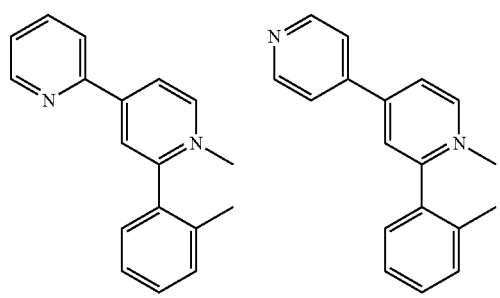
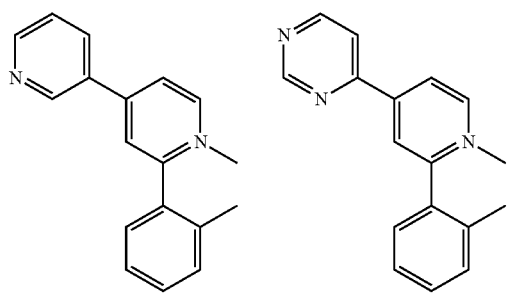
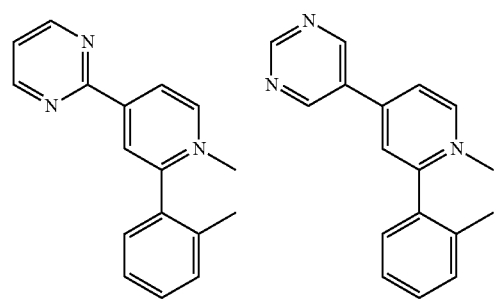
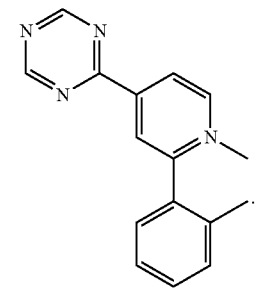
20. The device of claim 11, wherein the compound is selected from the group consisting of:
Compound 1
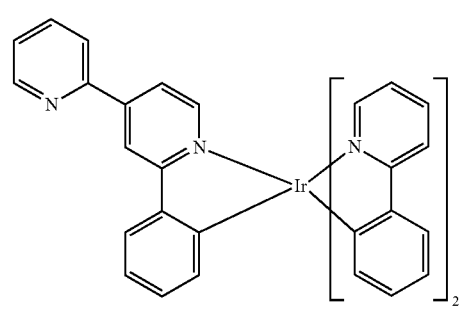
Compound 2
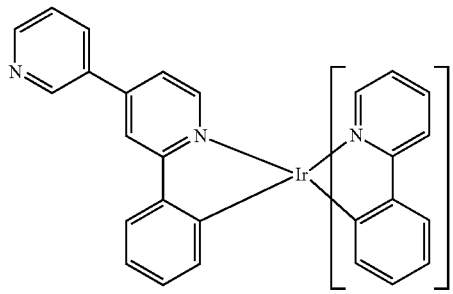
Compound 3
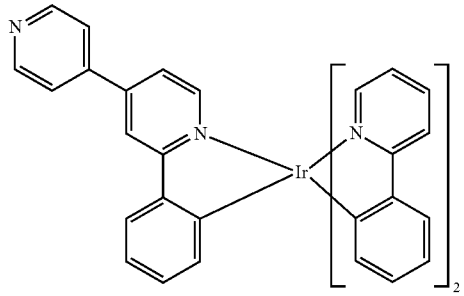
Compound 4
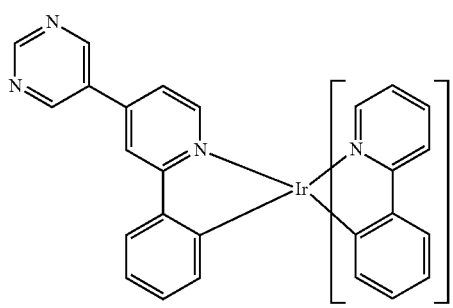
Compound 5
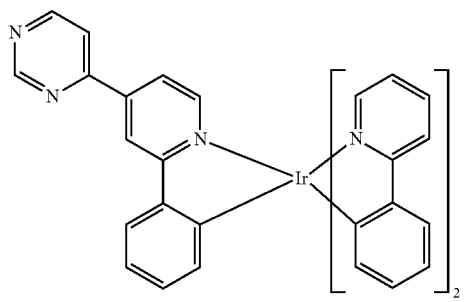
Compound 6
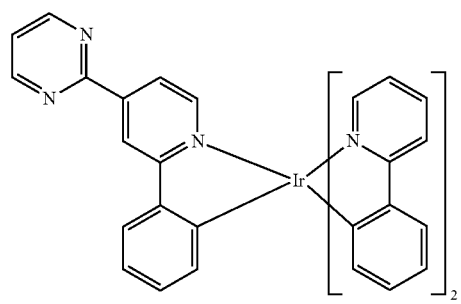

Compound 7
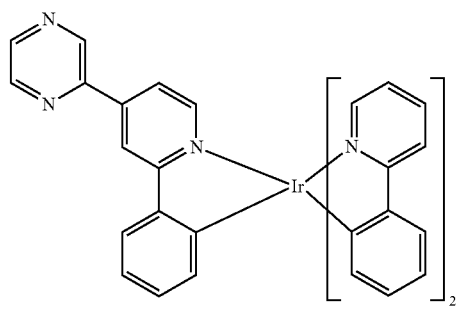
Compound 8
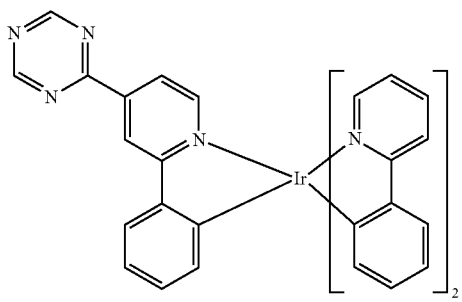
Compound 14
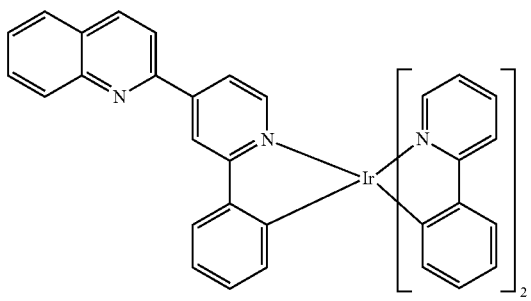
Compound 15
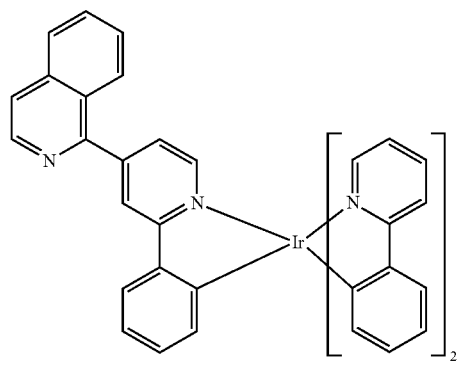
Compound 16
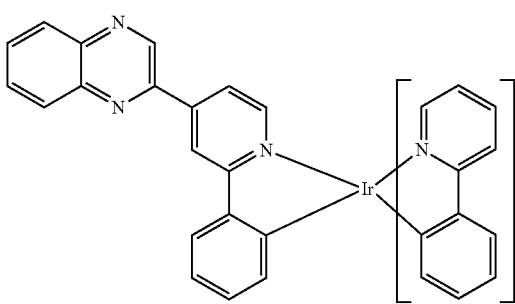
Compound 17
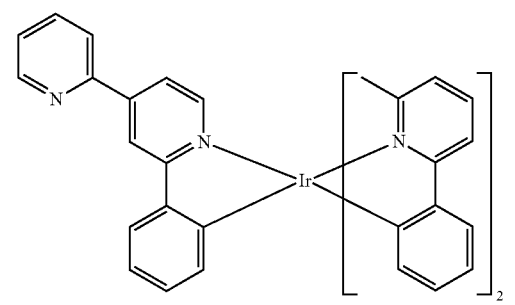
Compound 18
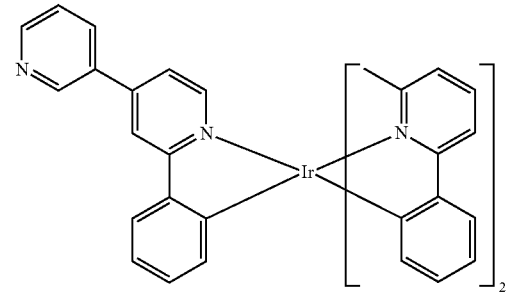
Compound 19
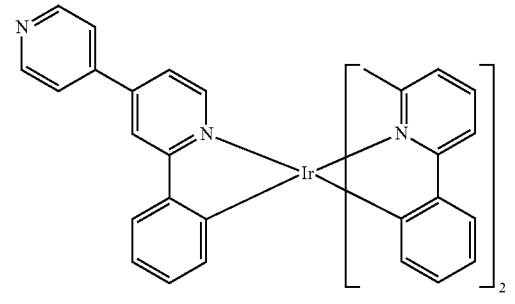
Compound 20
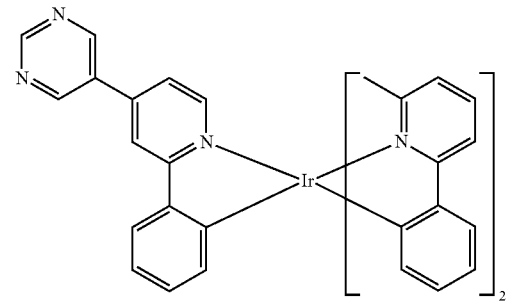

Compound 21
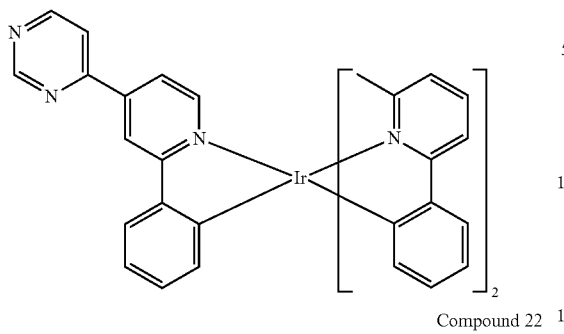

Compound 22
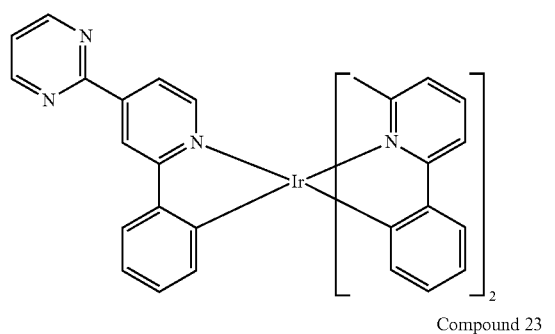

Compound 23
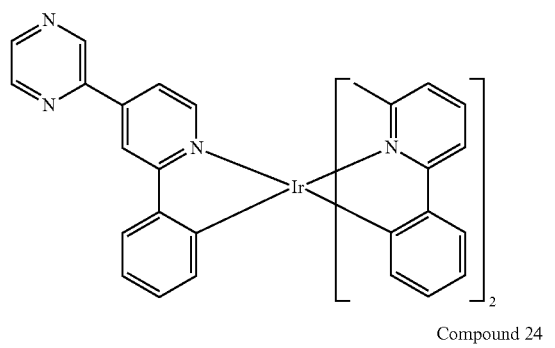

Compound 24
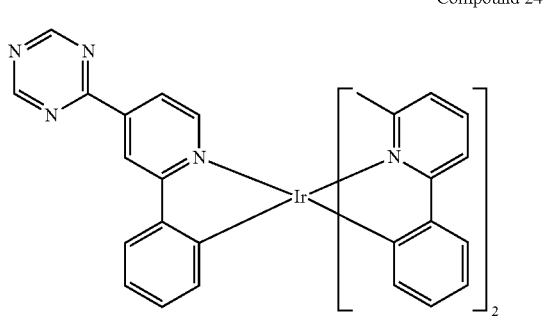

Compound 30
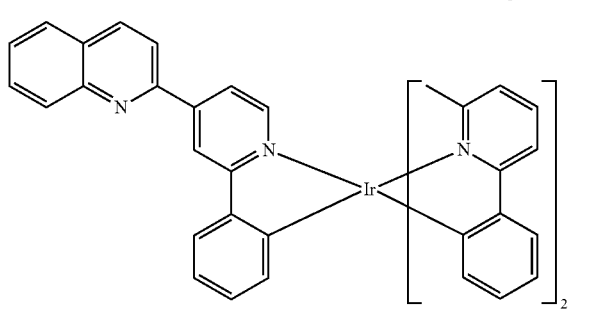

Compound 31
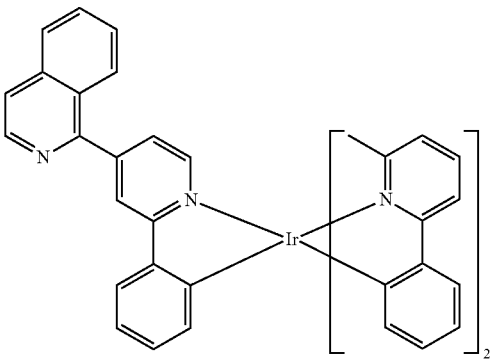

Compound 32
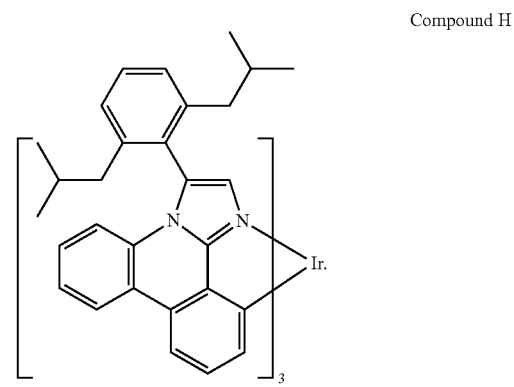

.

21. The device of claim 11, wherein the organic layer is an emissive layer and the first compound is an emissive compound.

22. The device of claim 11, wherein the organic layer further comprises a second emissive compound.

23. The device of claim 22, wherein the second emissive compound is

Compound H

24. The device of claim 11, wherein the organic layer further comprises a host having the formula:

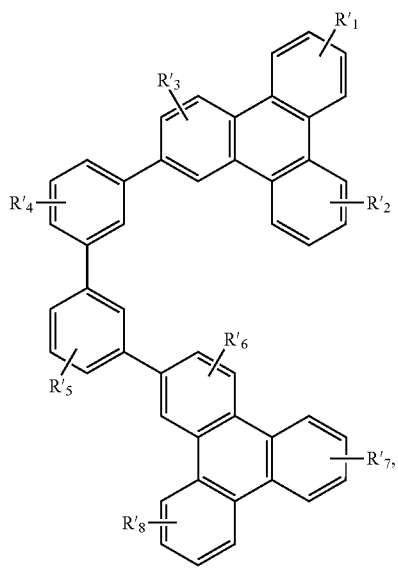

wherein R'$_1$, R'$_3$, R'$_4$, R'$_5$, R'$_6$, R'$_7$, and R'$_8$ are independently selected from the group consisting of hydrogen, alkyl, alkoxy, amino, alkenyl, alkynyl, arylkyl, aryl, and heteroaryl.

25. The device of claim 24, wherein the host is:

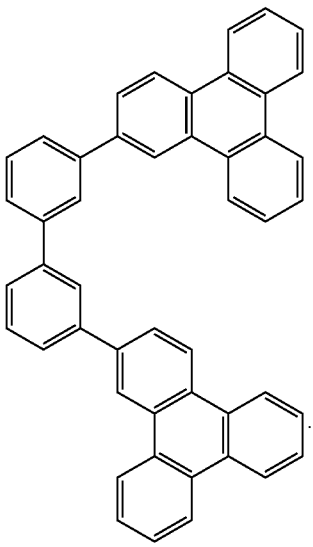

Compound F

26. The device of claim 11, wherein the first device is a consumer product.

27. The device of claim 11, wherein the first device is an organic light emitting device.

* * * * *

UNITED STATES PATENT AND TRADEMARK OFFICE
CERTIFICATE OF CORRECTION

PATENT NO.        : 9,175,211 B2                                  Page 1 of 1
APPLICATION NO.   : 12/868350
DATED             : November 3, 2015
INVENTOR(S)       : Chuanjun Xia et al.

It is certified that error appears in the above-identified patent and that said Letters Patent is hereby corrected as shown below:

In the Claims:

Claim 24, Column 159, Line 25 -- delete "$R'_1, R'_3, R'_4, R'_5, R'_6, R'_7,$ and $R'_8$"

and insert -- $R'_1, R'_2, R'_3, R'_4, R'_5, R'_6, R'_7,$ and $R'_8$ --

Signed and Sealed this
Fifth Day of April, 2016

Michelle K. Lee
*Director of the United States Patent and Trademark Office*